(12) United States Patent
Sabb et al.

(10) Patent No.: US 7,297,704 B2
(45) Date of Patent: Nov. 20, 2007

(54) CYCLOALKYFUSED INDOLE, BENZOTHIOPHENE, BENZOFURAN AND IDENE DERIVATIVES

(75) Inventors: Annmarie Louise Sabb, Pennington, NJ (US); Robert Lewis Vogel, Collingswood, NJ (US); Gary Paul Stack, Ambler, PA (US); Deborah Ann Evrard, Hamilton Square, NJ (US); Amedeo Arturo Failli, Princeton Junction, NJ (US); Lalitha Krishnan, Airmont, NY (US); Anita Wai-Yin Chan, Fort Lee, NJ (US); Jianxin Ren, Nanuet, NY (US); Charles J. Guinosso, Chestnut Ridge, NY (US); Reinhardt Bernhard Baudy, Hellertown, PA (US); Jean Yi-ching Sze, Monmouth Junction, NJ (US); Yanfang Li, Lawrenceville, NJ (US); Charles John Stanton, III, West New York, NJ (US); Antonia Nikitenko, Tarrytown, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/355,452

(22) Filed: Feb. 16, 2006

(65) Prior Publication Data

US 2006/0205759 A1    Sep. 14, 2006

Related U.S. Application Data

(60) Provisional application No. 60/653,666, filed on Feb. 17, 2005.

(51) Int. Cl.
*C07D 209/48*    (2006.01)
*C07D 207/40*    (2006.01)
*C07D 207/444*    (2006.01)

(52) U.S. Cl. .................. 514/291; 546/90; 548/438
(58) Field of Classification Search .................. 546/90
See application file for complete search history.

(56) References Cited

U.S. PATENT DOCUMENTS

| | | | | |
|---|---|---|---|---|
| 2,695,294 A | 11/1954 | Swain | ............... | 544/377 |
| 3,769,298 A | 10/1973 | McManus et al. | ............... | 548/421 |
| 3,868,387 A * | 2/1975 | Berger et al. | ............... | 548/448 |
| 4,122,202 A | 10/1978 | Fauran et al. | ............... | 514/452 |
| 4,473,586 A | 9/1984 | DeBernardis et al. | ............... | 514/605 |
| 4,618,614 A * | 10/1986 | Hausberg et al. | ............... | 514/321 |
| 4,618,683 A | 10/1986 | DeBernardis et al. | ............... | 548/420 |
| 5,049,654 A | 9/1991 | Morita et al. | ............... | 530/307 |
| 5,194,437 A | 3/1993 | Peglion et al. | ............... | 514/254.11 |
| 5,296,484 A | 3/1994 | Coghlan et al. | ............... | 514/311 |
| 5,324,743 A | 6/1994 | Dillard et al. | ............... | 514/456 |
| 5,439,909 A | 8/1995 | Guillaumet et al. | ............... | 514/254.11 |
| 5,550,125 A | 8/1996 | George et al. | ............... | 514/230.5 |
| 5,607,961 A | 3/1997 | Cipollina et al. | ............... | 514/415 |
| 5,723,484 A | 3/1998 | Lavielle et al. | ............... | 514/410 |
| 5,750,556 A | 5/1998 | Mewshaw et al. | ............... | 514/411 |
| 5,814,653 A | 9/1998 | Flaugh et al. | ............... | 514/411 |
| 5,830,911 A | 11/1998 | Failli et al. | ............... | 514/411 |
| 5,935,992 A | 8/1999 | Flaugh et al. | ............... | 514/444 |
| 6,063,810 A | 5/2000 | Philippo et al. | ............... | 514/469 |
| 6,071,860 A | 6/2000 | Giencke et al. | ............... | 504/232 |
| 6,221,879 B1 | 4/2001 | Marabout et al. | ............... | 514/304 |
| 6,303,603 B1 | 10/2001 | Patoiseau et al. | ............... | 514/242 |
| 6,432,956 B1 | 8/2002 | Dement et al. | ............... | 514/252.1 |
| 6,555,559 B1 | 4/2003 | Wakita et al. | ............... | 514/337 |
| 6,599,915 B2 * | 7/2003 | Tran et al. | ............... | 514/291 |
| 6,693,197 B2 | 2/2004 | Chan et al. | ............... | 546/90 |
| 6,747,024 B1 | 6/2004 | Auvin et al. | ............... | 514/224.8 |
| 6,762,176 B1 | 7/2004 | Chabrier de Lassauniere et al. | ............... | 514/183 |
| 6,919,360 B2 | 7/2005 | Scherling et al. | ............... | 514/367 |
| 7,045,629 B2 | 5/2006 | Bokel et al. | ............... | 546/207 |
| 2002/0016359 A1 | 2/2002 | Hellberg et al. | ............... | 514/456 |
| 2002/0177616 A1 | 11/2002 | Fahrig et al. | ............... | 514/373 |
| 2003/0045537 A1 | 3/2003 | Lee et al. | ............... | 514/267 |
| 2003/0073839 A1 | 4/2003 | Ladouceur et al. | ............... | 544/376 |
| 2003/0134870 A1 | 7/2003 | Stack et al. | ............... | 514/300 |
| 2003/0225088 A1 | 12/2003 | Sikorski et al. | ............... | 514/242 |
| 2004/0077652 A1 | 4/2004 | Gross et al. | ............... | 514/250 |

FOREIGN PATENT DOCUMENTS

| | | |
|---|---|---|
| CA | 924305 | 4/1973 |
| DE | 4419973 A1 | 12/1995 |
| DE | 196 48 384 A1 | 5/1998 |
| DE | 19754573 A1 | 6/1999 |
| EP | 0 004 358 B1 | 1/1982 |
| EP | 0 054 304 B1 | 8/1984 |
| EP | 0 038 564 B1 | 9/1984 |
| EP | 0 323 807 A2 | 7/1989 |
| EP | 0 378 518 A2 | 7/1990 |
| EP | 0 236 930 B1 | 10/1990 |
| EP | 0 492 021 A1 | 7/1992 |
| EP | 0 518 436 A1 | 12/1992 |
| EP | 0 325 963 B1 | 9/1993 |
| EP | 0 558 245 A1 | 9/1993 |

(Continued)

OTHER PUBLICATIONS

U.S. Appl. No. 10/898,866, filed Jun. 2004, Hatzenbuhler et al.*

(Continued)

*Primary Examiner*—Cecilia J. Tsang
*Assistant Examiner*—David K O'Dell
(74) *Attorney, Agent, or Firm*—Woodcock Washburn LLP

(57) ABSTRACT

The present invention provides cycloalkylfused indole, benzothiophene, benzofuran, and indene derivatives, and methods for using them to, for example, treat, prevent and/or ameliorate central nervous system diseases by antagonizing 5-HT$_{1A}$ receptors and modulating serotonin levels.

1 Claim, No Drawings

FOREIGN PATENT DOCUMENTS

| | | |
|---|---|---|
| EP | 0 345 747 B1 | 6/1996 |
| EP | 0 905 136 A1 | 3/1999 |
| EP | 0 884 049 B1 | 9/2002 |
| EP | 1 375 503 A1 | 1/2004 |
| EP | 1 424 337 A1 | 6/2004 |
| FR | 2729141 A1 | 7/1996 |
| GB | 1 005 028 A | 9/1965 |
| GB | 1 249 261 A | 10/1971 |
| GB | 2 174 705 A | 11/1986 |
| JP | 58219114 | 12/1983 |
| JP | 1146876 A | 6/1989 |
| JP | 11189536 | 7/1999 |
| JP | 2003212872 | 7/2003 |
| JP | 2003335669 | 11/2003 |
| JP | 2004059538 | 2/2004 |
| WO | 91/13872 A1 | 9/1991 |
| WO | 92/15579 A1 | 9/1992 |
| WO | 92/21671 A1 | 12/1992 |
| WO | 94/14805 A1 | 7/1994 |
| WO | 94/22846 A1 | 10/1994 |
| WO | 96/38441 A1 | 12/1996 |
| WO | 96/39145 A1 | 12/1996 |
| WO | 97/15308 A1 | 5/1997 |
| WO | 97/17343 A1 | 5/1997 |
| WO | 97/23485 A1 | 7/1997 |
| WO | 97/35852 A1 | 10/1997 |
| WO | 97/47601 A1 | 12/1997 |
| WO | 98/40386 A1 | 9/1998 |
| WO | 99/29687 A1 | 6/1999 |
| WO | 99/32476 A1 | 7/1999 |
| WO | 99/62902 A1 | 12/1999 |
| WO | 99/64420 A1 | 12/1999 |
| WO | 00/20423 A1 | 4/2000 |
| WO | 00/35432 A2 | 6/2000 |
| WO | 00/58301 A1 | 10/2000 |
| WO | 00/75136 A1 | 12/2000 |
| WO | 01/10433 A1 | 2/2001 |
| WO | 01/41750 A2 | 6/2001 |
| WO | 01/72741 A2 | 10/2001 |
| WO | 02/44152 A1 | 6/2002 |
| WO | 02/49993 A2 | 6/2002 |
| WO | 02/55012 A2 | 7/2002 |
| WO | 02/85891 A1 | 10/2002 |
| WO | 02/85912 A1 | 10/2002 |
| WO | 02/088133 A1 | 11/2002 |
| WO | 02/088134 A2 | 11/2002 |
| WO | 02/088135 A1 | 11/2002 |
| WO | 02/088136 A2 | 11/2002 |
| WO | 02/088141 A2 | 11/2002 |
| WO | 02/088142 A1 | 11/2002 |
| WO | 02/092602 A2 | 11/2002 |
| WO | 02/008420 A1 | 1/2003 |
| WO | 03/008419 A1 | 1/2003 |
| WO | 03/013511 A1 | 2/2003 |
| WO | 03/013705 A1 | 2/2003 |
| WO | 03/022269 A1 | 3/2003 |
| WO | 03/024960 A1 | 3/2003 |
| WO | 03/029238 A1 | 4/2003 |
| WO | 03/029239 A1 | 4/2003 |
| WO | 03/030901 A1 | 4/2003 |
| WO | 03/031429 A1 | 4/2003 |
| WO | 03/055890 A1 | 7/2003 |
| WO | 03/068253 A1 | 8/2003 |
| WO | 03/104216 A1 | 12/2003 |
| WO | 2004/016601 A1 | 2/2004 |
| WO | 2004/024732 A1 | 3/2004 |
| WO | 2004/024734 A1 | 3/2004 |

OTHER PUBLICATIONS

Hegedus et. al. J. Am. Chem. Soc. 1978, 100, 5800-5807.*
Campbell et. al. Chemical Reviews 1947, 40, 359-380.*
Robinson, et. al. Chemical Reviews 1963, 63, 373-401.*
Amundsen, L.H. et. al. J. Am. Chem. Soc, 1951, 73, 242-244.*
Database Beilstein. Beilstein Institute for Organic Chemistry, Frankfurt-Main, DE; XP002402724 Database accession No. BRN:5266967 abstract & Tetrahedron, vol. 41, No. 12, 1985, pp. 2557-2566.
Database Beilstein. Beilstein Institute for Organic Chemistry, Frankfurt-Main, DE; XP002402725 Database accession No. BRN:6333133 abstract & Naunyn-Schmiedeberg's Arch. Pharmacol., vol. 355, No. 4, 1997, pp. 475-482.
Database Beilstein. Beilstein Institute for Organic Chemistry, Frankfurt-Main, DE; XP002402726 Database accession No. BRN:151106 abstract & J. Indian Chem. Soc., vol. 34, 1957, pp. 299-304.
Database Beilstein. Beilstein Institute for Organic Chemistry, Frankfurt-Main, DE; XP002402727 Database accession No. BRN:415101 abstract & Justus Liebigs Ann. Chem. vol. 709, 1967, pp. 135-150.
Database Beilstein. Beilstein Institute for Organic Chemistry, Frankfurt-Main, DE; XP002402728 Database accession No. BRN:9274684 abstract & J. Med. Chem., vol. 45, No. 18, 2002, pp. 3509-3523.
Database Beilstein. Beilstein Institute for Organic Chemistry, Frankfurt-Main, DE; XP002402729 Database accession No. BRN:165230 abstract & J. Indian. Chem. Soc., vol. 34, 1957, pp. 299-304.
Database Beilstein. Beilstein Institute for Organic Chemistry, Frankfurt-Main, DE; XP002402730 Database accession No. BRN:189711 abstract & Bull. Soc. Chim. Fr., 1952, pp. 336-340.
Glennon, R. A. et al., "2-Substituted Tryptamines: Agents with Selectivity for 5-$HT_6$ Serotonin Receptors," Journal of Medicinal Chemistry, American Chemical Society, Washinton, US, vol. 43, No. 5, 2000, pp. 1011-1018, XP002201555.
Block, M. H., et al., "Discovery and Optimization of a Series of Carbazole Ureas as NPY5 Antagonists for the Treatment of Obesity," *J. Med. Chem.* 2002, 45, 3509-3523.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4), 285-298.
Bundgaard, H., "Means to enhance penetration; Prodrugs as a means to improve the delivery of peptide drugs," *Advanced Drug Deliver Reviews*, 1992, 8, 1-38.
Cheetham, S. C. et al., "[$^3$H]Paroxetine Binding in Rat Frontal Cortex Strongly Correlates With [$^3$H]Paroxetine Binding in Rat Frontal Cortex Strongly Correlates With [$^3$H]5-HT Uptake: Effect of Administration of Various Antidepressant Treatments," *Neuropharmacol.*, 1993, 32(8), 737-743.
Cheng, Y-C. et al., "Relationship between the inhibition constant ($K_1$) and the concentration of inhibitor which causes 50 per cent inhibition ($I_{50}$) of an enzymatic reaction," *Biochem. Pharmacol.*, 1973, 22, 3099-3108.
Higuchi and Stella (eds.), *Prodrugs as Novel Drug Delivery Systems*, American Chemical Society (1975), pp. 1-115 and 196-223.
Krogsgaard-Larsen, et al., (ed). *Design and Application of Prodrugs, Textbook of Drug Design and Development*, Chapter 5, 113-191, 1991.
Lazareno, S. and Birdsall, N.J.M., "Pharmacological characterization of acetylcholine-stimulated [$^{35}$S]-GTPγS binding mediated by human muscarinic m1—m4 receptors: antagonist studies," *Br. J. Pharmacol.*, 1993, 109, 1120-1127.
*Remington's Pharmaceutical Sciences*, 17th Ed., Gennaro, A. R. (Ed.), Mack Publishing Company, Easton, PA (1985) pp. 1409-1677.
Widder, et al. (ed.), *Methods in Enzymology*, vol. 112, Academic Press (1985), pp. 309-323.

Amantini, D., et al., "3-Nitrocoumarins as Dienophiles in the Diels—Alder Reaction in Water. An Approach to the Synthesis of Nitrotetrahydrobenzo[c]chromenones and Dihydrodibenzo[b,d]furans," *J. Org. Chem.*, 68, 9263-68, 2003.

Berridge, M. S. et al., "Preparation and In Vivo Binding of [11C]Carazolol, a Radiotracer for the Beta-adrenergic Receptor," *Nucl. Med. Biol.*, 19 (5) 563-569, 1992.

Borch, R. F. et al., "A Novel Synthesis of 2-Oxo-1,2,3,4-tetrahydrocarbazoles," *J. Org. Chem.*, 38 (15), 2729, 1973.

Dauzonne, D., and Royer, R., "A Convenient One-Flask Synthesis of 3-Nitrocoumarins," *Synthesis*, 836-837, 1983.

Halterman, R. L. et al., "Efficient synthesis of 2- and 2-substituted indenes from 2-bromobenzyl bromide through an enolate alkylation/Cr(II)/(Ni(II)-mediated carbonyl addition sequence," *Tetrahedron Letters*, 1999, 40, 7445-7448.

Taylor, E. W., "Synthesis of a conformationally restricted Tryptamine analog via an improved reduction of a derivative of Uhle's Ketone," *Synthetic Communications*, 1989, 19 (3&4), 369-372.

\* cited by examiner

CYCLOALKYFUSED INDOLE, BENZOTHIOPHENE, BENZOFURAN AND IDENE DERIVATIVES

CROSS REFERENCE TO RELATED APPLICATIONS

The present application claims benefit of Provisional Application Ser. No. 60/653,666, filed Feb. 17, 2005, the disclosure of which is hereby incorporated by reference in its entirety.

FIELD OF THE INVENTION

The present invention relates to cycloalkylfused indole, benzothiophene, benzofuran, and indene derivatives, pharmaceutical compositions containing them and methods for their use as, for example, serotonin modulators.

BACKGROUND OF THE INVENTION

Major depressive disorder affects an estimated 340 million people worldwide. Depression is the most frequently diagnosed psychiatric disorder, and according to the World Health Organization, it is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also results in more than $40 billion in annual costs in the United States alone, due to premature death, lost productivity, and absenteeism.

Selective serotonin reuptake inhibitors (SSRIs) have had significant success in treating depression and related illnesses and have become among the most prescribed drugs since the 1980's. Some of the most widely known are fluoxetine, sertraline, paroxetine, fluvoxamine and citalopram. Although they have a favorable side effect profile compared to tricyclic antidepressants (TCAs), they have their own particular set of side effects from the non-selective stimulation of serotonergic sites. They have a slow onset of action, often taking several weeks to produce their full therapeutic effect. Furthermore, they are effective in less than two-thirds of patients.

SSRIs work by blocking the neuronal reuptake of serotonin, which tends to increase the concentration of serotonin in the synaptic space, and thus increase the activation of postsynaptic serotonin receptors. Although a single dose of a SSRI can inhibit the neuronal serotonin transporter and thus would be expected to increase synaptic serotonin, clinical improvement is achieved only after long-term treatment. It has been suggested that the delay in onset of antidepressant action of the SSRIs is the result of an increase in serotonin levels in the vicinity of the serotonergic cell bodies. This excess serotonin activates somatodendritic autoreceptors, 5-HT$_{1A}$ receptors, which reduces cell firing activity and, in turn, causes a decrease in serotonin release in major forebrain areas. This negative feedback limits the increment of synaptic serotonin that can be induced by antidepressants acutely. Over time, the somatodendritic autoreceptors become desensitized allowing the full effect of the SSRIs to be expressed in the forebrain. This time period corresponds to the latency for the onset of antidepressant activity [Perez, V., et al., *The Lancet,* 349:1594-1597 (1997)].

In contrast to the SSRIs, a 5-HT$_{1A}$ agonist or partial agonist acts directly on postsynaptic serotonin receptors to increase serotonergic neurotransmission during the latency period for the SSRI effect. Accordingly, the 5-HT$_{1A}$ partial agonists buspirone and gepirone [Feiger, A., *Psychopharmacol. Bull.,* 32 (4), 659-665 (1996), Wilcox, C., *Psychopharmacol. Bull,* 32 (93), 335-342 (1996)] and the 5-HT$_{1A}$ agonist flesinoxan [Grof, P., *International Clinical Psychopharmacology,* 8 (3), 167-172 (1993)] have shown efficacy in clinical trials for the treatment of depression. Furthermore, such agents would also stimulate the somatodendritic autoreceptors, thus hastening their desensitization and decreasing the SSRI latency period. An agent with a dual mechanism of antidepressant action, i.e. increases serotonin levels by blocking neuronal reuptake of serotonin and desensitizes somaticdendritic autoreceptors, would be expected to have greater efficacy and thus reduce the number of patients refractory to treatment. Indeed, buspirone augmentation to standard SSRI therapy has been shown to produce marked clinical improvement in patients initially unresponsive to standard antidepressant therapy [Dimitriou, E., *J. Clinical Psychopharmacol.,* 18(6), 465-469 (1998)].

Lacking from the current therapy regime, however, is a single compound that effectively displays the dual mechanism of antidepressant action, i.e., one that not only inhibits or blocks serotonin reuptake (and thereby increases the levels of serotonin in the synapse), but also antagonizes the 5-HT$_{1A}$ receptors (and thereby reduces the latency period). The present invention is directed to these, as well as other, important ends.

SUMMARY OF THE INVENTION

In one aspect, the present invention provides novel cycloalkylfused indole, benzothiophene, benzofuran, and indene derivatives that, for example, act as serotonin modulators.

Certain compounds according to the invention are those of formula I:

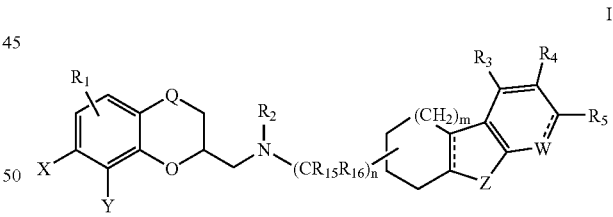

or pharmaceutically-acceptable salts thereof;
wherein:
$R_1$, $R_3$, $R_4$, and $R_5$ are independently hydrogen, halo, cyano, carboxamido, carboalkoxy, trifluoromethyl, alkyl, $OR_9$, trifluoromethoxy, alkanoyl, alkanoyloxy, amino, monoalkylamino, dialkylamino, alkanamido, alkanesulfonyl, alkanesulfonamido, or phenyl;

W is N, $NR_6$, or $CR_6$;

$R_6$ is hydrogen, halo, cyano, carboxamido, carboalkoxy, trifluoromethyl, alkyl, $OR_9$, trifluoromethoxy, alkanoyl, alkanoyloxy, amino, monoalkylamino, dialkylamino, alkanamido, alkanesulfonyl, alkanesulfonamido, or phenyl;

R$_2$ is hydrogen, alkyl, cycloalkyl, CH$_2$cycloalkyl, or benzyl;

X and Y are independently hydrogen, halo, hydroxy, cyano, carboxamido, carboalkoxy, trifluoromethyl, alkyl, alkoxy, alkanoyl, alkanoyloxy, amino, monoalkylamino, dialkylamino, alkanamido, alkanesulfonyl, alkanesulfonamido, phenyl, X and Y together with the atoms to which they are attached, form —N=C(R$_7$)C(R$_8$)=N—, —N=C(R$_7$)C(R$_9$)=CH—, —N=C(R$_7$)N=C(R$_9$)—, —CH=C(R$_7$)C(R$_9$)=CH—, —N=C(R$_{10}$)O—, —NH—C(R$_{11}$)=CH—, NH—C(R$_{17}$)O—, =N—O—C(R$_{18}$)=, —NH—N—C(R$_{18}$)—, —NH—(CR$_{17}$)=N—, —NH—C(R$_{10}$)=CH—, —O—C(=O)C(R$_9$)—, —O—C(R$_7$)C(R$_9$)—, —O—C(=O)—NR$_9$—, —O—C(R$_9$)=CH—, —O—N=C(R$_9$)—, or —O—C(R$_9$)=N;

R$_7$ and R$_8$ are independently hydrogen, halo, amino, monoalkylamino, dialkylamino, or alkyl;

R$_9$ is hydrogen or alkyl;

R$_{10}$ is hydrogen, halo, trifluoromethyl, pentafluoroethyl, amino, monoalkylamino, dialkylamino, alkoxy or alkyl;

R$_{11}$ is hydrogen, halo, trifluoromethyl, pentafluoroethyl, or alkyl;

Z is N(R$_{12}$), O, S, or C(R$_{13}$R$_{14}$);

R$_{12}$, R$_{13}$ and R$_{14}$ are independently hydrogen or alkyl;

R$_{15}$ and R$_{16}$ are independently at each occurrence, H or C$_1$-C$_3$ alkyl;

R$_{17}$ is hydrogen, halo, cyano, carboxamido, carboalkoxy, trifluoromethyl, alkyl, alkanoyloxy, amino, monoalkylamino, dialkylamino, alkanamido, or alkanesulfonamido;

R$_{18}$ is hydrogen, carboxy, cyano, carboxamido, carboalkoxy, trifluoromethyl, amino, monoalkylamino, dialkylamino, monoalkylamino, dialkylamino, alkoxy, or alkyl;

Q is O, S, or CH$_2$;

a dotted line represents an optional double bond; and n and m are independently integers of 0, 1, 2 or 3.

Preferred among the above noted R$_1$ group in formula I are hydrogen and methyl.

Preferred among the above noted R$_2$ group in formula I are hydrogen, methyl, ethyl, propyl, isobutyl, cyclopropylmethyl, cyclobutyl, cyclopentyl, and cyclohexyl.

Preferred among the above noted R$_3$, R$_4$, and R$_5$ groups in formula I are hydrogen, fluoro, chloro, cyano, and trifluoromethoxy.

Preferred among the above noted R$_7$, R$_8$, R$_9$, R$_{10}$R$_{11}$, R$_{12}$, R$_{13}$, and R$_{14}$ groups in formula I are hydrogen and methyl.

Preferred among the above noted X and Y groups in formula I are those in which X and Y, together with the atoms to which they are attached form —N=C(R$_7$)C(R$_9$)=CH—, N=C(R$_7$)N=C(R$_9$)—, and —NH—C(R$_{11}$)=CH—.

Also preferred among the above noted X and Y groups in formula I are those in which X and Y, together with the atoms to which they are attached form —N=C(R$_7$)O—, —NH—C(R$_{10}$)=N—, or —NH—C(R$_{11}$)=CH—.

Preferred among the above noted W group in formula I is CR$_6$. Preferred among the above noted R$_6$ group in formula I are hydrogen, fluoro, chloro, cyano, and trifluoromethoxy.

Preferred among the above noted Z groups in formula I are NR$_{12}$ and S.

Preferred among the above noted Q groups in formula I are O and CH$_2$.

Preferred among the above noted n and m in formula I are 1 and 2.

In one embodiment, the present invention is also directed to compounds of formula II:

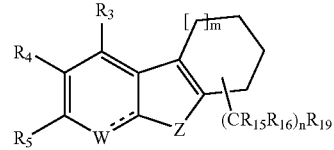

or pharmaceutically-acceptable salts thereof;

wherein:

R$_3$, R$_4$, and R$_5$ are independently hydrogen, halo, cyano, carboxamido, carboalkoxy, trifluoromethyl, alkyl, OR$_9$, trifluoromethoxy, alkanoyl, alkanoyloxy, amino, monoalkylamino, dialkylamino, alkanamido, alkanesulfonyl, alkanesulfonamido, or phenyl;

W is N, NR$_6$ or CR$_6$;

R$_6$ is hydrogen, halo, cyano, carboxamido, carboalkoxy, trifluoromethyl, alkyl, OR$_9$, trifluoromethoxy, alkanoyl, alkanoyloxy, amino, monoalkylamino, dialkylamino, alkanamido, alkanesulfonyl, alkanesulfonamido, or phenyl;

R$_9$ is hydrogen or alkyl;

Z is N(R$_{12}$), O, S, or C(R$_{13}$R$_{14}$);

R$_{12}$, R$_{13}$ and R$_{14}$ are independently hydrogen or alkyl;

R$_{15}$ and R$_{16}$ are independently at each occurrence, H or C$_1$-C$_3$ alkyl;

R$_{19}$ is —C(=O)—O—C$_2$H$_5$, —C(=O)—OH, —C(=O)—NH$_2$, —(CH$_2$)$_p$—NH$_2$, —C(=O)H, —C(≡N), —OH, =O, or =N—OH;

n, m, and p are independently integers of 0, 1, 2, or 3.

The following compounds are particularly preferred:

N-[(6-fluoro-2,3,4,9-tetrahydro-1H-carbazol-2-yl)methyl]-N-{[(2S)-8-methyl-2,3-dihydro[1,4]dioxino[2,3-f]quinolin-2-yl]methyl}amine;

N-[(6-fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

N-{[(3S)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-[(6-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

N-{[(3S)-6-fluoro-9-methyl-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-6-fluoro-9-methyl-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-6,8-difluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3S)-6,8-difluoro-2,3,4,9-tetrahydro-1H-carbazol-3-yl]methyl}-N-{[(2S)-2,3-dihydro[1,4]dioxino[2,3-f]quinolin-2-yl]methyl}amine;

[(5-fluoro-2,3,4,9-tetrahydro-1H-carbazol-3-yl)methyl]{[(2S)-8-methyl-2,3-dihydro[1,4]dioxino[2,3-f]quinolin-2-yl]methyl}amine;

N-[(5-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

N-[(7-fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

(3S)-3-[({[(2S)-8-methyl-2,3-dihydro[1,4]dioxino[2,3-f]quinolin-2-yl]methyl}amino)methyl]-2,3,4,9-tetrahydro-1H-carbazole-6-carbonitrile;

(3R)-3-[({[(2S)-8-methyl-2,3-dihydro[1,4]dioxino[2,3-f]quinolin-2-yl]methyl}amino)methyl]-2,3,4,9-tetrahydro-1H-carbazole-6-carbonitrile;

2-(6-Fluoro-2,3,4,9-tetrahydro-1H-carbazol-3-yl)ethyl]{[(2S)-8-methyl-2,3-dihydro[1,4]dioxino[2,3-f]quinolin-2-yl]methyl}amine;

{2-[(3R)-6-Fluoro-2,3,4,9-tetrahydro-1H-carbazol-3-yl]ethyl}{[(2S)-8-methyl-2,3-dihydro[1,4]dioxino[2,3-f]quinolin-2-yl]methyl}amine;

{2-[(3S)-6-Fluoro-2,3,4,9-tetrahydro-1H-carbazol-3-yl]ethyl ({[(2S)-8-methyl-2,3-dihydro[1,4]dioxino[2,3-f]quinolin-2-yl]methyl}amine;

N-{[(2S)-8-methyl-2,3-dihydro[1,4]dioxino[2,3-f]quinolin-2-yl]methyl}-2,3,4,9-tetrahydro-1H-carbazol-2-amine;

(2R)-N-{[(2S)-8-methyl-2,3-dihydro[1,4]dioxino[2,3-f]quinolin-2-yl]methyl}-2,2,4,9-tetrahydro-1H-carbazol-2-amine;

(2S)-N-{[(2S)-8-methyl-2,3-dihydro[1,4]dioxino[2,3-f]quinolin-2-yl]methyl}-2,3,4,9-tetrahydro-1H-carbazol-2-amine;

6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

(2R)-6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

(2S)-6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

[(8-Fluoro-1,2,3,4-tetrahydrodibenzo[b,d]thien-2-yl)methyl]{[(2S)-8-methyl-2,3-dihydro[1,4]dioxino[2,3-j]quinolin-2-yl]methyl}amine;

{[(2S)-8-methyl-2,3-dihydro[1,4]dioxino[2,3-f]quinolin-2-yl]methyl}(1,2,3,4-tetrahydrodibenzo[b,d]thien-2-ylmethyl)amine;

{[(2S)-8-methyl-2,3-dihydro[1,4]dioxino[2,3-f]quinolin-2-yl]methyl}(1,2,3,4-tetrahydrodibenzo[b,d]thien-2-ylmethyl)amine;

N-({(3S)-6-trifluoromethoxy-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}ethanamine;

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}propan-1-amine;

(Cyclopropylmethyl) [(6-fluoro-2,3,4,9-tetrahydro-1H-carbazol-3-yl)methyl]{[(2S)-8-methyl-2,3-dihydro[1,4]dioxino[2,3-f]quinolin-2-yl]methyl}amine;

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclobutanamine;

N-{[(3R)-6-Fluoro-2,3,4,9-tetrahydro-1H-carbazol-3-yl]methyl}-N-{[(2S) dihydro[1,4]dioxino[2,3-f]quinolin-2-yl]methyl}propan-1-amine;

(Cyclopropylmethyl){[(3R)-6-fluoro-2,3,4,9-tetrahydro-1H-carbazol-3-yl]methyl}{[(2S) 8-methyl-2,3-dihydro[1,4]dioxino[2,3-f]quinolin-2-yl]methyl}amine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclobutanamine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}propan-2-amine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}butan-2-amine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclopentanamine;

N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclohexanamine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}propan-2-amine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}butan-2-amine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclopentanamine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclohexanamine;

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}propan-2-amine;

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclopentanamine;

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclohexanamine;

{[(3S)-6-Fluoro-9-methyl-2,3,4,9-tetrahydro-1H-carbazol-3-yl]methyl}methyl{[(2S)-8-methyl-2,3-dihydro[1,4]dioxino[2,3-f]quinolin-2-yl]methyl}amine;

{[(3R)-6-Fluoro-9-methyl-2,3,4,9-tetrahydro-1H-carbazol-3-yl]methyl}methyl {[(2S)-8-methyl-2,3-dihydro[1,4]dioxino[2,3-f]quinolin-2-yl]methyl}amine 5,6-Dichloro-2,3,4,9-tetrahydro-1H-carbazol-3-ylmethyl)-(8-methyl-2,3-dihydro-[1,4]dioxino[2,3-f]quinolin-2-ylmethyl)-amine;

(6-Chloro-2,3,4,9-tetrahydro-1H-carbazol-3-ylmethyl)-(8-methyl-2,3-dihydro-[1,4]dioxino[2,3-f]quinolin-2-ylmethyl)-amine;

(5-Chloro-6-fluoro-2,3,4,9-tetrahydro-1H-carbazol-3-ylmethyl)-(8-methyl-2,3-dihydro-[1,4]dioxino[2,3-f]quinolin-2-ylmethyl)-amine;

(7-Chloro-6-fluoro-2,3,4,9-tetrahydro-1H-carbazol-3-ylmethyl)-(8-methyl-2,3-dihydro-[1,4]dioxino[2,3-f]quinolin-2-ylmethyl)-amine;

(6-Chloro-2,3,4,9-tetrahydro-1H-carbazol-3-ylmethyl)-(8-methyl-2,3-dihydro-[1,4]dioxino[2,3-f]quinolin-2-ylmethyl)-amine;

(7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(S)-ylmethyl)-amine;

(7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(R)-ylmethyl)-amine;

(2,3-Dihydro-1,4-dioxa-5,8-diaza-phenanthren-3-(S)-ylmethyl)-(6-fluoro-2,3,4,9-tetrahydro-1H-carbazol-3-(R)-ylmethyl)-amine;

(2,3-Dihydro-1,4-dioxa-5,8-diaza-phenanthren-3-(S)-ylmethyl)-(6-fluoro-2,3,4,9-tetrahydro-1H-carbazol-3-(S)-ylmethyl)-amine;

(6-Fluoro-2,3,4,9-tetrahydro-1H-carbazol-3-(R)-ylmethyl)-(7-methyl-2,3-dihydro-1,4-dioxa-5,8-diaza-phenanthren-3-(S)-ylmethyl)-amine;

(6-Fluoro-2,3,4,9-tetrahydro-1H-carbazol-3-(S)-ylmethyl)-(7-methyl-2,3-dihydro-1,4-dioxa-5,8-diaza-phenanthren-3-(S)-ylmethyl)-amine;

(6-Fluoro-2,3,4,9-tetrahydro-1H-carbazol-3-(R)-ylmethyl)-(6-methyl-2,3-dihydro-1,4-dioxa-5,8-diaza-phenanthren-3-(S)-ylmethyl)-amine;

(6-Fluoro-2,3,4,9-tetrahydro-1H-carbazol-3-(S)-ylmethyl)-(6-methyl-2,3-dihydro-1,4-dioxa-5,8-diaza-phenanthren-3-(S)-ylmethyl)-amine;

{[(2R)-8-Fluoro-1,2,3,4-tetrahydrodibenzo[b,d]thien-2-yl]methyl}{[(2S)-8-methyl-2,3-dihydro[1,4]dioxino[2,3-f]quinolin-2-yl]methyl}amine;

{[(2S)-8-Fluoro-1,2,3,4-tetrahydrodibenzo[b,d]thien-2-yl]methyl}{[(2S)-8-methyl-2,3-dihydro[1,4]dioxino[2,3-f]quinolin-2-yl]methyl}amine;

{[(2S)-8-methyl-2,3-dihydro[1,4]dioxino[2,3-f]quinolin-2-yl]methyl}[(2S)-1,2,3,4-tetrahydrodibenzo[b,d]thien-2-ylmethyl]amine;

{[(2S)-8-methyl-2,3-dihydro[1,4]dioxino[2,3-f]quinolin-2-yl]methyl}[(2R)-1,2,3,4-tetrahydrodibenzo[b,d]thien-2-ylmethyl]amine;

{[(3R)-7-fluoro-1,2,3,4-tetrahydrodibenzo[b,d]thien-3-yl]methyl}{[(2S)-8-methyl-2,3-dihydro[1,4]dioxino[2,3-f]quinolin-2-yl]methyl}amine;

{[(3S)-7-fluoro-1,2,3,4-tetrahydrodibenzo[b,d]thien-3-yl]methyl}{[(2S)-8-methyl-2,3-dihydro[1,4]dioxino[2,3-f]quinolin-2-yl]methyl}amine;

N-{[(3S)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

(3R)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine;

(3S)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine;

[(2S)-2,3-dihydro[1,4]dioxino[2,3-f]quinolin-2-ylmethyl]{[(3S)-6-fluoro-2,3,4,9-tetrahydro-1H-carbazol-3-yl]methyl}amine;

[(2S)-2,3-dihydro[1,4]dioxino[2,3-f]quinolin-2-ylmethyl]{[(3R)-6-fluoro-2,3,4,9-tetrahydro-1H-carbazol-3-yl]methyl}amine;

[(2S)-8-methyl-2,3-dihydro[1,4]dioxino[2,3-f]quinolin-2-yl]methylamine;

{[(3S)-6-Fluoro-2,3,4,9-tetrahydro-1H-carbazole-3-carbazol-3-yl]methyl}amine;

1-(8-Fluoro-1,2,3,4-tetrahydrodibenzo[b,d]thien-2-ylmethyl)amine;

(1,2,3,4-tetrahydrodibenzo[b,d]thien-2-ylmethyl)amine;

2-(6-Fluoro-2,3,4,9-tetrahydro-1H-carbazol-3-yl)-ethylamine;

C-(6-Fluoro-2,3,4,9-tetrahydro-1H-carbazol-3-yl)-methylamine;

{[(3S)-6-fluoro-2,3,4,9-tetrahydro-1H-carbazol-3-yl]methyl}amine;

C-(6-Chloro-2,3,4,9-tetrahydro-1H-carbazol-3-yl)-methylamine;

C-(7-Chloro-6-fluoro-2,3,4,9-tetrahydro-1H-carbazol-3-yl)-methylamine;

C-(5-chloro-6-fluoro-2,3,4,9-tetrahydro-1H-carbazol-3-yl)-methylamine;

C-(6,7-dichloro-2,3,4,9-tetrahydro-1H-carbazol-3-yl)-methylamine;

C-(5,6-dichloro-2,3,4,9-tetrahydro-1H-carbazol-3-yl)-methylamine;

6-Fluoro-1,3,4,9-tetrahydrospiro[carbazole-2,2'-[1,3]dioxolane];

6-Fluoro-1,3,4,9-tetrahydro-2H-carbazol-2-one; and pharmaceutically acceptable salts thereof.

In one aspect, the present invention is directed to compositions comprising one or more compounds of formula I and one or more pharmaceutically acceptable carriers.

It has been found in accordance with the present invention that these derivatives act as serotonin modulators and thus find use in the treating, preventing, or ameliorating several diseases and disorders associated with binding to or antagonizing the $5\text{-}HT_{1A}$ receptors, including central nervous system diseases and disorders, such as depression (including, but not limited to major depressive disorder, childhood depression and dysthymia), anxiety, schizophrenia, panic disorder, post-traumatic stress disorder, premenstrual dysphoric disorder (also known as premenstrual syndrome), attention deficit disorder (with or without hyperactivity), obsessive-compulsive disorder, social anxiety disorder, generalized anxiety disorder, obesity, eating disorders such as anorexia nervosa and bulimia nervosa, vasomotor flushing, cocaine and alcohol addiction, sexual dysfunction, cognitive deficits resulting from neurodegenerative disorders like Alzheimer's disease, and related illnesses. This invention thus provides methods for modulating serotonin, as well as treating, preventing, or ameliorating such diseases and disorders. Such methods generally involve contacting the receptor with a compound of the invention, such as by administering to a patient suspected of suffering from or being susceptible to the disease or disorder an effective amount thereof.

In one aspect, the compounds of the present invention bind with high affinity to the $5\text{-}HT_{1A}$ transporter and are therefore useful in treating, preventing, or ameliorating diseases and disorders such as anxiety, depression, and schizophrenia. In another aspect, the compounds of the present invention exhibit lower affinity for the $5\text{-}HT_{1A}$ transporter and are therefore useful in treating, preventing, or ameliorating diseases and disorders such as cognitive deficits resulting from neurodegenerative disorders such as Alzheimer's disease.

In another embodiment of the present invention is provided processes for producing compounds of formula I. In one embodiment, the processes include preparing compounds of formula I:

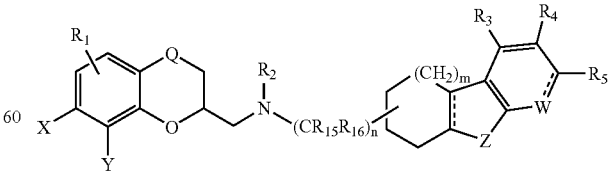

I or a pharmaceutically-acceptable salt thereof;

wherein:

$R_1$, $R_3$, $R_4$, and $R_5$ are independently hydrogen, halo, cyano, carboxamido, carboalkoxy, trifluoromethyl, alkyl, $OR_9$, trifluoromethoxy, alkanoyl, alkanoyloxy, amino, monoalkylamino, dialkylamino, alkanamido, alkanesulfonyl, alkanesulfonamido, or phenyl;

W is N, NR$_6$, or CR$_6$;

R$_6$ is hydrogen, halo, cyano, carboxamido, carboalkoxy, trifluoromethyl, alkyl, OR$_9$, trifluoromethoxy, alkanoyl, alkanoyloxy, amino, monoalkylamino, dialkylamino, alkanamido, alkanesulfonyl, alkanesulfonamido, or phenyl;

R$_2$ is hydrogen, alkyl, cycloalkyl, CH$_2$cycloalkyl, or benzyl;

X and Y are independently hydrogen, halo, hydroxy, cyano, carboxamido, carboalkoxy, trifluoromethyl, alkyl, alkoxy, alkanoyl, alkanoyloxy, amino, monoalkylamino, dialkylamino, alkanamido, alkanesulfonyl, alkanesulfonamido, phenyl, X and Y together with the atoms to which they are attached, form —N=C(R$_7$)C(R$_8$)=N—, —N=C(R$_7$)C(R$_9$)=CH—, —N=C(R$_7$)N=C(R$_9$)—, —CH=C(R$_7$)C(R$_9$)=CH—, —N=C(R$_{10}$)O—, —NH—C(R$_{11}$)=CH—, NH—C(R$_{17}$)O—, =N—O—C(R$_{18}$)=, —NH—N—C(R$_{18}$)—, —NH—(CR$_{17}$)=N—, —NH—C(R$_{10}$)=CH—, —O—C(=O)C(R$_9$)—, —O—C(R$_7$)C(R$_9$)—, —O—C(=O)—NR$_9$—, —O—C(R$_9$)=CH—, —O—N=C(R$_9$)—, or —O—C(R$_9$)=N;

R$_7$ and R$_8$ are independently hydrogen, halo, amino, monoalkylamino, dialkylamino, or alkyl;

R$_9$ is hydrogen or alkyl;

R$_{10}$ is hydrogen, halo, trifluoromethyl, pentafluoroethyl, amino, monoalkylamino, dialkylamino, alkoxy or alkyl;

R$_{11}$ is hydrogen, halo, trifluoromethyl, pentafluoroethyl, or alkyl;

Z is N(R$_{12}$), O, S, or C(R$_{13}$R$_{14}$);

R$_{12}$, R$_{13}$ and R$_{14}$ are independently hydrogen or alkyl;

R$_{15}$ and R$_{16}$ are independently at each occurrence, H or C$_1$-C$_3$ alkyl;

R$_{17}$ is hydrogen, halo, cyano, carboxamido, carboalkoxy, trifluoromethyl, alkyl, alkanoyloxy, amino, monoalkylamino, dialkylamino, alkanamido, or alkanesulfonamido;

R$_{18}$ is hydrogen, carboxy, cyano, carboxamido, carboalkoxy, trifluoromethyl, amino, monoalkylamino, dialkylamino, monoalkylamino, dialkylamino, alkoxy, or alkyl;

Q is O, S, or CH$_2$;

a dotted line represents an optional double bond; and n and m are independently integers of 0, 1, 2 or 3;

comprising:
by condensing a compound of formula III:

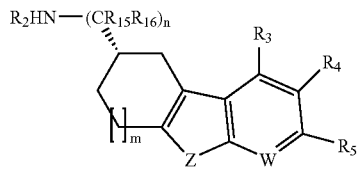

III with a compound of formula A:

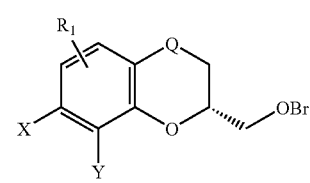

A to produce a compound of formula I.

In one embodiment, the compound of formula I is S,S-(6-fluoro-2,3,4,9-tetrahydro-1H-carbazol-3-ylmethyl)-(8-methyl-2,3-dihydro-[1,4]dioxino[2,3-f]quinolin-2ylm-ethyl)-amine; the compound of formula III is {[(3S)-6-fluoro-2,3,4,9-tetrahydro-1H-carbazol-3-yl]methyl}amine; and the compound of formula A is [(2R)-8-methyl-2,3-dihydro[1,4]dioxino[2,3-f]quinolin-2-yl]methyl 4-bromobenzenesulfonate.

In another embodiment, processes for preparing compounds of formula I further include preparing a compound of formula III by a process comprising:
reducing a compound of formula IV:

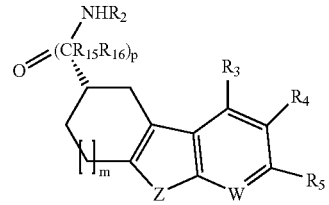

IV where p is 0, 1, or 2,
with lithium aluminum hydride in the presence of tetrahydrofuran.

In one embodiment, the compound of formula IV is (3S)-6-fluoro-2,3,4,9-tetrahydro-1H-carbazole-3-carboxamide.

In another embodiment, processes for preparing compounds of formula I further include preparing a compound of formula IV by a process comprising:
reacting a compound of formula V:

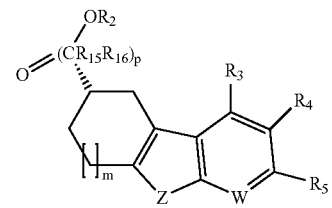

V with
1) methylene chloride and oxalyl chloride; and
2) acetone and ammonia.

In one embodiment, the compound of formula V is (3S)-6-fluoro-2,3,4,9-tetrahydro-1H-carbazole-3-carboxylic acid.

In another embodiment, processes for preparing compounds of formula I further include preparing a compound of formula V by a process comprising:
a. combining racemic compound of formula VI:

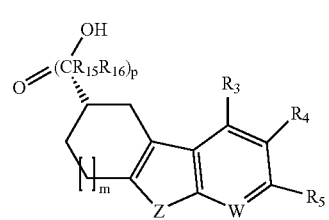

VI with acetonitrile and a first optically active base to form a first solution;
b. incubating said first solution for a first period of time to form first crystals;
c. separating said first crystals from the mother liquor;
d. combining said mother liquor with a second optically active base to form a second solution;
e. incubating said second solution for a second period of time to form second crystals, wherein said second crystals; and
f. converting said second crystals to a compound of formula V.

In one embodiment, the compound of formula VI is 6-fluoro-2,3,4,9-tetrahydro-1H-carbazole-3-carboxylic acid. The first optically active base can be (−)-cinchonidine. The second optically active base can be (+)-pseudoephedrine.

In another embodiment, processes for preparing compounds of formula I further include preparing a compound of formula VI by a process comprising:
hydrolyzing a compound of formula VII:

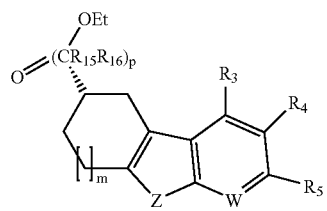

VII in an alcohol and base.

In one embodiment, the compound of formula VII is 6-fluoro-2,3,4,9-tetrahydro-1H-carbazole-3-carboxylic acid ethyl ester.

In another embodiment, processes for preparing compounds of formula I further include a process for preparing a compound of formula VII comprising:
refluxing a compound of formula VIII:

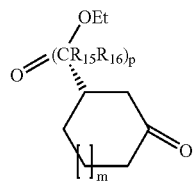

VIII and compound of formula IX:

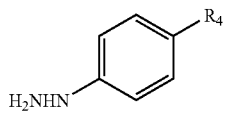

IX in an alcohol.

DETAILED DESCRIPTION OF ILLUSTRATIVE EMBODIMENTS

The term "alkyl", as used herein, whether used alone or as part of another group, refers to an aliphatic hydrocarbon chain and includes, but is not limited to, straight and branched chains having 1 to 6 carbon atoms unless otherwise specified. For example, methyl, ethyl, n-propyl, iso-propyl, and 2-methylpropyl are encompassed by the term "alkyl". Specifically included within the definition of "alkyl" are those aliphatic hydrocarbon chains that are optionally substituted, including unsubstituted and mono-, di- and tri-substituted hydrocarbon groups. Suitable substitutions include, for example, halogen substituents, including but not limited to fluoro, chloro, and bromo, and the like, and alkoxy subtituents, including OH, —O—R—, and the like.

Carbon number, as used in the definitions herein, refers to carbon backbone and carbon branching, but does not include carbon atoms of substituents, such as alkoxy substitutions and the like.

The term "alkoxy", as used herein, whether used alone or as part of another group, refers to a substituted or unsubstituted —O—R group having 1 to 6 carbon atoms, where R is an alkyl group as defined above.

The term "alkanoyl", as used herein, whether used alone or as part of another group, refers to a substituted or unsubstituted R—C(=O)— group having 2 to 6 carbon atoms, where R is an alkyl group as defined above.

The term "halo", as used herein, includes to bromine, chlorine, fluorine, and iodine.

The term "cycloalkyl", as used herein, refers to a saturated or partially saturated hydrocarbon ring containing 3 to 8 carbon atoms and more preferably 5 to 7 carbon atoms. Cycloalkyl groups may be monocyclic or bicyclic, and more preferably monocyclic. Bicyclic cycloalkyl groups are preferably bridged. "Bridged" refers to a cycloalkyl group that contains at least one carbon-carbon bond between two non-adjacent carbon atoms of the cycloalkyl ring. "Partially saturated" refers to a non-aromatic cycloalkyl group containing at least one double bond and preferably one double bond. Preferably, the cycloalkyl group is saturated. The cycloalkyl group may be unsubstituted or substituted.

The term "alkanamido", as used herein, refers to the group R—C(=O)—NH— where R is an alkyl group of 2 to 6 carbon atoms.

The term "alkanoyloxy", as used herein, refers to the group R—C(=O)—O— where R is an alkyl group of 2 to 6 carbon atoms.

The term "alkanesulfonamido", as used herein, refers to the group R—S(O)$_2$—NH— where R is an alkyl group of 2 to 6 carbon atoms.

The terms "monoalkylamino" and "dialkylamino", as used herein, respectively refer to —NHR and —NRR$_a$, where R and R$_a$ are independently selected from an alkyl group of 1 to 6 carbon atoms.

The term "carboxamido", as used herein, refers to the group NH$_2$—C(=O)—.

The term "carboalkoxy", as used herein, refers to the group R—O—C(=O)—, where R is an alkyl group of 2 to 6 carbon atoms.

The term "alkanesulfonyl", as used herein, refers to the group R—S(=O)$_2$— where R is an alkyl group of 1 to 6 carbons.

The term "alkanesulfonamido", as used herein, refers to the group R—S(O)$_2$—NH— where R is an alkyl group of 1 to 6 carbons.

The term "phenyl" includes phenyl groups that are optionally substituted with suitable substituents including, for example, alkyl, halogen (including, but not limited to fluoro, chloro, and bromo), alkoxy groups (including OH and —O—R— groups and the like), and cyano groups.

The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Salts of the present invention can be crystalline and may exist as more than one polymorphs. Each polymorph forms another aspect of the invention. Solvates, hydrates, and anhydrous forms of the salt are also encompassed by the invention.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

Prodrugs of the compounds of Formula I are also embraced by the present invention. The term "prodrug", as used herein, means a compound which is convertible in vivo by metabolic means (e.g. by hydrolysis) to a compound of formula I. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

The term "effective amount" refers to an amount of a compound as described herein that is able to produce a stated result. For example, the term "effective amount" when used with respect to a particular disease or disorder can refer to an amount that is effective to at least partially inhibit, prevent, treat, or modulate the symptoms of that disease or disorder. Such diseases and disorders include, but are not limited to, those associated with 5-$HT_{1A}$ antagonism. This can include, for example, contacting cells, tissues, or receptors with compounds of the present invention. Thus, for example, the term "effective amount", when used in connection with 5-$HT_{1A}$ antagonists, for example, for the treatment of depression, refers to the treatment and/or prevention and/or amelioration of the condition.

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%.

Compounds of this invention may be prepared, for example, according to Schemes 1, 2, 3, 6, 7, 8, 9, 10 or 11 where the R groups and other groups are as defined in Formula I. As shown in Scheme 1, a benzodioxane or derivative containing a leaving group, such as a brosylate or a tosylate, is allowed to react with an azide, such as sodium azide, in a polar solvent, such as dimethylformamide (DMF) at room temperature, or with heating from about 50° C. to about 150° C., to give the corresponding organic azide-containing compound. The azide-containing compound is reduced to the corresponding amine under a hydrogen atmosphere in the presence of a catalyst, such as Pd on charcoal. Alternatively, the azide may be reduced to the corresponding amine by triphenylphosphine in a solvent such as tetrahydrofuran containing water. The corresponding amine is coupled to a carboxylic acid of this invention in the presence of a coupling agent, such as dicyclohexylcarbodiimide (DCC) in the presence of 1-hydroxybenzotriazole (HOBT) in an organic solvent, such as tetrahydrofuran (THF), containing a base, such as triethylamine, at a temperature from about 15-45° C. to give the corresponding amide which is reduced with a reducing agent, such as lithium aluminum hydride (LAH), to give compounds of this invention. The compounds of this invention can be allowed to react further with aldehydes in the presence of a reducing reagent, such as sodium cyanoborohydride, in the presence of a solvent, such as glacial acetic acid to give compounds substituted by $R_2$, which are also compounds of this invention.

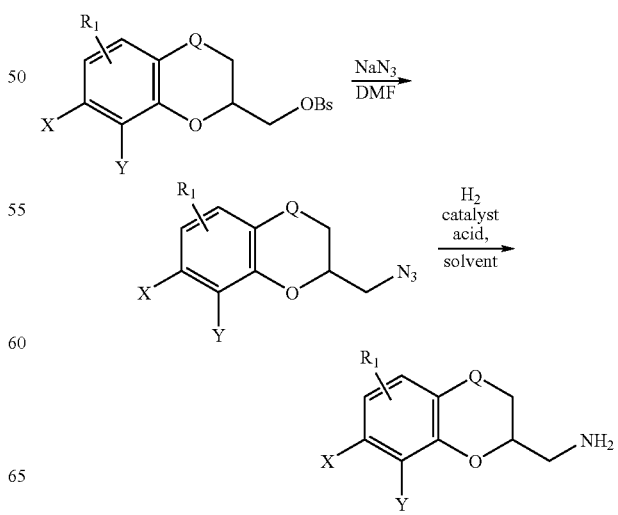

Scheme 1

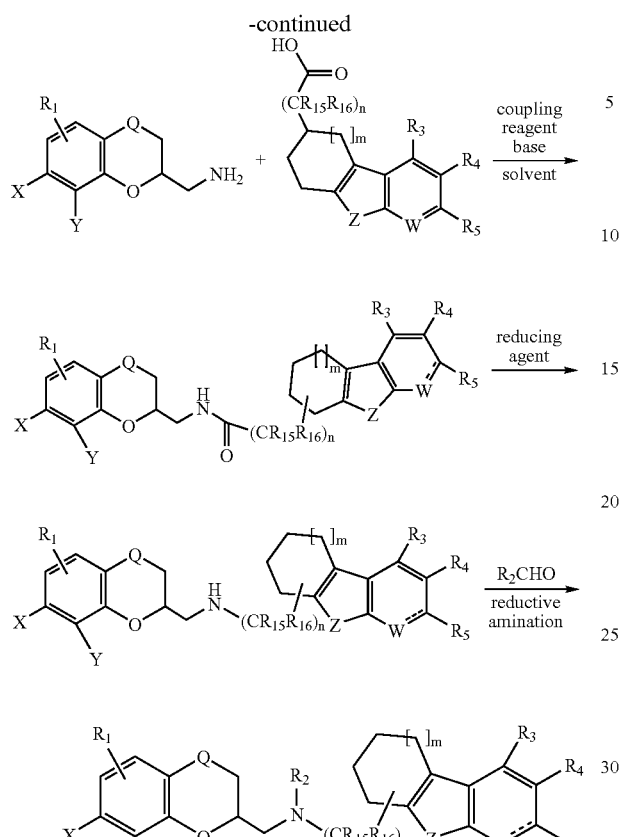

According to Scheme 2, aminomethylbenzodioxane derivatives are allowed to react with aldehydes of this invention in the presence of a reducing agent, such as sodium cyanoborohydride, in the presence of a solvent, such as acetic acid, to give compounds of this invention. A second reductive amination also gives additional compounds of this invention where $R_2$ is as defined in the generic structure.

Scheme 2

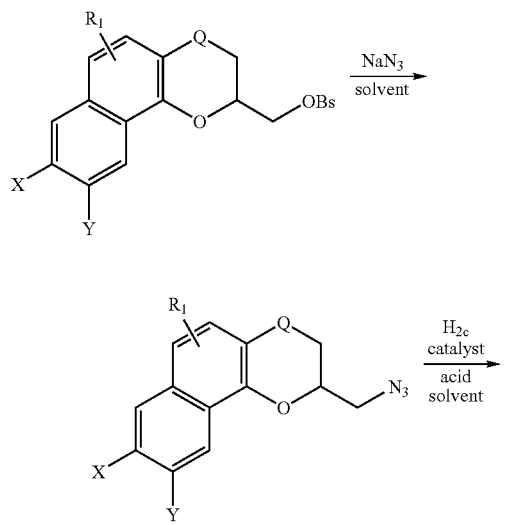

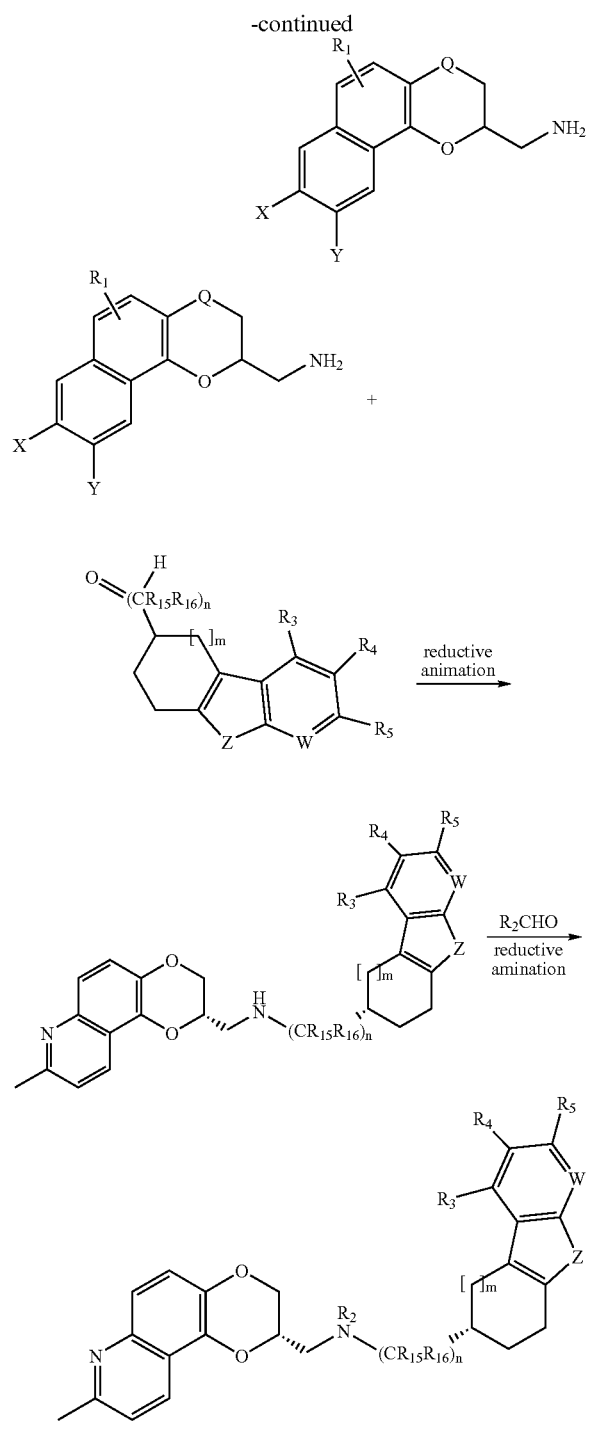

Compounds of this invention may also be prepared according to Scheme 3 in which an ester of this invention is converted to the corresponding acid of this invention. The acid of this invention is converted to the corresponding amide by treatment with ammonia in the presence of a solvent, such as THF, in the presence of a coupling reagent, such as carbonyl diimidazole (CDI). Alternatively, the acid of this invention is converted to the corresponding amide by first converting to an acid halide using reagent such as oxalyl chloride followed by ammonium hydroxide treatment. Chiral acid is obtained from resolution using a chiral amine such as (−) cinchonidine. The amides of this invention are treated with a reducing agent, such as diborane in THF or LAH, to give alkylamines of this invention. The alkylamines are allowed to react with benzodioxane methylbrosylate derivatives of this invention to give compounds of this invention. The compounds of this invention may be further substituted by a reductive amination reaction as described above.

Scheme 3

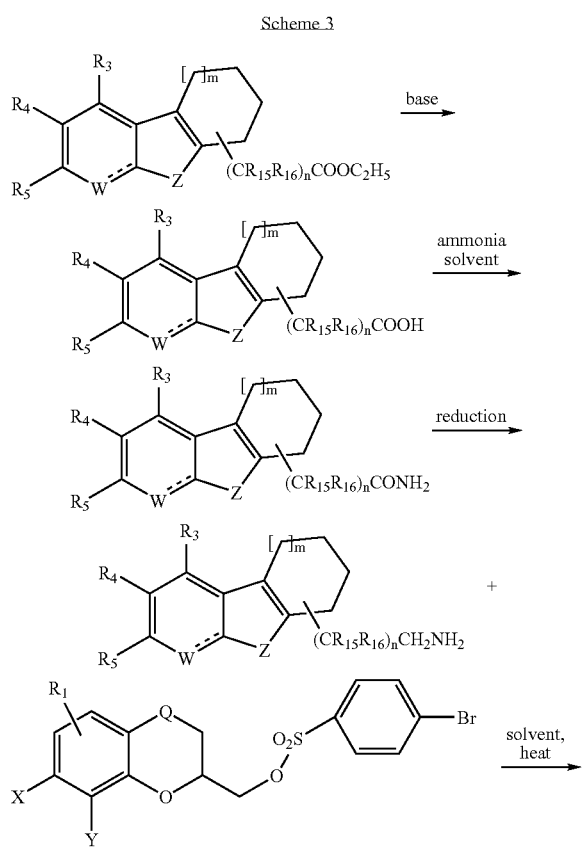

Synthetic intermediates useful for preparing compounds of this invention may be prepared according to Scheme 4 in which a substituted phenyl compound, where the groups are defined in the generic structure, is allowed to react with a bromocycloalkyl ester in the presence of a base, such as lithium diisopropylamide (LDA), in a solvent, such as THF, to give a keto ester intermediate which is converted to intermediates of this invention with a dehydrating agent, such as polyphosphoric acid (PPA).

Scheme 4

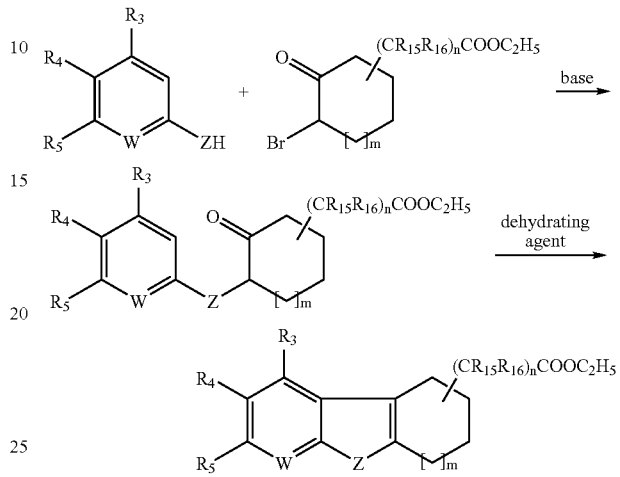

Certain synthetic intermediates of this invention may be prepared according to Scheme 5 in which cycloalkanones containing carboxylic esters are allowed to react with 1-bromo-2-bromomethylbenzene in the presence of a base, such as LDA, in a solvent, such as THF, followed by reaction with a Cr(II)/Ni(II) reagent, such as $CrCl_2$ (cat. $NiCl_2$), in an organic solvent, such as DMF, to give the corresponding tricyclic hydroxy intermediate. The tricyclic hydroxy intermediate is dehydrated to the intermediates of this invention using a reagent, such as p-toluenesulfonic acid, in a refluxing solvent, such as benzene. [See R. L. Halterman; C. Zhu, *Tetrahedron Letters*, (1999), 40, 7445-7448].

Scheme 5

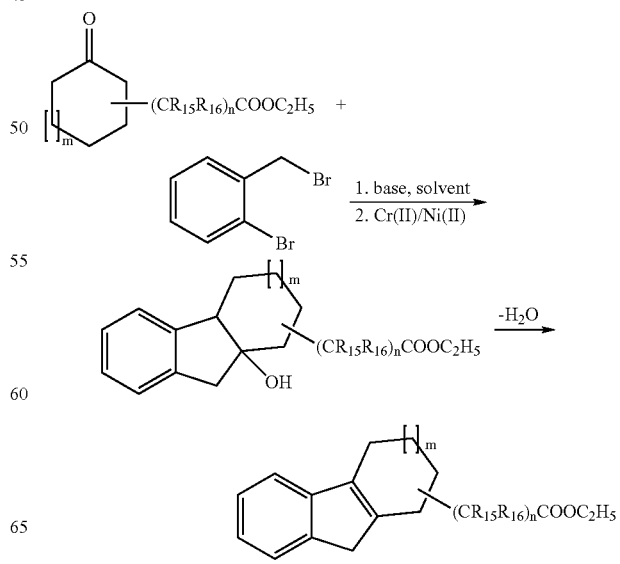

Compounds of the invention can alternatively be prepared according to Scheme 6. Intermediate 6/16 can be prepared by at least two procedures, as illustrated below. That intermediate is then reacted with a base, such as KOH, in the presence of a solvent, such as EtOH. This reaction is then followed a second reaction in oxayl chloride and NH₃, which is then reduced in the presence of, for example, LAH, to yield intermediate 12/19. Intermediate 12/19 is then combined with [(2R)-8-methyl-2,3-dihydro[1,4]dioxino[2,3-f]quinolin-2-yl]methyl 4-bromobenzenesulfonate, (synthesized according to a procedure described in U.S. Pat. No. 6,693,197B1) to produce compounds of formula I.

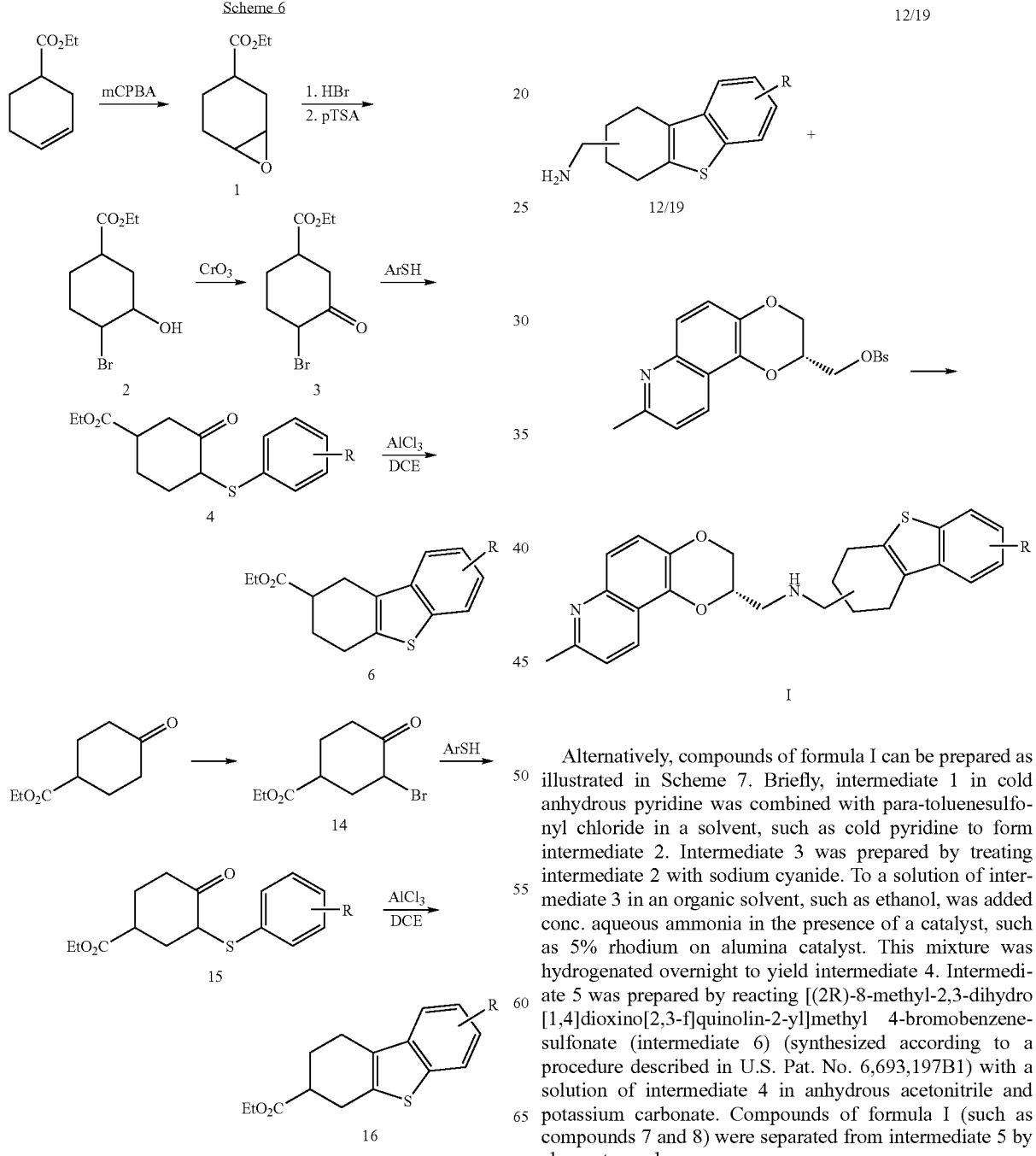

Alternatively, compounds of formula I can be prepared as illustrated in Scheme 7. Briefly, intermediate 1 in cold anhydrous pyridine was combined with para-toluenesulfonyl chloride in a solvent, such as cold pyridine to form intermediate 2. Intermediate 3 was prepared by treating intermediate 2 with sodium cyanide. To a solution of intermediate 3 in an organic solvent, such as ethanol, was added conc. aqueous ammonia in the presence of a catalyst, such as 5% rhodium on alumina catalyst. This mixture was hydrogenated overnight to yield intermediate 4. Intermediate 5 was prepared by reacting [(2R)-8-methyl-2,3-dihydro[1,4]dioxino[2,3-f]quinolin-2-yl]methyl 4-bromobenzenesulfonate (intermediate 6) (synthesized according to a procedure described in U.S. Pat. No. 6,693,197B1) with a solution of intermediate 4 in anhydrous acetonitrile and potassium carbonate. Compounds of formula I (such as compounds 7 and 8) were separated from intermediate 5 by chromatography.

Scheme 7

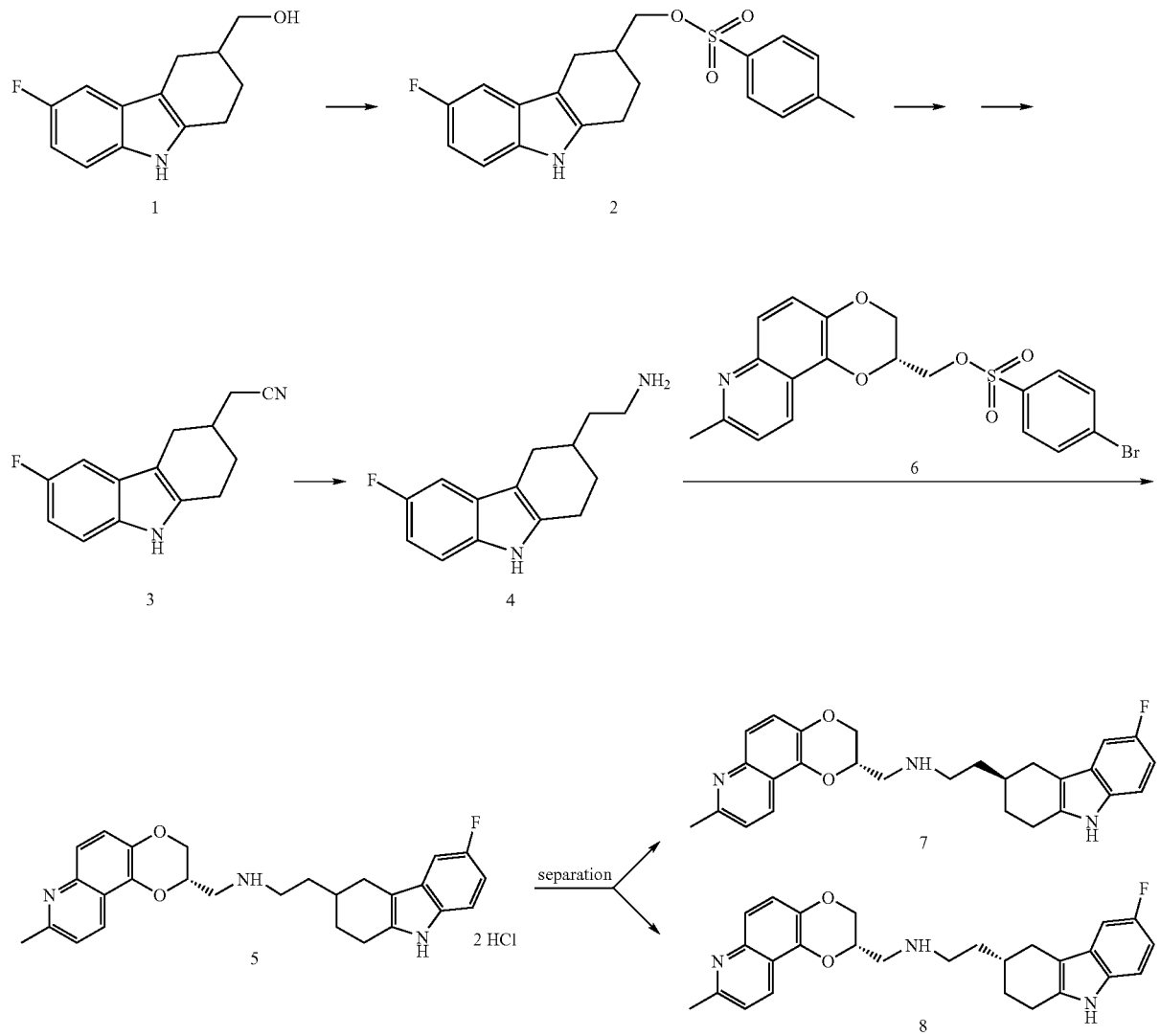

Scheme 8 illustrates an alternative synthetic route for preparing compounds of formula I. For example, compound 14 was prepared by a modification of published procedures. (See M. S. Berridge et al., Nucl. Med. Biol. 19 (5) 563-569 (1992); Brueckner R. et al., EP 1 424 337 A1 (2004)). (Compound 22 can be prepared similarly, by generally following a published protocol by Brueckner, R., et al., EP Patent No. 1 424 337 A1). First, cyclohexane-1,3-dione was reacted with an appropriately substituted phenylhydrazine to provide intermediate 9.

Intermediate 10 was then prepared by generally following a published protocol (See R. F. Borch et al., J. Org. Chem. 38 (15), 2729 (1973); Nader G. et al., French Patent 2729141 (1996)) by heating a mixture of intermediate 9, diethylene glycol and para-toluene sulfonic acid monohydrate in an aprotic solvent such as toluene. Deprotection of the ethylene ketal 10 by treatment with 10% aqueous sulfuric acid in a solvent such as methanol, provided the intermediate ketone 11. Intermediate 11 was in turn, converted to the corresponding oxime 12. The crude intermediate 12 underwent reduction to the desired amine 13 with Al—Ni alloy in ethanol and aqueous sodium hydroxide. Condensation of intermediate 13 with [{2R)-8-methyl-2,3-dihydro[1,4-dioxino[2,3-f] quinolin-2-yl]methyl 4-bromobenzenesulfonate (synthesized according to a procedure described in U.S. Pat. No. 6,693,197B1) in a solvent such as acetonitrile and in the presence of a base such as potassium carbonate provided compound 14 as the free base. The latter was converted then to compound 14 as the dihydrochloride salt (mixture of diastereomers).

Compounds 15 and 16 were then prepared from compound 14 by chromatographic separation. The mixture of diastereomers 14 was separated by chromatography. The fractions corresponding to peak 1 provided the compound 15 as free base. The other diastereoisomer isolated using the same method (corresponding to peak 2) was compound 16 (free base). The free base was then converted to the dihydrochloride salt.

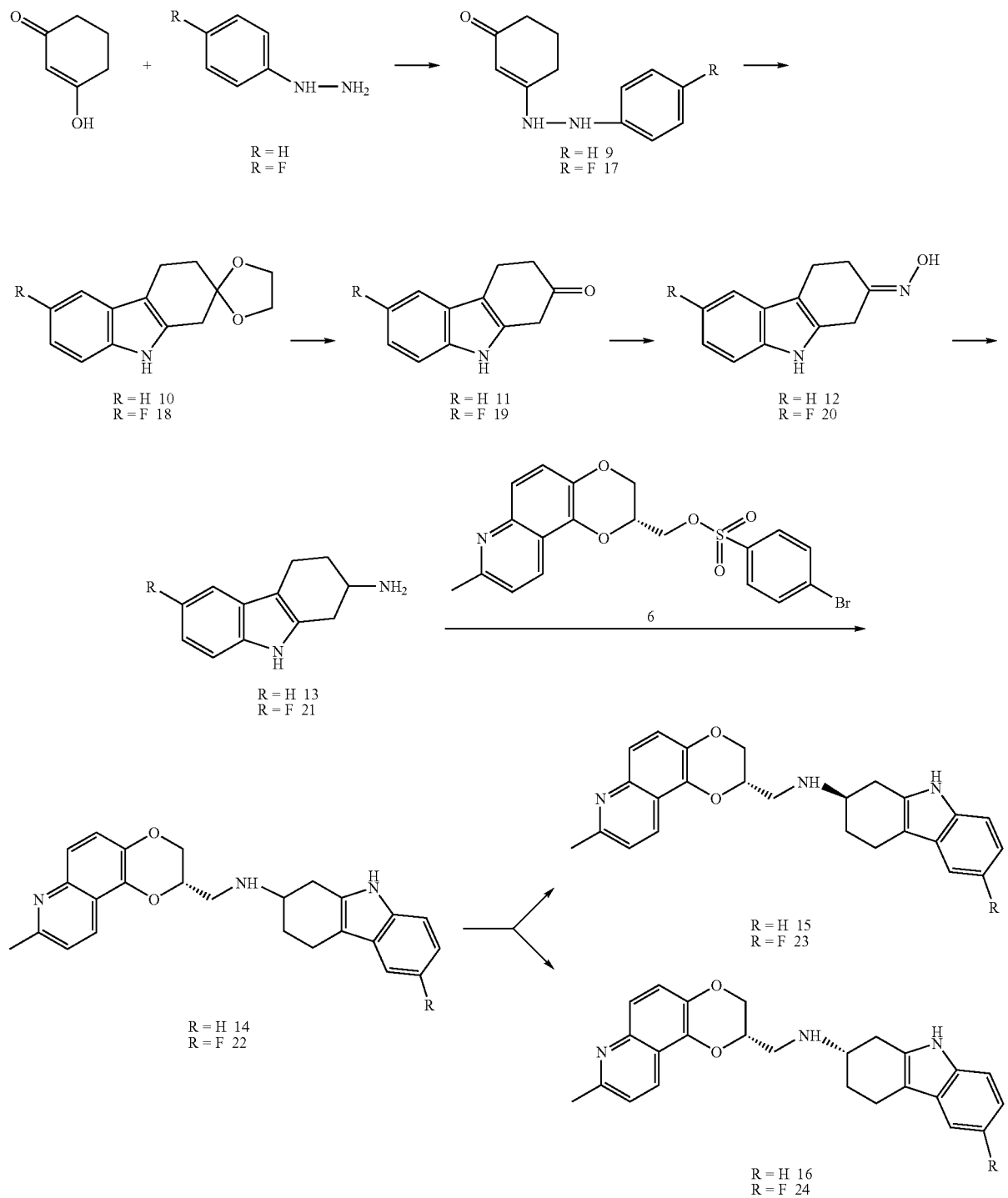

Scheme 9 illustrates another useful for the preparation of compounds of formula I. Briefly, a condensation reaction between aldehyde 1, methyl nitroacetate 2, and diethylamine hydrochloride, in refluxing toluene, can give the corresponding nitrocoumarin 3. [Dauzonne, D., and Royer, R., *Synthesis*, 836-37 (1983)]. Nitrocoumarin 3 can then treated with a diene, which should yield Diels-Alder product 4, which, after treatment with CTABr and NaOH, followed by treatment with 3.75 M $H_2SO_4$, can afford benzofuran compound 5. [Amantini, D., et al., *J. Org. Chem.*, 68:9263-68 (2003)]. Benzofuran compound 5 can then be converted to compound 6 using known chemistry, and then coupled with the broyslate 7 to afford the desired compound 8 as a mixture of diastereomers.

Scheme 9

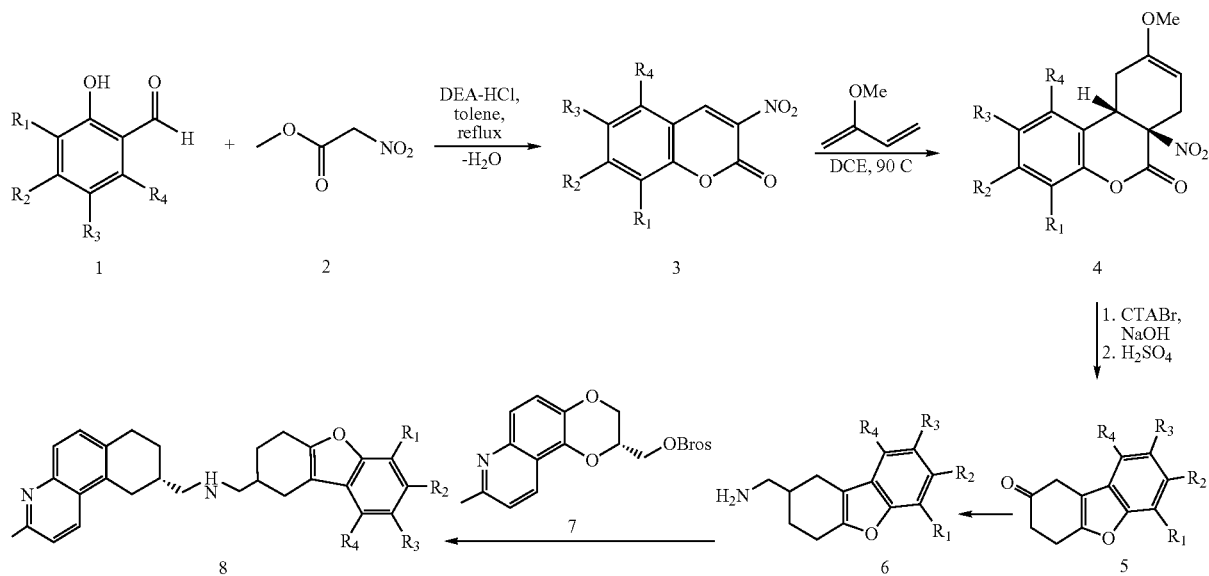

Preferred compounds of this invention can alternatively be synthesized as illustrated in Scheme 10. First, condensation of cyclohexanone 4-ethylcarboxylate with fluorophenylhydrazine is performed by refluxing the two compounds in ethanol. Second, hydrolysis of the ester to the acid is performed using a base, such as aqueous sodium hydroxide or anhydrous potassium hydroxide, in ethanol. The resulting ethanol solution is treated with 1N aqueous HCl, the ethanol evaporated, and the acid (e.g., 6-fluoro-2,3,4,9-tetrahydro-1H-carbazole-3-carboxylic acid) crystallizes out upon concentration. A 0.1M solution of this racemic acid is then made and mixed in a 1:1 ratio with an optically active base, such as (−)-cinchonidine in acetonitrile. This mixture is left in an open vial for 48 hours. Crystals form slowly.

The mother liquid from the optically active base salt containing the S-enantiomer is mixed in a 4:1 ratio with the R-enantiomer in the presence of second optically active base, such as (+)-pseudoephedrine. Crystals again form slowly. Chiral HPLC shows substantial purity of the S-enantiomer.

Next, the S-enantiomer acid is converted to an amide. First, the acid is converted to the acid chloride using oxalyl chloride at room temperature. The solvent is evaporated at low temperature and low pressure. Ammonolysis of the acid chloride is then accomplished using aqueous ammonia or dioxane. The amide is recovered as a crystal from the acetone/water mixture. The aqueous ammonia produces an exotherm, and should be maintained at 5-10° C., to avoid excessive hydrolysis. For this purpose, the acid chloride is sufficiently diluted with acetone, and the mixture cooled down to 0-5° C. before the fast addition of aqueous ammonia. The amide is then reduced to the amine, in THF with lithium aluminum hydride at reflux. The reaction is quenched at the cold with the saturated aqueous solution of the Rochelle salt (sodium potassium tartrate). The amide is then condensed with the brosylate, dimethylaminopyridine, and excess amine in DMSO. The reaction mixture is quenched with aqueous sodium bicarbonate, and the product extracted with methylene chloride.

Scheme 10

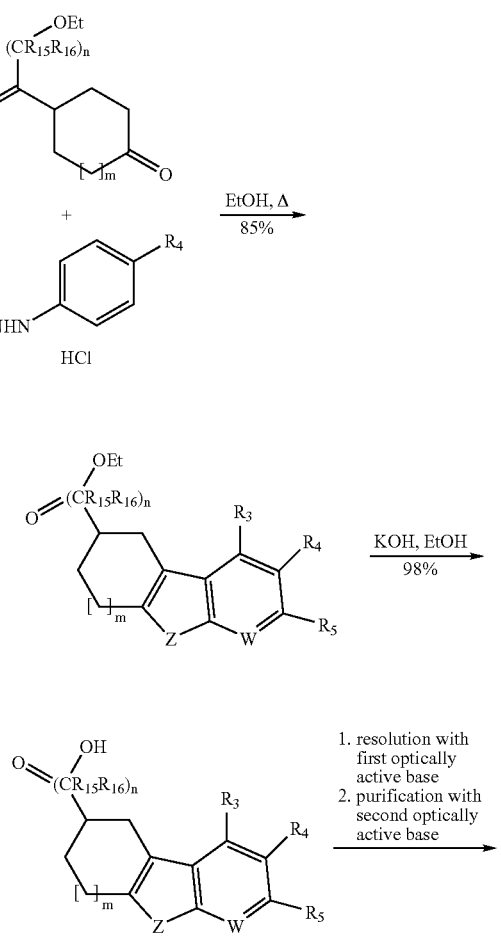

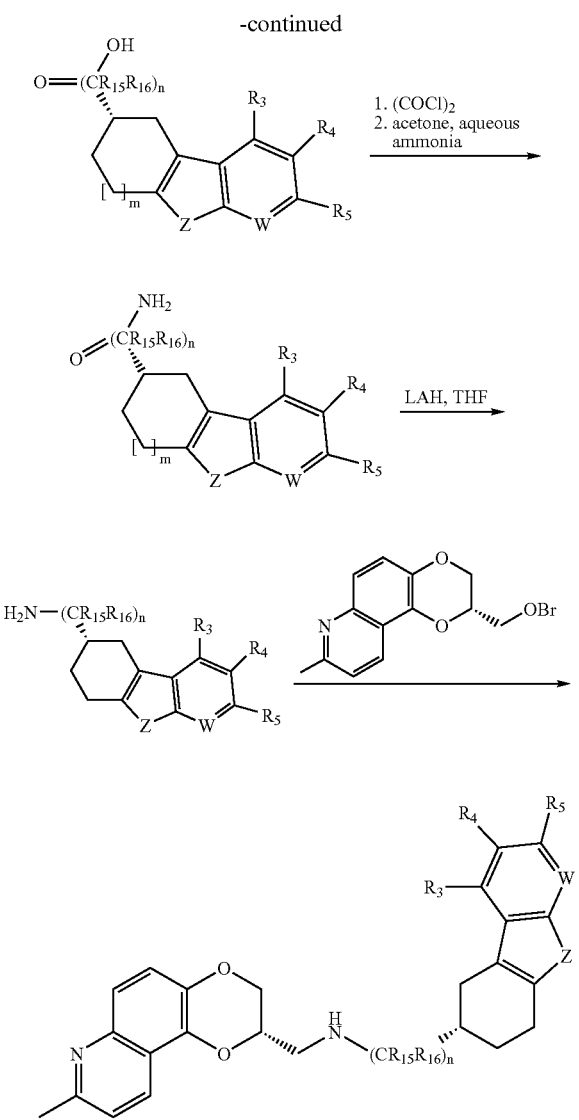

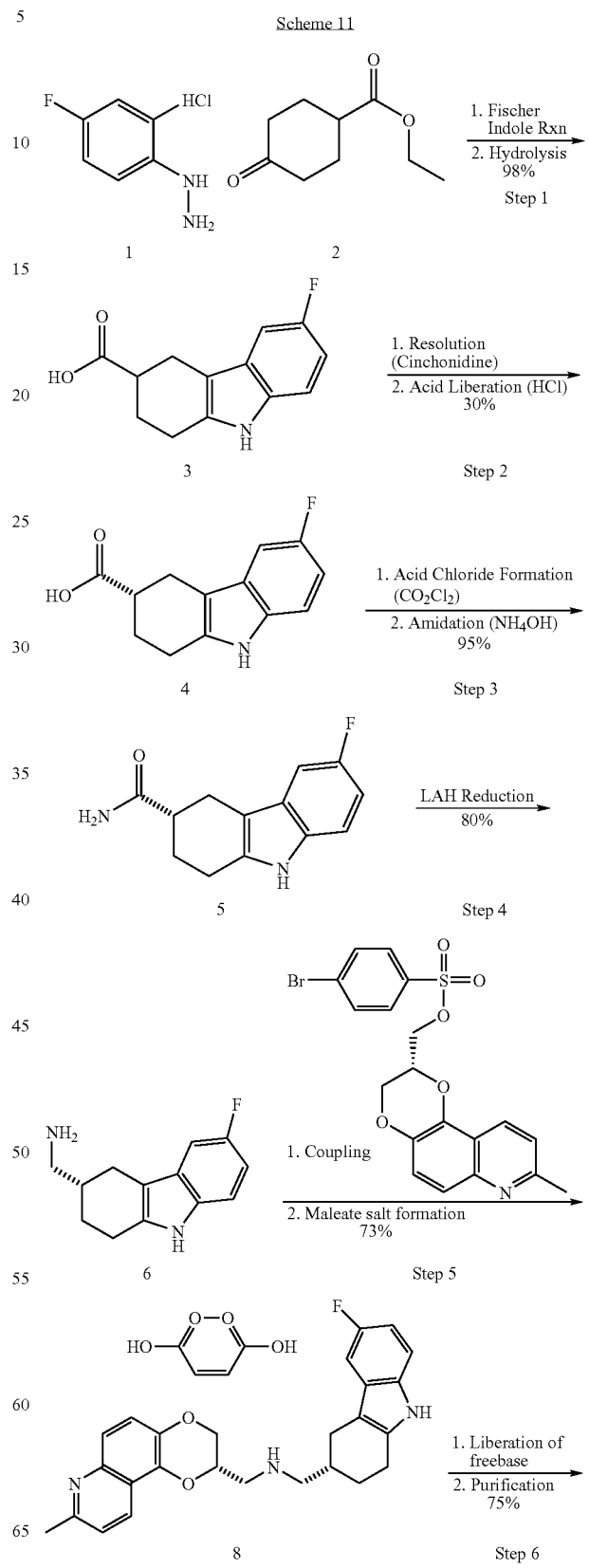

maleic acid salt 8. Finally, the maleic acid salt 8 is liberated, followed by recrystallization of compound 9 in 75% yield.

Scheme 11 illustrates a procedure amenable to large-scale production of compounds of formula I. The route improves yields and eases operation by concatenation of steps, allows for the resolution of racemic indole acid 3 using a single chiral base (e.g., cinchonidine), and allows for the purification of compounds of formula I via crystalline salt (e.g., maleate salt) formation.

The first step is a Fisher indole reaction of the ketoester 1 with hydrazine HCl followed by hydrolysis of the resulting ester to the racemic indole acid 3 in 97% yield. The chiral resolution of indole acid 3 is accomplished using cinchonidine in isopropanol followed by liberation of the eutomer salt to the desired free indole acid 4. This process gives >97% enantiomeric excess of resolved indole acid in 60% overall yield based on the eutomer. Indole acid 4 is converted to the acid chloride in Step 3 and subsequently treated with aqueous ammonium hydroxide to provide amide 5 in 95% yield. Indole amide 5 is reduced with lithium aluminum hydride in THF in 80% yield to provide amine 6. In Step 5, the amine 6 is coupled with quinaldine brosylate 7 (synthesized according to a procedure described in U.S. Pat. No. 6,693,197B1). The resultant compound is isolated as the -continued

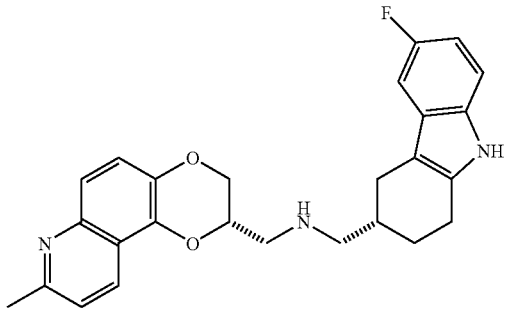

9

The present invention also provides pharmaceutical compositions comprising at least one compound of formula I; and optionally one or more pharmaceutically acceptable carriers, excipients, or diluents. Examples of such carriers are well known to those skilled in the art and are prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, preferably from 10 to 25 mg, and may be given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The present compounds are further described in the following examples.

EXAMPLES

Example 1

N-[(6-fluoro-2,3,4,9-tetrahydro-1H-carbazol-2-yl)methyl]-N-{[(2S)-8-methyl-2,3-dihydro[1,4]dioxino[2,3-f]quinolin-2-yl]methyl}amine 6-Fluoro-2,3,4,9-tetrahydro-1H-carbazole-2-carboxylic acid (I)

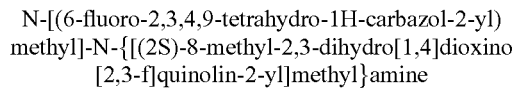

4-fluorophenyhydrazine (0.90 g, 7.14 mmol) was dissolved in glacial acetic acid (25 mL) under a nitrogen atmosphere and added dropwise to a refluxing solution of 3-cyclohexanonecarboxylic acid ethyl ester (1.73 g, 10 mmol) dissolved in glacial acetic acid (15 mL). After the addition was complete, the solution was heated under reflux for 1 hr, cooled to room temperature and allowed to stir overnight. The orange solution was evaporated under reduced pressure to give a yellow-brown solid. The solid was suspended in 10% sulfuric acid and heated under reflux for 5 hrs, cooled to room temperature and allowed to stir overnight. The brown solid was collected by filtration and recrystallized from acetic acid and water to give the compound I (1.21 g), mp: >200° C. MS [M–H]⁻ m/z 232.

[(2S)-8-methyl-2,3-dihydro[1.4]dioxino[2,3-f]quinolin-2-yl]methylamine

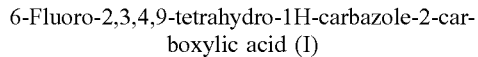

A solution of [(2R)-8-methyl-2,3-dihydro[1,4]dioxino[2,3-f]quinolin-2-yl]methyl 4-bromobenzenesulfonate (900 mg, 2.0 mmol) and sodium azide (65 mg, 10 mmol) in dimethylformamide (DMF, 20 mL) was heated at 80° C. for 4 hr. The solvent was evaporated under reduced pressure and replaced with methylene chloride (200 mL). The organic solution was washed sequentially with water and saturated aqueous sodium chloride solution. The organic phase was dried (Na₂SO₄) and evaporated to give the azide (490 mg) as a yellow oil.

The azide (470 mg, 1.8 mmol) was dissolved in methanol (100 mL), treated with 10% Pd on charcoal (0.30 g) and conc. HCl (1.0 mL) and hydrogenated at 60 psi overnight. The reaction mixture was filtered through Celite and concentrated under reduced pressure. The yellow solid residue was recrystallized from ethanol to give the title compound as the hydrochloride salt (0.18 g), mp >250° C.

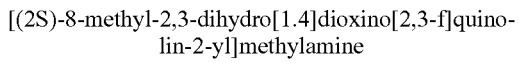

6-fluoro-N-{[(2S)-8-methyl-2,3-dihydro[1,4]dioxino [2,3-f]quinolin-2-yl]methyl}-2,3,4,9-tetrahydro-1H-carbazole-2-carboxamide (II)

[(2S)-8-methyl-2,3-dihydro[1,4]dioxino[2,3-f]quinolin-2-yl]methylamine hydrochloride (360 mg, 1.35 mmol) and compound I were suspended in anhydrous tetrahydrofuran (THF) containing triethylamine (1.8 mL) and HOBT (54 mg) with stirring for 15 min. The coupling reagent, DCC (300 mg) was added and stirring was continued overnight. The reaction mixture was filtered and the filtrate was diluted with water and extracted with ether. The ether layers were combined, dried ($MgSO_4$), and evaporated under reduced pressure to give a residue which was purified by flash chromatography on silica gel eluting with 1-2% methanol in methylene chloride to give the intermediate II (240 mg) as a white solid. mp 262-267° C.; MS (ES) m/z 444.3.

Compound II (200 mg) in THF was treated with lithium aluminum hydride (LAH, 150 mg) and heated under reflux in a nitrogen atmosphere overnight. After cooling to room temperature, the reaction was quenched with aqueous Rochelle salt (sodium potassium tartrate) and the aqueous solution was extracted several times with ether. The ether layers were combined, dried ($MgSO_4$), and evaporated under reduced pressure to give a residue which was purified by flash chromatography on silica gel eluting with 1-3% methanol in methylene chloride. The title compound was isolated along with 100 mg of unreduced material. The unreduced material was dissolved in THF, treated with LAH (100 mg) and heated under reflux overnight. After workup as described above, the second batch of product was combined with the first batch to give the title compound (33 mg). mp 92-96° C.; MS (ES) m/z 432.2.

Example 2

N-[(6-fluoro-2,3,4,9-tetrahydro-1H-carbazol-3-yl) methyl]-N-{[(2S)-8-methyl-2,3-dihydro[1,4]dioxino [2,3-f]quinolin-2-yl]methyl}amine

6-Fluoro-2,3,4,9-tetrahydro-1H-carbazole-3-carboxylic acid ethyl ester (III)

4-Cyclohexanonecarboxylic acid ethyl ester (25 g, 0.14 m) and 4-fluorophenyhydrazine hydrochloride (22.5 g, 0.13 m) were dissolved in ethanol (450 mL) and heated under reflux for 16 hrs. After cooling, the white solid was filtered off and the solvent removed under reduced pressure. After partitioning the residue between water and ethyl acetate, the organic portion was separated, dried ($MgSO_4$), and evaporated under reduced pressure to give compound III (35.5 g, 0.13 m). The crude product was recrystallized from heptane. mp: 115-117° C. MS: [M+H]+ @m/e=262. [Lit. ref.: Block, M. H., et al. *J. Med. Chem.* 2002, 45, 3509].

(6-Fluoro-2,3,4,9-tetrahydro-1H-carbazol-3-yl)-methanol (IV)

Lithium aluminum hydride (800 mg) was added portion-wise to a solution of ester I (5.77 g, 22.1 mmol) in dry THF (100 mL). The mixture was stirred at ambient under nitrogen for 16 hrs, followed by quenching with the addition of an aqueous Rochelle salt solution (sodium potassium tartrate). The reaction mixture was diluted with ether and the phases were separated. The aqueous phase was extracted once with ether and the ether layers were combined, dried ($MgSO_4$), and evaporated to give a residue. The residue was purified by chromatography on silica gel eluting with hexane/ethyl acetate (2:1) to give compound IV (3.90 g, 17.8 mmole, 80%), mp: 107-109° C. MS: [M–H]– @m/z=218.1.

6-Fluoro-2,3,4,9-tetrahydro-1H-carbazole-3-carbaldehyde (V)

Dess-Martin periodinane (7.37 g, 17.4 mmol) was added portion-wise to a stirred solution/suspension of alcohol II (2.64 g, 11.8 mmole) in dichloromethane (120 mL). The alcohol completely dissolved after the Dess-Martin reagent was added. The reaction mixture was stirred at ambient temperature for 30 min, and then quenched with ethanol. The reaction mixture was diluted with ether (860 mL) and washed twice with saturated aqueous sodium bicarbonate (550 mL) followed by 5% sodium thiosulfate pentahydrate. After washing with brine and drying ($MgSO_4$), the solvent was evaporated to give a residue which was purified by chromatography on silica gel eluting with hexane/ethyl acetate (4:1). Compound V was obtained in 47% yield (1.2 g). mp: 96-98° C. MS: [M–H]– @m/z=216.1.

Glacial acetic acid (0.58 mL) and sodium cyanoborohydride (580 mg) were added to a solution of [(2S)-8-methyl-2,3-dihydro-[1,4]dioxino[2,3-f]quinolin-2-yl]methylamine (1.10 g, 4.8 mmol) and aldehyde V (1.04 g, 4.8 mmol) in methanol (80 mL). The reaction mixture was stirred at ambient temperature under nitrogen for 4 hrs. The solvent was removed under reduced pressure and the residue was partitioned between water and ethyl acetate. The organic portion was evaporated and the residue was chromatographed on silica gel eluting with 3% methanol in dichloromethane to give 1.8 g (89%) of the title compound. mp: 89-97° C. MS: [M–H]– @m/z 430.1.

Example 3

S,S-(6-Fluoro-2,3,4,9-tetrahydro-1H-carbazol-3-ylmethyl)-(8-methyl-2,3-dihydro-[1,4]dioxino[2,3-f] quinolin-2-ylmethyl)-amine The mixture of diastereomers in Example 2 was separated by chromatography using a Varian Prep with Chiralpak AD (0.2×15 cm); mobile phase: methanol with diethylamine. The title product [mp 80-84° C.; MS (ES) m/z 430.2] was dissolved in ethanol and treated with two equivalents of ethereal HCl. Yellow dihydrochloride precipitated out immediately. The compound was isolated by filtration and was washed with ethanol. After drying in vacuo, the title compound was obtained as the dihydrochloride sesquihydrate. mp 253-263° C., MS: [M+H]+ @m/z 432.2.

Example 4

S, —S-(6-Fluoro-2,3,4,9-tetrahydro-1H-carbazol-3-ylmethyl)-(8-methyl-2,3-dihydro-[1,4]dioxino[2,3-f] quinolin-2ylmethyl)-amine The title compound can be made by the following procedure.

Step 1: 6-Fluoro-2,3,4,9-tetrahydro-1H-carbazole-3-carboxylic acid ethyl ester 4-Cyclohexanonecarboxylic acid ethyl ester (77 g, 450 mmol) and 4-fluorophenylhydrazine hydrochloride (72 g, 443 mmol) were refluxed in 1.25 L of anhydrous ethanol overnight. The resulting yellow solution was cooled, crystals filtered, the filtrate evaporated, the residue partitioned between ethyl acetate and water, organic layer dried over sodium sulfate, evaporated, crystallized from ethyl acetate/heptane to give 113 g (98%) of the desired product.

Step 2: 6-Fluoro-2,3,4,9-tetrahydro-1H-carbazole-3-carboxylic acid

6-Fluoro-2,3,4,9-tetrahydro-1H-carbazole-3-carboxylic acid ethyl ester (80 g, 0.3 mol) was dissolved in 1 L of ethanol solution of KOH (28 g, 0.5 mol). The resulting mixture was stirred under nitrogen at 40-45° C. until completion of hydrolysis (TLC, HPLC) in 3 hrs. To the cooled solution were added 0.5 L of 1N aqueous HCl and 0.5 L of water; the resulting mixture was concentrated under reduced pressure. The target compound crystallized out of the aqueous solution when ethanol boiled out; 71.2 g (99%) of the title compound were obtained after drying.

Step 3: (3S)-6-Fluoro-2,3,4,9-tetrahydro-1H-carbazole-3-carboxylic acid

The racemic acid, (68 g, 292 mmol) was dissolved in 500 ml of acetonitrile, and the warm solution was mixed up with a warm solution of (−)-cinchonidine (43 g, 146 mmol) in 500 ml of methanol. The resulting mixture was left to cool down slowly in a dark glass. The formed salt was filtered, washed with acetonitrile; a second crop of crystals was also filtered, washed with acetonitrile, and combined with the first crop. The mother liquor was concentrated, partitioned between methyl tert-butyl ether (MTBA) and 1N HCl, the organic layer dried over MgSO$_4$, filtered through magnesol, and evaporated; the free acid was crystallized from cyclohexane to give 42 g of 80% pure S-enantiomer.

The S-enriched acid (12 g, 51 mmol) was dissolved in 200 ml of acetonitrile, and the warm solution was mixed with a warm solution of 1S,2S-(+)-pseudoephedrine (8.5 g, 51 mmol) in 150 ml of acetonitrile. The resulting mixture was left to crystallize while cooling down slowly. The salt was filtered, washed with cold acetonitrile; the free acid isolated as before. The title compound was obtained as white crystals; yield 8 g (83% from 12 g of the enriched mixture), m. p. 200-203° C.; $[\alpha]_D$ −0.164 (1% solution in methanol, 25° C.).

Step 4: (3S)-6-Fluoro-2,3,4,9-tetrahydro-1H-carbazole-3-carboxamide (3S)-6-Fluoro-2,3,4,9-tetrahydro-1H-carbazole-3-carboxylic acid (18 g, 77 mmol), was suspended in 200 ml of methylene chloride together with 50 ml of 2N oxalyl chloride; several drops of DMF were added, and the resulting mixture was stirred at room temperature until it became a clear solution (about 2 hrs). The solvent was evaporated at reduced pressure at room temperature, the residue dissolved in 500 ml of dry acetone, the solution cooled to −5° C., and to the cold solution were added fast 300 ml of 7N aqueous ammonia, with vigorous stirring and cooling. The temperature went up to 5° C., but no higher. An additional 200 ml of aq. ammonia were added, the resulting mixture stirred for another 30 min, acetone evaporated under reduced pressure, the amide, crystallized out of aqueous solution, was filtered, washed with water, and dried to give 13.7 g, (76%) of white crystals, mp: 170-172° C.

Step 5: {[(3S)-6-Fluoro-2,3,4,9-tetrahydro-1H-carbazol-3-yl]methyl}amine (3S)-6-Fluoro-2,3,4,9-tetrahydro-1H-carbazole-3-carboxamide (34.7 g, 150 mmol), was dissolved in 1 L of dry THF, and to the solution were added 300 ml of 1N lithium aluminum hydride in THF. The resulting solution, turning into suspension, was refluxed at vigorous stirring for 1 hr, completion checked by HPLC. The resulting suspension was cooled to 0-5° C., and quenched very slowly with the saturated solution of sodium potassium tartrate (Rochelle salt). The temperature was initially kept below 15° C., then let up to the ambient; 125 ml of the salt solution were added, while the solids in the suspension became crystalline and easily filterable. The reaction mixture was filtered through paper, the filtrate dried over sodium sulfate, evaporated, crystallized from MTBE, dried in the oven to give 26.9 g (82%) of the title compound as white crystals, mp: 121-123° C.

Step 6: S,S-(6-Fluoro-2,3,4,9-tetrahydro-1H-carbazol-3-ylmethyl)-(8-methyl-2,3-dihydro-[1,4]dioxino[2,3-f]quinolin-2-ylmethyl)-amine A mixture of {[(3S)-6-Fluoro-2,3,4,9-tetrahydro-1H-carbazol-3-yl]methyl}-amine (34.2 g, 156 mmol), [(2R)-8-methyl-2,3-dihydro[1,4]dioxino[2,3-f]quinolin-2-yl]methyl 4-bromobenzenesulfonate (45.1 g, 100 mmol), and dimethylaminopyridine (12.2 g, 100 mmol) in 300 ml of dry DMSO was stirred under nitrogen at 90° C. for 3 hr, control by HPLC. The resulting mixture was cooled, poured into aqueous sodium bicarbonate (1.5 L), the gum that precipitated on the bottom of the flask was dissolved in ethyl acetate, washed with brine and water, dried over sodium sulfate, and concentrated. The resulting gum was dissolved in ethanol, and upon stirring, crystallized out to give 30 g (69.6%) of the title compound as off-white crystals.

Example 5

N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine The other diastereoisomer isolated using the method of Example 3 is the title compound. mp 89-93° C.; MS (ES) @m/z 432.2. The title compound was converted to the dihydrochloride salt as described in Example 3 to give the compound of Example 5. mp 229-236° C.; MS (ES) @m/z 430.1.

Example 6

N-[(6-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine The title compound was prepared according to the method of Example 2 using the N-methyl analog (1.0 g) of the aldehyde V and [(2S)-8-methyl-2,3-dihydro[1,4]dioxino[2,3-f]quinolin-2-yl]methylamine (800 mg, 3.5 mmol) to give the title compound (920 mg). mp 57-62° C.; MS (ES) @m/z 446.2.

The N-methyl analog of V was prepared by treating the alcohol IV with iodomethane in DMF containing sodium hydride for 1 hr at room temperature. The resulting N-methyl analog of IV was converted to the corresponding aldehyde as described in Example 2.

Example 7

N-{([(3S)-6-fluoro-9-methyl-2,3,4,9-tetrahydro-1H-carbazol-3-yl]methyl}-N-{[(2S)-8-methyl-2,3-dihydro[1,4]dioxino[2,3-f]quinolin-2-yl]methyl}amine The mixture of diastereomers in Example 6 was separated by chiral chromatography according to Example 3 to give the title product. mp 127-129° C.; MS (ES) @m/z 446.2. The title compound was dissolved in ethanol and treated with two equivalents of ethereal HCl as described in Example 3, to give the dihydrochloride salt. mp 220-226° C., MS (ES) @m/z 446.2.

Example 8

N-{[(3R)-6-fluoro-9-methyl-2,3,4,9-tetrahydro-1H-carbazol-3-yl]methyl}-N-{[(2S)-8-methyl-2,3-dihydro[1,4]dioxino[2,3-f]quinolin-2-yl]methyl}amine The other diastereoisomer isolated using the method of Example 3 is the title compound. mp 88-94° C. MS (ES) m/z 446.2. The title compound was converted to the dihydrochloride salt as described in Example 3, mp 242-260° C.; MS (ES) @m/z 446.2.

Example 9

N-{[(3R)-6,8-difluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine dihydrochloride The title compound was prepared according to Example 2 using the 6,8-difluoro analog (235 mg, 1.0 mmol) of aldehyde V and [(2S)-8-methyl-2,3-dihydro[1,4]dioxino[2,3-f]quinolin-2-yl]methylamine (133 mg, 0.5 mmol) to give a mixture of diastereomeric products which was separated according to the method of Example 3 to give the freebase of the title compound. The free base was converted to the dihydrochloride salt as described in Example 3. mp 260-272° C.; MS (ES) @m/z 450.2.

Example 10

N-{[(3S)-6,8-difluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine dihydrochloride The title compound was obtained as described in Example 5. mp 267-275° C.; MS (ES) @m/z 450.20.

Example 11

[(5-fluoro-2,3,4,9-tetrahydro-1H-carbazol-3-yl)methyl]{[(2S)-8-methyl-2,3-dihydro[1,4]dioxino[2,3-f]quinolin-2-yl]methyl}amine dihydrochloride The title compound was prepared according to the method of Example 2 using the 5-fluoro analog (100 mg, 0.46 mmol) of aldehyde V and [(2S)-8-methyl-2,3-dihydro[1,4]dioxino[2,3-f]quinolin-2-yl]methylamine (105 mg) to give the free base of the title compound which was converted to the dihydrochloride salt (79 mg). mp 220-230° C.; MS (ES) @m/z 432.2.

Example 12

N-[(5-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine The title compound was prepared according to the method of Example 6 using the N-methyl analog (145 mg, 0.63 mmol) of aldehyde V described in Example 1 and [(2S)-8-methyl-2,3-dihydro[1,4]dioxino[2,3-f]quinolin-2-yl]methylamine (144 mg, 0.63 mmol) to give the title compound. mp 84-90° C.; MS (ES) @m/z 446.2.

Example 13

N-[(7-fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}amine The title compound of Example 13 was prepared according to the method of Example 2 using the 7-fluoro analog (390 mg, 1.8 mmol) of aldehyde V described in Example 1 and [(2S)-8-methyl-2,3-dihydro[1,4]dioxino[2,3-f]quinolin-2-yl]methylamine (420 mg, 1.8 mmol) to give the title compound. mp 89-97° C.; MS (ES) @m/z 432.2.

Example 14

(3S)-3-[({[(2S)-8-methyl-2,3-dihydro[1,4]dioxino[2,3-f]quinolin-2-yl]methyl}amino)methyl]-2,3,4,9-tetrahydro-1H-carbazole-6-carbonitrile dihydrochloride The title compound was prepared according to Example 2 using the 6-cyano analog (121 mg, 0.54 mmol) of aldehyde V and [(2S)-8-methyl-2,3-dihydro[1,4]dioxino[2,3-f]quinolin-2-yl]methylamine (120 mg, 0.52 mmol) to give a mixture of diastereomeric products which was separated according to the method of Example 3 to give the freebase of the title compound. The free base was converted to the dihydrochloride salt as described in Example 3. mp 236-241° C.; MS (ES) @m/z 439.2.

Example 15

(3R)-3-[({[(2S)-8-methyl-2,3-dihydro[1,4]dioxino[2,3-f]quinolin-2-yl]methyl}amino)methyl]-2,3,4,9-tetrahydro-1H-carbazole-6-carbonitrile dihydrochloride The other diastereoisomer isolated using the method of Example 3 is the free base of the title compound. The title compound was converted to the dihydrochloride salt as described in Example 3. mp 254-258° C. MS (ES) @m/z 439.2.

Example 16

C-(6-Fluoro-2,3,4,9-tetrahydro-1H-carbazol-3-yl)-methylamine

The title compound was prepared by generally following the procedure of E. W. Taylor, *Synthetic Communications* 1989 vol. 19 (3&4) 369-372.

Preparation of the Amide (VI)

6-Fluorotetrahydrocarbazole-3-carboxylic acid (232 mg, 1 mmol) was dissolved in anhydrous tetrahydrofuran (THF, 40 mL) under a nitrogen atmosphere. Carbonyldiimidazole (CDI, 162 mg, 1 mmol) was added followed by additional THF (20 mL). The reaction mixture was heated under reflux for 3.5 hr, cooled to room temperature and allowed to stir overnight. Gaseous ammonia was passed over a cold finger and the liquid ammonia was added to the reaction mixture over 45 min. The cloudy reaction mixture was allowed to stir for 1 hr. The volatiles were evaporated under reduced pressure to give a peach-colored oil. The oil was dissolved in ethyl acetate, washed with water, followed by 0.5N HCl, saturated $NaHCO_3$, and brine. The ethyl acetate layer was dried ($MgSO_4$), filtered, and evaporated under reduced pressure to give 160 mg (69%) of the amide VI as a rose-colored oil.

The amide VI (100 mg, 0.43 mmol) was dissolved in anhydrous THF (30 mL) with stirring under nitrogen. To this was added 1M $BH_3$ in THF (4.0 mL, 4 mmol). The reaction mixture was heated under reflux for 3 hr. The reaction was quenched with 0.5N HCl (10 mL) added dropwise under nitrogen. The volatiles were evaporated under reduced pressure. The phases were separated. The aqueous phase was chilled in an ice bath and made basic with solid sodium hydroxide. The aqueous phase was extracted with ethyl acetate three times. The layers were combined and dried over $MgSO_4$. After filtration the ethyl acetate phase was evaporated under reduced pressure to give the free base of the title compound as a clear oil (62 mg, 66%). The oil was treated with ethereal HCl to give the title compound. mp 180° C. (DEC); MS (APCI) @m/z 219.

Example 17

{[(3S)-6-fluoro-2,3,4,9-tetrahydro-1H-carbazol-3-yl] methyl}amine

The amide enantiomers VI are separated by chiral HPLC using hexane/IPA (90:10) on a Whelk-O column to give the tide compound. mp 121-123° C.; MS (ESI) m/z 219.1.

Example 18

Ethyl 7-oxabicyclo[4.1.0]heptane-3-carboxylate (intermediate 1)

To a solution of ethyl cyclohex-3-ene-1-carboxylate (14.0 g, 90 mmol) in $CH_2Cl_2$ (350 mL) was added meta-chloroperbenzoic acid (18.9 g, 110 mmol) at 0° C. The reaction mixture was stirred at room temperature for 2.5 hours. After cooling to 0° C., the reaction was neutralized with aqueous $Na_2CO_3$ solution. The organic layer was collected and washed with water and brine, then was dried over $MgSO_4$ and concentrated in vacuo to a light oil (17.8 g), which was used in the next reaction with further purification.

Example 19

Ethyl 4-bromo-3-hydroxycyclohexanecarboxylate (intermediate 2)

To a solution of ethyl 7-oxabicyclo[4.1.0]heptane-3-carboxylate (17.8 g) in $CH_2Cl_2$ (350 mL) was added 40% HBr solution (120 mL). The biphasic mixture was stirred vigorously for 25 min, then was neutralized with aqueous $NaHCO_3$ solution. The organic layer was collected and dried over $MgSO_4$, then was concentrated in vacuo. The residue was diluted with toluene (120 mL), and para-toluene sulfonic acid (120 mg, 0.6 mmol) was added. The mixture was heated at 128° C. with azeotropic removal of water over 3.5 hours, then was concentrated in vacuo to afford 21 g of a brown residue, which was used in the next reaction without purification.

Example 20

Ethyl 4-bromo-3-oxocyclohexanecarboxylate (intermediate 3)

To a solution of ethyl 4-bromo-3-hydroxycyclohexanecarboxylate (15.06 g) in acetone (300 mL) at 0° C. was added $CrO_3$ (12.0 g, 120 mmol), and 2 N $H_2SO_4$ (60 mL). The mixture was stirred at room temperature for 30 min. Isopropanol (15 mL) was added and the reaction was stirred for 20 min. The volume was reduced under vacuum then diluted with water and extracted with ethyl acetate. The organic layer was washed with water, then brine, was dried over $MgSO_4$ and concentrated in vacuo. Purification by chromatography on silica gel (10% EtOAc in hexane) afforded 6.7 g of tide compound.

Example 21

Ethyl 4-[(4-fluorophenyl)thio]-3-oxocyclohexanecarboxylate (intermediate 4)

To a solution of ethyl 4-bromo-3-oxocyclohexanecarboxylate (5.2 g, 20.9 mmol) in EtOH (120 mL) at 80° C. was added a solution of 4-fluorobenzenethiol (2.22 mL, 20.9 mmol) and KOH (1.29 g, 22.9 mmol) in EtOH (50 mL). The suspension was stirred for 30 min then filtered. The filtrate was concentrated in vacuo then diluted with water and extracted with diethyl ether. The organic layer was washed with water then brine, then was dried over $MgSO_4$ and concentrated in vacuo. Purification by chromatography on silica gel (15% EtOAc in hexane) afforded the title compound (3.08 g, 51%) as a white solid: mp 96-97° C.; MS (+) 297 $(M+H)^+$.

Example 22

Ethyl 3-oxo-4-(phenylthio)cyclohexanecarboxylate (intermediate 5)

To a solution of ethyl 4-bromo-3-oxocyclohexanecarboxylate (3.73 g, 15 mmol) in EtOH (30 mL) at 80° C. was added a solution of benzenethiol (1.65 mL, 15 mmol) and NaOH (0.6 g, 15 mmol) in EtOH (100 mL). The suspension was stirred for 1 hour, then was concentrated in vacuo. The residue was diluted with water and extracted with EtOAc. The organic layer was washed with water then brine, then was dried over $MgSO_4$ and concentrated in vacuo. Purification by chromatography on silica gel afforded 2.56 g (61%) of the title compound as a yellow oil: MS (−) 277 $(M-H)^-$.

Example 23

Ethyl 8-fluoro-1,2,3,4-tetrahydrodibenzo[b,d]
thiophene-2-carboxylate (intermediate 6)

To a room temperature solution of ethyl 4-[(4-fluorophenyl)thio]-3-oxocyclohexanecarboxylate (3.4 g, 11.5 mmol) in dichloroethane (100 mL) was added $AlCl_3$ (3.7 g, 27.6 mmol). The mixture was heated to 80° C. for 1 hour. After cooling to room temperature, the reaction was diluted with water and acidified with 1 N HCl. The aqueous mixture was extracted with EtOAc. The organic layer was washed with water then brine, then was dried over $MgSO_4$ and concentrated to an oil. Purification by chromatography on silica gel afforded 2.5 g (77%) of the title compound as semi-solid: MS (+) 278 (M)$^+$.

Example 24

Ethyl 1,2,3,4-tetrahydrodibenzo[b,d]thiophene-2-
carboxylate (intermediate 7)

The title compound (1.43 g, 61% yield) was prepared by the generally following the same procedure described above for intermediate 6. MS (+) 260 (M)$^+$.

Example 25

8-Fluoro-1,2,3,4-tetrahydrodibenzo[b,d]thiophene-2-
carboxylic acid (intermediate 8)

To a solution of ethyl 8-fluoro-1,2,3,4-tetrahydrodibenzo[b,d]thiophene-2-carboxylate (2.5 g, 9 mmol) in EtOH (60 mL) was added KOH (0.81 g, 15 mmol). The reaction was stirred at 40° C. overnight. After cooling in an ice-water bath, the mixture was acidified to pH 2-3 with 1 N HCl. Water was added and the resulting white solid precipitate was collected and dried to afford 2.15 g (96%) of the title compound: mp 245° C. (dec.), MS (−) 249 (M−H)$^-$.

Example 26

1,2,3,4-Tetrahydrodibenzo[b,d]thiophene-2-carboxy-
lic acid (intermediate 9)

To a solution of ethyl 1,2,3,4-tetrahydrodibenzo[b,d]thiophene-2-carboxylate (1.15 g, 4.42 mmol) in EtOH (50 mL) was added KOH (0.4 g, 7.07 mmol). The reaction was stirred at 40° C. for 3 hours. After cooling to room temperature, the mixture was extracted with ether. The ether layer was washed with aqueous $Na_2CO_3$. The combined aqueous layers were acidified to pH 2 with conc. HCl and extracted with EtOAc. The EtOAc layer was washed with brine, then was dried over $MgSO_4$ and concentrated to dryness to afford the 0.77 g (75%) of the title compound as a white solid: mp 202-203° C., MS (−) 231 (M−H)$^-$.

Example 27

8-Fluoro-1,2,3,4-tetrahydrodibenzo[b,d]thiophene-2-
carboxamide (intermediate 10)

To a suspension of 8-fluoro-1,2,3,4-tetrahydrodibenzo[b,d]thiophene-2-carboxylic acid (1.2 g, 4.8 mmol) in $CH_2Cl_2$ (20 mL) was added oxalyl chloride (0.55 mL, 6.24 mmol) and a drop of DMF. The reaction was stirred at room temperature for 30 min, then was concentrated in vacuo. The resulting residue was dissolved in acetone (30 mL) and cooled to −5° C. Conc. $NH_4OH$ (10 mL) was added quickly, resulting in a white precipitate. The suspension was stirred for 30 min, then diluted with water and filtered to afford 1.14 g (95%) of the title compound as a white solid: mp 201-202° C.; MS (−) 248 (M−H)$^-$.

Example 28

1,2,3,4-Tetrahydrodibenzo[b,d]thiophene-2-carboxa-
mide (intermediate 11)

Using generally the same procedure described for intermediate 10, the title compound (1.14 g, 97% yield) was isolated as a white solid: mp 153-155° C.; MS (+) 232 (M+H)$^+$.

Example 29

1-(8-Fluoro-1,2,3,4-tetrahydrodibenzo[b,d]thien-2-
ylmethyl)amine (intermediate 12)

To a room temperature solution of 8-fluoro-1,2,3,4-tetrahydrodibenzo[b,d]thiophene-2-carboxamide (1.1 g, 4.42 mmol) in anhydrous THF (30 mL) was added 1 N LAH in THF (8.84 mL). The reaction was heated to 70° C. for 1 hour, then was cooled to 0° C. and quenched by the slow addition of saturated aqueous $Na^+/K^+$ tartrate solution. The rate of addition was such as to maintain the reaction temperature below 15° C. The resultant suspension was filtered, and the filtrate was dried over $MgSO_4$, then concentrated in vacuo to afford the title compound (1.01 g, 96%) as a white solid. The hydrochloride acid salt was prepared by treating the amine in MeOH with 1 N HCl in $Et_2O$ to afford a yellow solid: mp 163-165° C.; MS (+) 236 (M+H)$^+$.

Example 30

(1,2,3,4-tetrahydrodibenzo[b,d]thien-2-ylmethyl)
amine (intermediate 13)

Using generally the same procedure as described above for intermediate 12, the title compound (0.65 g, 93% yield) was isolated as its hydrochloride salt, an off-white solid: mp 216-218° C. (dec); MS (+) 218 (M+H)$^+$.

Example 31

[(8-Fluoro-1,2,3,4-tetrahydrodibenzo[b,d]thien-2-yl)
methyl]{[(2S)-8-methyl-2,3-dihydro[1,4]dioxino[2,
3-f]quinolin-2-yl]methyl}amine To a solution of 1-(8-fluoro-1,2,3,4-tetrahydrodibenzo[b,d]thien-2-ylmethyl)amine (0.75 g, 3.19 mmol) in DMSO (8 mL) was added [(2R)-8-methyl-2,3-dihydro[1,4]dioxino[2,3-f]quinolin-2-yl]methyl 4-bromobenzenesulfonate (0.97 g, 2.12 mmol) and dimethylaminopyridine (0.25 g, 2.12 mmol). The reaction was heated at 90° C. for 2 hours. After cooling to room temperature, the mixture was diluted with aqueous $NaHCO_3$ solution and extracted with ethyl acetate. The organic layer was washed with water and brine, then was dried over $MgSO_4$ and concentrated to a yellow oil. Purification by chromatography on silica gel afforded a mixture of diastereomers of the title compound as a white foam (460 mg, 48%). The diastereomers were separated by chiral HPLC and converted to their corresponding dihydrochloride salts by treating a methanolic solution of the amine with 1 N HCl in diethyl ether: Diastereomer 1: 67 mg of yellow solid: mp 115-118° C., MS (+) 449 (M+H)+. Diastereomer 2: 72 mg of yellow solid: mp 198-201° C., MS (+) 229 (M+H)+.

Example 32

{[(2S)-8-methyl-2,3-dihydro[1,4]dioxino[2,3-f]quinolin-2-yl]methyl}(1,2,3,4-tetrahydrodibenzo[b,d]thien-2-ylmethyl)amine Using generally the same procedure described above for Example 31, the two diastereomers of the title compound were isolated as their dihydrochloride salts: Diastereomer 1: 130 mg of a yellow solid: mp 212° C. (dec.); MS (+) 431 (M+H)+. Diastereomer 2: 135 mg of a yellow solid: mp 220° C. (dec.); MS (+) 431 (M+H)+.

Example 33

Ethyl 3-bromo-4-oxocyclohexanecarboxylate (intermediate 14)

To a 0° C. solution of ethyl 4-oxocyclohexanecarboxylate (6.0 g, 35.3 mmol) in diethyl ether (200 mL) was added dropwise a solution of bromine (5.3 g, 33.3 mmol) in diethyl ether (20 mL). The resulting mixture was stirred at room temperature for 40 min, then was cooled in an ice/water bath, diluted with water, and neutralized with aqueous NaHCO$_3$ solution. The organic layer was separated and washed with water then brine, then was dried over MgSO$_4$ and concentrated to an oil, which was used in next reaction without purification.

Example 34

Ethyl 3-[(3-fluorophenyl)thio]-4-oxocyclohexanecarboxylate (intermediate 15)

Using generally the same procedure described above for intermediate 5, the title compound (4.86 g, 93% yield) was isolated as an oil: MS (−) 296(M−H)−.

Example 35

Ethyl 7-fluoro-1,2,3,4-tetrahydrodibenzo[b,d]thiophene-3-carboxylate (intermediate 16)

Using generally the same procedure described above for intermediate 6, the title compound (0.62 g, 87% yield) was isolated as an oil: MS (+) 278 (M)+.

Example 36

7-Fluoro-1,2,3,4-tetrahydrodibenzo[b,d]thiophene-3-carboxylic acid (intermediate 17)

Using generally the same procedure described above for intermediate 8, the title compound (1.74 g, 78% yield) was isolated as a white solid: mp 195-198° C.; MS (−) 249 (M−H)−.

Example 37

7-Fluoro-1,2,3,4-tetrahydrodibenzo[b,d]thiophene-3-carboxamide (intermediate 18)

Using generally the same procedure described above for intermediate 10, the title compound (1.0 g, 94% yield) was isolated as a white solid: mp 184-185° C.; MS (+) 250 (M+H)+.

Example 38

1-(7-Fluoro-1,2,3,4-tetrahydrodibenzo[b,d]thien-3-ylmethyl)amine (intermediate 19)

Using generally the same procedure described above for intermediate 12, the title compound (0.45 g, 50% yield) was prepared and isolated as its hydrochloric acid salt as a white solid: mp 230-235° C.; MS (+) 236 (M+H)+.

Example 39

[(7-fluoro-1,2,3,4-tetrahydrodibenzo[b,d]thien-3-yl)methyl]{[(2S)-8-methyl-2,3-dihydro[1,4]dioxino[2,3-f]quinolin-2-yl]methyl}amine Using essentially the same procedure described above for Example 31, the two diastereomers of the title compound were prepared and isolated as their di-hydrochloride salts: Diastereomer 1: 140 mg of a light yellow solid: mp 188-191° C.; MS (+) 449 (M+H)+. Diastereomer 2: 144 mg of a light yellow solid: mp 215° C. (dec.); MS (+) 449 (M+H)+.

Example 40

[2-(6-Fluoro-2,3,4,9-tetrahydro-1H-carbazol-3-yl)ethyl]{[(2S)-8-methyl-2,3-dihydro[1,4]dioxino[2,3-f]quinolin-2-yl]methyl}amine dihydrochloride Toluene-4-sulfonic acid 6-fluoro-2,3,4,9-tetrahydro-1H-carbazol-3-yl-methyl ester A solution of (6-fluoro-2,3,4,9-tetrahydro-1H-carbazol-3-yl)methanol (compound IV of Example 2) (5.975 g, 0.0272 mol) in anhydrous pyridine (15 mL) was cooled in ice bath and treated dropwise under vigorous stirring with an ice cold solution of para-toluenesulfonyl chloride (6.17 g) in anhydrous pyridine (10 mL). After stirring for one hour in the cold, the mixture was placed overnight in the refrigerator. It was then quenched with water (100 mL) under stirring and cooling. After 30 minutes the mixture was extracted with ethyl acetate (3×100 mL). The extracts were washed with cold 3N sulfuric acid (100 mL), water (100 mL) and brine (100 mL), dried over anhydrous magnesium sulfate and evaporated to dryness. The crude material (light brown foam, 9.827 g) was used as such in the next step. MS (ES): [M−H]− @m/z 372.1.

(6-Fluoro-2,3,4,9-tetrahydro-1H-carbazol-3-yl)acetonitrile

To a suspension of the crude toluene-4-sulfonic acid 6-fluoro-2,3,4,9-tetrahydro-1H-carbazol-3-yl-methyl ester (9.827 g, 0.0263 mol) in ethanol (70 mL) was added solid sodium cyanide (49.01 g, 0.0447 mol). The mixture was stirred at gentle reflux for 16 hours. Following TLC, a small amount of additional sodium cyanide was added and heating resumed for 2 hours. Most of the solvent was removed under reduced pressure (ca 55 mL). The residue was slurried in water (70 mL) and extracted with diethyl ether (3×). The extracts were washed with water and brine, and dried over anhydrous magnesium sulfate. Removal of the solvent provided a mustard colored solid which was purified by flash chromatography on silica gel Merck-60 using a gradient from 8:2 to 1:1 of ethyl acetate in hexane. The desired title compound was obtained as a yellow oil that solidifies in vacuo to yield light yellow crystals (5.2 g), m.p. 136-138° C. MS (ES): [M–H]⁻ @m/z 227.1.

2-(6-Fluoro-2,3,4,9-tetrahydro-1H-carbazol-3-yl)-ethylamine

To a solution of (6-fluoro-2,3,4,9-tetrahydro-1H-carbazol-3-yl)acetonitrile (0.423 g, 1.857 mmol) in ethanol (55 mL) kept under nitrogen was added concentrated aqueous ammonia (38 mL) followed by 5% rhodium on alumina catalyst (40% by weight). The mixture was hydrogenated at room temperature and 50 psi for 24 hours. Following TLC, additional catalyst (1.130 g) was added and the hydrogenation was resumed. After 6 hours the catalyst was filtered off over Celite, the cake washed with ethanol and the filtrate evaporated to dryness at reduced pressure. The residue was treated with a small amount of ethanol and evaporated. The procedure was performed three times. The residual oil was purified by flash chromatography on silica gel Merck-60 using a gradient from 2:248 to 10:90 of ammonia saturated methanol in dichloromethane. The desired title compound was obtained as a pale yellow foam (0.405 g). MS (ES): [M–H]⁻ @231.1.

[2-(6-Fluoro-2,3,4,9-tetrahydro-1H-carbazol-3-yl) ethyl]{[(2S)-8-methyl-2,3-dihydro[1,4]dioxino[2,3-f]quinolin-2-yl]methyl}amine dihydrochloride salt To a solution of 2-(6-fluoro-2,3,4,9-tetrahydro-1H-carbazol-3-yl)-ethylamine (0.578 g, 1.28 mmol) in anhydrous acetonitrile (15 mL) was added [{2R}-8-methyl-2,3-dihydro[1,4-dioxino[2,3-f]quinolin-2-yl]methyl 4-bromobenzenesulfonate and solid potassium carbonate (0.195 g). The mixture was stirred and heated at 80° C. under nitrogen for 24 hours. The mixture was cooled, diluted with 10% aqueous sodium bicarbonate, the acetonitrile removed at reduced pressure and the residue extracted with ethyl acetate (3×). The extracts were washed with brine, dried over anhydrous magnesium sulfate and evaporated to dryness. The residue was purified by flash chromatography over silica gel Merck 60 using a gradient from 1:1:0.1 to 6:4:0.4 hexane-ethyl acetate-ammonia saturated methanol to provide the title compound as a white foam (0.431 g, mixture of diastereomers). MS (ES): [M+H]⁺ @m/z 446.2.

The foam was dissolved in 0.5 mL of ethyl acetate and treated with 2 equivalents of 1N hydrochloride acid in diethyl ether. The yellow solid obtained upon addition of excess diethyl ether was collected, washed with diethyl ether and dried in vacuo to provide the title compound (mixture of diastereomers), as the dihydrochloride salt. MS (ES): [M+H]⁺ @m/z 446.2.

Example 41

{2-[(3R)-6-Fluoro-2,3,4,9-tetrahydro-1H-carbazol-3-yl]ethyl}{[(2S)-8-methyl-2,3-dihydro[1,4]dioxino[2,3-f]quinolin-2-yl]methyl}amine dihydrochloride The mixture of diastereomers (free bases) in Example 40, was separated by chromatography using a Varian Prep with Chiralcel AD (2×25 cm); mobile phase: methanol with 0.1% diethylamine. The fractions corresponding to peak 1 were evaporated to dryness to provide the title compound as free base (off white foam). The free base was converted to the dihydrochloride salt as described in Example 40. MS (ES): [M+H]+ @m/z 446.3.

Example 42

{2-[(3S)-6-Fluoro-2,3,4,9-tetrahydro-1H-carbazol-3-yl]ethyl}{[(2S)-8-methyl-2,3-dihydro[1,4]dioxino[2,3-f]quinolin-2-yl]methyl}amine dihydrochloride The other diastereoisomer isolated using the method of Example 41 (corresponding to peak 2) is the title compound (free base). The free base was converted to the dihydrochloride salt as described in Example 40. MS (ES): [M+H]⁺ @m/z 446.3.

Example 43

N-{[(2S)-8-methyl-2,3-dihydro[1,4]dioxino[2,3-f]quinolin-2-yl]methyl}-2,3,4,9-tetrahydro-1H-carbazol-2-amine dihydrochloride Cyclohexane-2,3-dione monophenylhydrazone The title compound was prepared by a modification of published procedures (M. S. Berridge et al., Nucl. Med. Biol. 19 (5) 563-569 (1992); Brueckner R. et al., EP 1 424 337 A1 (2004)). To a stirred suspension of cyclohexane-1,3-dione (10 g, 0.089 mol) in water (64 mL) under nitrogen was added via dropping funnel 10-15 drops of a solution of phenylhydrazine (8.8 mL, 0.089 mmol) in water (124 mL). The mixture was stirred for 15 minutes at room temperature and then the remainder of the phenylhydrazine solution was added dropwise over a 4 hour period. Ethanol (21 mL) was added to facilitate stirring after about 30 mL of the hydrazine solution had been added. Stirring was continued for an additional 30 minutes. The orange solid was collected by filtration, washed with water and a small amount of 3:1 (v/v) water-ethanol, and dried in vacuo overnight to provide the title compound (15.01 g, 83.3%). MS (ES): [M+H]⁺ @m/z 203.1

1,3,4,9-Tetrahydrospiro[carbazole-2,2'-[1,3]dioxolane]

The title compound was prepared essentially according to published procedures (R. F. Borch et al., J. Org. Chem. 38 (15), 2729 (1973); Nader G. et al., French Patent 2729141 (1996)). A mixture of cyclohexane-2,3-dione monophenylhydrazone (10.1 g, 0.05 mol), diethylene glycol (25 mL) and para-toluene sulfonic acid monohydrate (11.4 g, 0.06 mol) in toluene (500 mL) was heated under nitrogen in an oil bath kept at 135° C. with water removal (Dean-Stark). After heating for 15 hours the mixture was cooled, the toluene was decanted and the tarry residue extracted three times with small portions of toluene. The combined organic phase was washed three times with saturated aqueous sodium bicarbonate, and dried over anhydrous magnesium sulfate. Removal of the solvent provided the crude title compound as a brown oil that partially solidified in vacuo (9.2 g). It was used as such in the next step. MS (ES): [M+H]⁺ @m/z 230.1

2,3,4,9-Tetrahydro-2H-carbazol-2-one

A solution of the crude 1,3,4,9-tetrahydrospiro[carbazole-2,2'-[1,3]dioxolane] (9.2 g, 0.040 mol) in methanol (153) was treated dropwise under stirring with a 10% aqueous sulfuric acid solution and the resulting orange brown mixture was stirred overnight at room temperature. The cherry red solution was diluted with water (230 mL) and extracted three times with dichloromethane. The combined extracts were washed with 1:1 (v/v) brine/water, dried over anhydrous magnesium sulfate and evaporated to dryness to provide a red brown solid. The latter was purified by flash chromatography over silica gel Merck 60, using a gradient from 5% to 20% of ethyl acetate in hexane to provide the desired title compound as a white solid (4.18 g), m.p. 131-133° C. MS (ES): [M–H]⁻ @m/z 184.1.

1,3,4,9-Tetrahydrocarbazole-2-one oxime

A solution of 2,3,4,9-tetrahydro-2H-carbazol-2-one (1 g, 5.93 mmol) in methanol (10 mL) and pyridine (10 mL) was treated with hydroxylamine hydrochloride (0.825 g, 11.87 mmol). The solution was stirred at room temperature under nitrogen overnight. Removal of the solvents in vacuo provided a residue that was dissolved in water (20 mL) and extracted three times with ethyl acetate. The combined extracts were washed with 0.1 N aqueous hydrochloric acid and water and dried over anhydrous magnesium sulfate. Removal of the solvent provided the title compound (1.09 g). The sample was triturated with ethyl acetate to yield a white solid, m.p. 196° C. (foaming at 202° C.). MS (ES): [M–H]⁻ @m/z 199.1.

2,3,4,9-Tetrahydro-1H-carbazol-2-ylamine

A suspension of the crude 1,3,4,9-tetrahydrocarbazole-2-one oxime (1.093 g, 5.45 mmol) in ethanol (27.5 mL) was treated while cooling in ice bath with 2.5 N aqueous sodium hydroxide (22 mL). To the stirred dark solution kept under nitrogen was added portionwise over 15 minutes Al—Ni alloy (2.05 g). After 5 minutes the cooling bath was removed and the mixture stirred at room temperature for one hour. The catalysts was filtered off over Celite, the cake quickly washed under nitrogen with a small amount of 1:1 (v/v) ethanol-water and the filtrate was extracted three times with dichloromethane. The combined extracts were washed with water and brine and dried over anhydrous magnesium sulfate. Removal of the solvent provided a dark brown foam that crystallized upon standing. The residue was purified by flash chromatography over silica gel Merck 60 using a gradient from 3% to 10% of ammonia saturated methanol in dichloromethane to provide the title amine as a foam (0.791 g). MS (ES): [M+H]⁺ @m/z 187.1

N-{[(2S)-8-methyl-2,3-dihydro[1,4]dioxino[$_{2,3}$-f]quinolin-2-yl]methyl}-2,3,4,9-tetrahydro-1H-carbazol-2-amine dihydrochloride To a solution of 2,3,4,9-tetrahydro-1H-carbazol-2-ylamine (0.680 g, 3.65 mmol) in acetonitrile (15 mL) kept under nitrogen was added potassium carbonate (0.518 g) followed by the [{2R)-8-methyl-2,3-dihydro[1,4-dioxino[2,3-f]quinolin-2-yl]methyl 4-bromobenzenesulfonate (1.35 g, 3 mmol). The solution was stirred and heated in an oil bath at 80° C. for 18 hours, cooled, and diluted with saturated aqueous sodium bicarbonate (15 mL). The acetonitrile was removed at reduced pressure and the residue was extracted three times with ethyl acetate. The combined extracts were dried over anhydrous magnesium sulfate and evaporated to dryness to provide a light brown foam (1.96 g). The residue was purified by flash chromatography on silica gel Merck 60 using a gradient from 55:44:1 to 50:44:6 of hexane-ethyl acetate-ammonia saturated methanol to provide the title compound as a light brown foam (0.647 g, mixture of diastereomers).

The foam was dissolved in 0.5 mL of ethyl acetate and treated with 2 equivalents of 1N hydrochloride acid in diethyl ether. The yellow solid obtained upon addition of excess diethyl ether was collected, washed with diethyl ether and dried in vacuo to provide the title compound as the dihydrochloride salt (mixture of diastereomers), m.p. 117-118° C. (dec). MS (ES): [M+H]⁺ @m/z 400.2.

Example 44

(2R)-N-{[(2S)-8-methyl-2,3-dihydro[1,4]dioxino[2,3-f]quinolin-2-yl]methyl}-2,3,4,9-tetrahydro-1H-carbazol-2-amine dihydrochloride The mixture of diastereomers (free bases) in Example 43 was separated by chromatography using a Varian Prep with Chiralcel AD (2×25 cm); mobile phase: methanol with 0.1% diethylamine. The fractions corresponding to peak 1 were evaporated to dryness to provide the title compound as free base (off white foam).

The free base was converted to the dihydrochloride salt as described in Example 43. MS (ES): [M+H]⁺ @m/z 400.2. $[\alpha]_D 25=-4.90°$ (c=1% solution, MeOH).

Example 45

(2S)-N-{[(2S)-8-methyl-2,3-dihydro[1,4]dioxino[2,3-f]quinolin-2-yl]methyl}-2,3,4,9-tetrahydro-1H-carbazol-2-amine dihydrochloride The other diastereoisomer isolated using the method of Example 44 (corresponding to peak 2) is the title compound (free base). The free base was converted to the dihydrochloride salt as described in Example 43. MS (ES): [M+H]⁺ @m/z 400.2. $[\alpha]_D 25=-108.6°$ (c=1% solution, MeOH).

Example 46

6-Fluoro-N-{[(2S)-8-methyl-2,3-dihydro[1,4]dioxino[2,3-f]quinolin-2-yl]methyl}-2,3,4,9-tetrahydro-1H-carbazol-2-amine 3-[N'-(4-Fluoro-phenyl)-hydrazino]-cyclohex-2-enone The title compound was prepared by a modification of a published procedure (Brueckner R. et al., European Patent EP 1 424 337 A1 (2004)). To a stirred solution of cyclohexane-1,3-dione (10 g, 0.089 mol) in ethanol (50 mL) and water (150 mL) was added portionwise under nitrogen over 15 minutes 4-fluorophenyl hydrazine hydrochloride (14.5 g, 0.089 mol). After 10 minutes 120 mL of 3:1 (v/v) water/ethanol was added in three portions. Solid sodium acetate (7.2 g) was then added portionwise over 45 minutes. The mixture was stirred for another 30 minutes at room temperature. The brown solid was collected, washed with 2×30 mL of 3:1 (v/v) water/ethanol and water, and dried in vacuo overnight to provide the title compound (16.48 g). MS (ES): [M+H]⁺ @m/z 221.1.

6-Fluoro-1,3,4,9-tetrahydrospirorcarbazole-2,2'-[1,3]dioxolane]

The title compound was prepared according to the procedure of Example 43 step B by replacing the cyclohexane-2,3-dione monophenylhydrazone with 3-[N'-(4-fluoro-phenyl)-hydrazino]-cyclohex-2-enone (11.01 g, 0.05 mol). The crude product was purified by flash chromatography on silica gel Merck 60 by using a gradient from 95:5:0.1 to 75:25:0.1 of hexane/ethyl acetate/ammonium hydroxide to provide the title compound as an off white solid (6.128 g), m.p. 159-161° C. (darkens at 130° C.). MS (ES): [M+H]+ @m/z 248.1.

6-Fluoro-1,3,4,9-tetrahydro-2H-carbazol-2-one

The title compound was prepared according to the procedure of Example 43 step C by replacing the 1,3,4,9-tetrahydrospiro[carbazole-2,2'-[1,3]dioxolane] with 6-fluoro-1,3,4,9-tetrahydrospiro[carbazole-2,2'-[1,3]dioxolane] (6.058 g, 0.0245 mol). The crude product was dissolved in warm methanol, treated with charcoal, filtered over Celite and the filtrate evaporated to dryness. The residue was slurried in a small amount of methanol, the off white solid collected and dried to provide the title compound (1.297 g), m.p. 165-167° C. MS (ES): [M−H]− @m/z 202.0.

6-Fluoro-1,3,4,9-tetrahydro-carbazol-2-one oxime

The title compound was prepared according to the procedure of Example 43 step D by replacing the 2,3,4,9-tetrahydro-2H-carbazol-2-one with 6-fluoro-1,3,4,9-tetrahydro-2H-carbazol-2-one (3.5 g, 17.22 mmol). The crude title compound was obtained as a pale brown solid (3.7 g) and used as such in the next step.

6-Fluoro-2,3,4,9-tetrahydro-1H-carbazol-2-ylamine

The title compound was prepared according to the procedure of Example 43 step E by replacing the 1,3,4,9-tetrahydrocarbazole-2-one oxime with 6-fluoro-1,3,4,9-tetrahydro-carbazol-2-one oxime (2 g, 8.6 mmol). The title compound was obtained as a light brown foam (1.44 g). MS (ES): [M+H]+ @m/z 205.1.

6-Fluoro-N-{[(2S)-8-methyl-2,3-dihydro[1,4]dioxino[2,3-f]quinolin-2-yl]methyl}-2,3,4,9-tetrahydro-1H-carbazol-2-amine dihydrochloride The title compound was prepared according to the procedure of Example 43 step F by replacing the 2,3,4,9-tetrahydro-1H-carbazol-2-ylamine with 6-fluoro-2,3,4,9-tetrahydro-1H-carbazol-2-ylamine (0.74 g, 3.62 mmol). The title compound was obtained as a light brown foam (free base, 0.558 g, mixture of diastereomers). The foam was dissolved in 0.5 mL of ethyl acetate and treated with 2 equivalents of 1N hydrochloride acid in diethyl ether. The yellow solid obtained upon addition of excess diethyl ether was collected, washed with diethyl ether and dried in vacuo to provide the title compound as the dihydrochloride salt (mixture of diastereomers), m.p. 226-228° C. (dec). MS (ES): [M+H]+ @m/z 418.2.

Example 47

(2R)-6-Fluoro-N-{[(2S)-8-methyl-2,3-dihydro[1,4]dioxino[2,3-f]quinolin-2-yl]methyl}-2,3,4,9-tetrahydro-1H-carbazol-2-amine dihydrochloride The mixture of diastereomers in Example 46 was separated by chromatography using a Varian Prep with Chiralcel AD (2×25 cm); mobile phase: methanol with 0.1% diethylamine. The fractions corresponding to peak 1 were evaporated to dryness to provide the title compound as free base (off white foam). The free base as converted to the dihydrochloride salt as described in Example 46. MS (ES): [M+H]+ @m/z 418.2. [α]$_D$25=−11.2° (c=1% solution, DMSO).

Example 48

(2S)-6-Fluoro-N-{[(2S)-8-methyl-2,3-dihydro[1,4]dioxino[2,3-f]quinolin-2-yl]methyl}-2,3,4,9-tetrahydro-1H-carbazol-2-amine dihydrochloride The other diastereoisomer isolated using the method of Example 47 (corresponding to peak 2) is the title compound (free base). The free base was converted to the dihydrochloride salt as described in Example 46. MS (ES): [M+H]+ @m/z 418.2. [α]$_D$25=−101.6° (c=1% solution, DMSO).

Example 49

N-{[(3S)-6-trifluoromethoxy-2,3,4,9-tetrahydro-1H-carbazol-3-yl]methyl}-N-{[(2S)-8-methyl-2,3-dihydro[1,4]dioxino[2,3-f]quinolin-2-yl]methyl}amine The title compound can be prepared by generally following the procedure described in Schemes 3, 7 and 8. The first step is to synthesize 6-(trifluoromethoxy)-2,3,4,9-tetrahydro-1H-carbazole-3-carboxylic acid ethyl ester as follows. A suspension of 4-cyclohexanonecarboxylic acid ethyl ester (2.25 g, 13.25 mmol) and 4-trifluoromethoxyphenyl hydrazine hydrochloride (3 g, 13.12 mmol) in ethanol (40 mL) can be refluxed overnight under nitrogen. The solvent can be removed at reduced pressure and the residue will be partitioned between aqueous saturated sodium bicarbonate and ethyl acetate. The organic phase can be washed with brine, dried over anhydrous magnesium sulfate and evaporated to dryness. The crude product can be purified by flash chromatography on silica gel Merck-60 using a gradient of ethyl acetate in hexane.

Following Scheme 6, (8-methyl-2,3-dihydro-[1,4]dioxino[2,3-f]quinolin-2-ylmethyl)-(6-trifluoromethoxy-2,3,4,9-tetrahydro-1H-carbazol-3-ylmethyl)-amine can be prepared. Then, generally following the reactions illustrated in Schemes 9 and 10 for the resolution of (8-methyl-2,3-dihydro-[1,4]dioxino[2,3-f]quinolin-2-ylmethyl)-(6-trifluoromethoxy-2,3,4,9-tetrahydro-1H-carbazol-3-ylmethyl)-amine, the desired diastereomers of N-{[(3S)-6-trifluoromethoxy-2,3,4,9-tetrahydro-1H-carbazol-3-yl]methyl}-N-{[(2S)-8-methyl-2,3-dihydro[1,4]dioxino[2,3-f]quinolin-2-yl]methyl}amine can be prepared. Alternatively, 6-(trifluoromethoxy)-2,3,4,9-tetrahydro-1H-carbazole-3-carboxylic acid ethyl ester can be converted to 6-trifluoromethoxy-2,3,4,9-tetrahydro-1H-carbazole-3-carboxylic acid amide by ammonolysis of the ester with for example, methanolic ammonia, without the need to go through 6-trifluoromethoxy-2,3,4,9-tetrahydro-1H-carbazole-3-carboxylic acid.

Example 50

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}ethanamine dihydrochloride dihydrate A solution of N-[(6-fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}amine (Example 2, 85 mg, 0.20 mmole) and acetaldehyde (31 mg, 0.7 mmole) in 1.0 mL methanol containing 0.033 mL glacial acetic acid was treated with 30 mg sodium cyanoborohydride and shaken at ambient temperature for 24 hours. The reaction was quenched by addition of 2 mL 1 N aqueous NaOH. Solvent was removed under reduced pressure and the residue was treated with 10 mL of ethyl acetate. The mixture was centrifuged, the supernatant was decanted, and solvent was removed under reduced pressure to give a residue which was purified by chromatography on silica gel eluting with 10% to 30% ethyl acetate in hexane. An ethanolic solution of the free base product was treated with ethereal HCl. The solvent was evaporated off leaving the title compound dihydrochloride dihydrate as a yellow solid (9 mg, 8% yield), m.p. 234-249° C.; MS (ES) m/z 460.2.

Example 51

N-[(6-Fluoro-2,3,4,9-tetrahydro-1H-carbazol-3-yl) methyl]-N-{[(2S)-8-methyl-2,3-dihydro[1,4]dioxino [2,3-f]quinolin-2-yl]methyl}propan-1-amine dihydrochloride dihydrate The title compound was prepared by generally following the procedure of Example 50, using 0.7 mmole propionaldehyde instead of acetaldehyde. Yield=8 mg (7%), m.p. 187-201° C.; MS (ES) m/z 474.2.

Example 52

(Cyclopropylmethyl)[(6-fluoro-2,3,4,9-tetrahydro-1H-carbazol-3-yl)methyl]{[(2S)-8-methyl-2,3-dihydro[1,4]dioxino[2,3-f]quinolin-2-yl]methyl}amine dihydrochloride dihydrate The title compound was prepared by generally following the procedure of Example 50, using 0.7 mmole cyclopropanecarboxaldehyde instead of acetaldehyde. Yield=6 mg (5%), m.p. 215-230° C.; MS (ES) m/z 486.2.

Example 53

N-[(6-Fluoro-2,3,4,9-tetrahydro-1H-carbazol-3-yl) methyl]-N-{[(2S)-8-methyl-2,3-dihydro[1,4]dioxino [2,3-f]quinolin-2-yl]methyl}cyclobutanamine dihydrochloride dihydrate The title compound was prepared by generally following the procedure of Example 50, using 0.7 mmole cyclobutanone instead of acetaldehyde. Yield=6 mg (5%), m.p. 220-235° C.; MS (ES) m/z 486.2.

Example 54

N-{[(3R)-6-Fluoro-2,3,4,9-tetrahydro-1H-carbazol-3-yl]methyl}-N-{[(2S)-8-methyl-2,3-dihydro[1,4] dioxino[2,3-f]quinolin-2-yl]methyl}propan-1-amine dihydrochloride dihydrate The title compound was prepared by generally following the procedure of Example 51, using N-{[(3R)-6-fluoro-2,3, 4,9-tetrahydro-1H-carbazol-3-yl]methyl}-N-{[(2S)-8-methyl-2,3-dihydro[1,4]dioxino[2,3-f]quinolin-2-yl] methyl}amine (Example 5) instead of N-[(6-fluoro-2,3,4,9-tetrahydro-1H-carbazol-3-yl)methyl]-N-{[(2S)-8-methyl-2, 3-dihydro[1,4]dioxino[2,3-f]quinolin-2-yl]methyl}amine. Yield=74 mg (62%). mp 225-240° C.; MS (ES) m/z 472.3.

Example 55

(Cyclopropylmethyl){[(3R)-6-fluoro-2,3,4,9-tetrahydro-1H-carbazol-3-yl]methyl}{[(2S)-8-methyl-2,3-dihydro[1,4]dioxino[2,3-f]quinolin-2-yl] methyl}amine dihydrochloride dihydrate The title compound was prepared by generally following the procedure of Example 52, using N-{[(3R)-6-fluoro-2,3, 4,9-tetrahydro-1H-carbazol-3-yl]methyl}-N-{[(2S)-8-methyl-2,3-dihydro[1,4]dioxino[2,3-f]quinolin-2-yl] methyl}amine (Example 5) instead of N-[(6-fluoro-2,3,4,9-tetrahydro-1H-carbazol-3-yl)methyl]-N-{[(2S)-8-methyl-2, 3-dihydro[1,4]dioxino[2,3-f]quinolin-2-yl]methyl}amine. Yield=87 mg (73%). mp 210-225° C.; MS (ES) m/z 486.3.

Example 56

N-{[(3R)-6-Fluoro-2,3,4,9-tetrahydro-1H-carbazol-3-yl]methyl}-N-{[(2S)-8-methyl-2,3-dihydro[1,4] dioxino[2,3-f]quinolin-2-yl]methyl}cyclobutanamine dihydrochloride dihydrate The title compound was prepared by generally following the procedure of Example 53, using N-{[(3R)-6-fluoro-2,3, 4,9-tetrahydro-1H-carbazol-3-yl]methyl}-N-{[(2S)-8-methyl-2,3-dihydro[1,4]dioxino[2,3-f]quinolin-2-yl] methyl}amine (Example 5) instead of N-[(6-fluoro-2,3,4,9-tetrahydro-1H-carbazol-3-yl)methyl]-N-{[(2S)-8-methyl-2, 3-dihydro[1,4]dioxino[2,3-f]quinolin-2-yl]methyl}amine. Yield=77 mg (61%), m.p. 215-230° C.; MS (ES) m/z 486.2.

Example 57

N-{[(3R)-6-Fluoro-2,3,4,9-tetrahydro-1H-carbazol-3-yl]methyl}-N-{[(2S)-8-methyl-2,3-dihydro[1,4] dioxino[2,3-f]quinolin-2-yl]methyl}propan-2-amine monohydrochloride monohydrate The title compound was prepared by generally following the procedure of Example 54, using acetone instead of propionaldehyde. Yield=23 mg (22%), m.p. 230-243° C.; MS (ES) m/z 474.2.

Example 58

N-{[(3R)-6-Fluoro-2,3,4,9-tetrahydro-1H-carbazol-3-yl]methyl}-N-{[(2S)-8-methyl-2,3-dihydro[1,4] dioxino[2,3-f]quinolin-2-yl]methyl}butan-2-amine monohydrochloride monohydrate The title compound was prepared by generally following the procedure of Example 54, using 2-butanone instead of propionaldehyde. Yield=34 mg (31%), m.p. 235-256° C.; MS (ES) m/z 488.3.

Example 59

N-{[(3R)-6-Fluoro-2,3,4,9-tetrahydro-1H-carbazol-3-yl]methyl}-N-{[(2S)-8-methyl-2,3-dihydro[1,4] dioxino[2,3-f]quinolin-2-yl] methyl}cyclopentanamine monohydrochloride monohydrate The title compound was prepared by generally following the procedure of Example 54, using cyclopentanone instead of propionaldehyde. Yield=39 mg (35%), m.p. 225-243° C.; MS (ES) m/z 498.3.

Example 60

N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclohexanamine monohydrochloride monohydrate The title compound was prepared by generally following the procedure of Example 54, using cyclohexanone instead of propionaldehyde. Yield=9 mg (8%), m.p. 207-218° C.; MS (ES) m/z 514.3.

Example 61

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}propan-2-amine monohydrochloride monohydrate The title compound was prepared by generally following the procedure of Example 57, using S,S-(6-Fluoro-2,3,4,9-tetrahydro-1H-carbazol-3-ylmethyl)-(8-methyl-2,3-dihydro-[1,4]dioxino[2,3-f]quinolin-2-ylmethyl)-amine (example 3) instead of N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine. Yield=6 mg (6%), m.p. 228-240° C.; MS (ES) m/z 474.2.

Example 62

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}butan-2-amine monohydrochloride monohydrate The title compound was prepared by generally following the procedure of Example 61, using 2-butanone instead of acetone. Yield=61 mg (56%), m.p. 246-257° C.; MS (ES) m/z 488.3.

Example 63

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclopentanamine monohydrochloride monohydrate The title compound was prepared by generally following the procedure of Example 61, using cyclopentanone instead of acetone. Yield=67 mg (60%), m.p. 237-254° C.; MS (ES) m/z 500.3.

Example 64

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclohexanamine monohydrochloride monohydrate The title compound was prepared by generally following the procedure of Example 61, using cyclohexanone instead of acetone. Yield=4%, m.p. 202-208° C.; MS (ES) m/z 512.3.

Example 65

N-[(6-Fluoro-9-methyl-2,3,4,9-tetrahydro-1H-carbazol-3-yl)methyl]-N-([(2S)-8-methyl-2,3-dihydro[1,4]dioxino[2,3-f]quinolin-2-yl]methylpropan-2-amine monohydrochloride monohydrate The title compound was prepared by generally following the procedure of Example 61, using N-[(6-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine (example 6) instead of S,S-(6-Fluoro-2,3,4,9-tetrahydro-1H-carbazol-3-ylmethyl)-(8-methyl-2,3-dihydro-[1,4]dioxino[2,3-f]quinolin-2-ylmethyl)-amine. Yield=6%, m.p. 201-222° C.; MS (ES) m/z 488.2704.

Example 66

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclopentanamine monohydrochloride monohydrate The title compound was prepared by generally following the procedure of Example 65, using cyclopentanone instead of acetone. Yield=22%, m.p. 206-222° C.; MS (ES) m/z 514.2.

Example 67

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclohexanamine monohydrochloride monohydrate The title compound was prepared by generally following the procedure of Example 65, using cyclohexanone instead of acetone. Yield=3%, m.p. 204-225° C.; MS (ES) m/z 528.2.

Example 68

{[(3S)-6-Fluoro-9-methyl-2,3,4,9-tetrahydro-1H-carbazol-3-yl]methyl}methyl{[(2S)-8-methyl-2,3-dihydro[1,4]dioxino[2,3-f]quinolin-2-yl]methyl}amine monohydrochloride monohydrate The title compound was prepared by generally following the procedure of Example 61, using aqueous formaldehyde instead of acetone. Yield=27%, m.p. 248-258° C.; MS (ES) m/z 460.2.

Example 69

{[(3R)-6-Fluoro-9-methyl-2,3,4,9-tetrahydro-1H-carbazol-3-yl]methyl}methyl{[(2S)-8-methyl-2,3-dihydro[1,4]dioxino[2,3-f]quinolin-2-yl]methyl}amine monohydrochloride monohydrate The title compound was prepared by generally following the procedure of Example 57, using aqueous formaldehyde instead of acetone. Yield=24%, m.p. 244-256° C.; MS (ES) m/z 460.2.

Example 70a and 70b

7-Chloro-6-fluoro-2,3,4,9-tetrahydro-1H-carbazole-3-carboxylic acid (70a) and 5-chloro-6-fluoro-2,3,4,9-tetrahydro-1H-carbazole-3-carboxylic acid (70b)

3-Chloro-4-fluorophenylhydrazine hydrochloric acid (5 g, 31.137 mmole), and 4-cyclohexanone carboxylic acid ethyl ether (5 ml, 31.137 mmole) were dissolved in dioxane (80 ml). Hydrochloric acid (2M, 20 ml) was added to the solution. The mixture was refluxed for 24 hours. The reaction mixture was cooled to ambient temperature and ethyl acetate (50 ml) was added, and washed with water (50 ml, 2×). The separated organic phase was washed with brine, dried over magnesium sulfate, filtered and evaporated in vacuo. The residue was flash chromatographed on silica gel. Elution with 50-80% ethyl acetate/hexane afforded the mixture of both regioisomers, which were separated by reverse phase prep. HPLC (45 ml/min, 40-90% Acetonitrile/water at 15.6 and 16.6 minutes). The acetonitrile was evaporated in vacuo. The residue was subjected to lyophilization affording both regioisomers.

7-Chloro-6-fluoro-2,3,4,9-tetrahydro-1H-carbazole-3-carboxylic acid: (70a) 1.62 g grey solid, 39% yield. mp. 233-235° C. MS: ES [M–H]⁻ 266.1.

5-Chloro-6-fluoro-2,3,4,9-tetrahydro-1H-carbazole-3-carboxylic acid: (70b) 1.2 g grey solid, 30% yield. mp. 254-255° C. MS: ES [M–H]⁻ 266.1.

Example 71

6-Chloro-2,3,4,9-tetrahydro-1H-carbazole-3-carboxylic acid

The title compound was prepared by generally following the procedure of Example 70. Yield: 5.67 g grey solid, 81% yield. mp. 181-183° C. MS: ES [M–H]⁻ 248.1.

Example 72

6,7-Dichloro-2,3,4,9-tetrahydro-1H-carbazole-3-carboxylic acid

The title compound was prepared by generally following the procedure of Example 70. Yield: 1.51 g light-yellow solid, 23% yield. mp. 243-244° C. MS: ES [M–H]–282.0.

Example 73

5,6-Dichloro-2,3,4,9-tetrahydro-1H-carbazole-3-carboxylic acid

The title compound was prepared by generally following the procedure of example 70. Yield: 2 g yellow solid, 30% yield. mp. 244-245° C. MS: ES [M–H]⁻ 282.0.

Example 74

6-Chloro-2,3,4,9-tetrahydro-1H-carbazole-3-carboxylic acid amide

6-Chloro-2,3,4,9-tetrahydro-1H-carbazole-3-carboxylic acid (7c, 5.67 g, 22.71 mmole) dissolved THF (70 ml). N,N-carbonyldiimidazole (5.52 g, 44.81 mmole) was added. The reaction was stirred at ambient temperature for 3 hours. Ammonia was bubbled in for 1½ hours. The solid was filtered and discarded. Ethyl acetate (50 ml) was added to the filtrate and washed with citric acid 2 times, then the ethyl acetate phase was washed with 5% sodium bicarbonate and brine. The organic phase was concentrated in vacuo. The product was crystallized from the solution and filtered yielding a white solid, 4.39 g, 78%; mp. 247-248° C.

Example 75

7-Chloro-6-fluoro-2,3,4,9-tetrahydro-1H-carbazole-3-carboxylic acid amide

The title compound was prepared by generally following the procedure of Example 74. Yield: a white solid, 91% yield. mp. 245-246° C. MS: ES [M–H]⁻ 265.1.

Example 76

5-Chloro-6-fluoro-2,3,4,9-tetrahydro-1H-carbazole-3-carboxylic acid amide

The title compound was prepared by generally following the procedure of Example 74. Yield: a white solid, 94% yield. mp. 226-227° C. MS: ES [M–H]⁻ 265.1.

Example 77

6,7-Dichloro-2,3,4,9-tetrahydro-1H-carbazole-3-carboxylic acid amide

The title compound was prepared by generally following the procedure of Example 74. Yield: an off white solid, 84% yield. mp. 199-200° C. MS: ES [M–H]⁻ 281.

Example 78

5,6-Dichloro-2,3,4,9-tetrahydro-1H-carbazole-3-carboxylic acid amide

The title compound was prepared by generally following the procedure of Example 74. Yield: a light yellow solid, 81% yield. mp. 246-247° C. MS: ES [M+H]⁺ 283.

Example 79

C-(6-Chloro-2,3,4,9-tetrahydro-1H-carbazol-3-yl)-methylamine

6-Chloro-2,3,4,9-tetrahydro-1H-carbazole-3-carboxylic acid amide (0.6 g, 2.42 mmole) was dissolved in THF (20 ml). The reaction was cooled to 0° C. Lithium aluminum hydride (4.8 ml, 1M, 4.8 mmole) was portion wise carefully added. The reaction was refluxed for 2 hours. After cooling the mixture to room temperature water was carefully drop wise added to deactivate the Li—Al-complex. The formed solids were filtered and the filtrate diluted with ethyl acetate, washed with water (2×), brine and the separated organic layer dried over magnesium sulfate, filtered and evaporated in vacuo. The product was crystallized from ethyl acetate/hexane, 80:20. A white solid was obtained, 0.293 g, 52% yield. mp. 142-144° C. MS: ES [M–H]⁻ 233.1.

Example 80

C-(7-Chloro-6-fluoro-2,3,4,9-tetrahydro-1H-carbazol-3-yl)-methylamine

The title compound was prepared by generally following the procedure of Example 79. Yield: a white solid, 62% yield. mp. 180-181° C. MS: ES [M+H]⁺ 253.1.

Example 81

C-(5-chloro-6-fluoro-2,3,4,9-tetrahydro-1H-carbazol-3-yl)-methylamine

The title compound was prepared by generally following the procedure of Example 79. Yield: a white solid, 56.3% yield. mp. 179-180° C. MS: ES [M−H]⁻ 251.

Example 82

C-(6,7-dichloro-2,3,4,9-tetrahydro-1H-carbazol-3-yl)-methylamine

The title compound was prepared by generally following the procedure of Example 79. Yield: a white solid, 92% yield. mp. 156-158° C. MS: ES [M−H]⁻ 267.1.

Example 83

C-(5,6-dichloro-2,3,4,9-tetrahydro-1H-carbazol-3-yl)-methylamine

The title compound was prepared by generally following the procedure of Example 79. Yield: a off-white solid, 61.1% yield. mp. 169-170° C. MS: ES [M−H]⁻ 267.0.

Example 84

(5,6-Dichloro-2,3,4,9-tetrahydro-1H-carbazol-3-ylmethyl)-(8-methyl-2,3-dihydro-[1,4]dioxino[2,3-f]quinolin-2-ylmethyl)-amine 4-Bromo-benzenesulfonic acid-8-methyl-2,3-dihydro-[1,4]dioxino[2,3-f]quinolin-2-yl methyl ester (0.225 g, 0.5 mmole), C-(5,6-dichloro-2,3,4,9-tetrahydro-1H-carbazol-3-yl)-methylamine (9e, 0.162 g, 0.6 mmole), and 4-(dimethylamino)pyridine (0.073 g, 0.6 mmole) were dissolved in DMSO (10 ml). The reaction mixture was heated and stirred at 90° C. (bath temp.) for 18 hours. The reaction was cooled to room temperature and added drop-wise into 1% sodium bicarbonate (50 ml). The solid was filtered, dissolved in 3% methanol/ethyl acetate and flash chromatographed on silica gel. Elution with 1-5% 1M ammonia in methanol/chloroform afforded a yellow solid (0.088 g, 38% yield); mp. 245-246° C. MS: ES [M−H]⁻ 481.

Example 85

(6-Chloro-2,3,4,9-tetrahydro-1H-carbazol-3-ylmethyl)-(8-methyl-2,3-dihydro-[1,4]dioxino[2,3-f]quinolin-2-ylmethyl)-amine The title compound was prepared by generally following the procedure of Example 84. Yield: a yellow solid, 54% yield. mp. 235-237° C. MS: ES [M−H]⁻ 446.2.

Example 86

(5-Chloro-6-fluoro-2,3,4,9-tetrahydro-1H-carbazol-3-ylmethyl)-(8-methyl-2,3-dihydro-[1,4]dioxino[2,3-f]quinolin-2-ylmethyl)-amine The title compound was prepared by generally following the procedure of Example 84. Yield: a yellow solid, 18% yield. mp. 245-246° C. MS: ES [M−H]⁻ 465.

Example 87

(7-Chloro-6-fluoro-2,3,4,9-tetrahydro-1H-carbazol-3-ylmethyl)-(8-methyl-2,3-dihydro-[1,4]dioxino[2,3-f]quinolin-2-ylmethyl)-amine The title compound was prepared by generally following the procedure of Example 84. Yield: a yellow solid, 35% yield. mp. 243-244° C. MS: ES [M−H]⁻ 465.

Example 88

(6-Chloro-2,3,4,9-tetrahydro-1H-carbazol-3-ylmethyl)-(8-methyl-2,3-dihydro-[1,4]dioxino[2,3-f]quinolin-2-ylmethyl)-amine 4-Bromo-benzenesulfonic acid-8-methyl-2,3-dihydro-[1,4]dioxino[2,3-f]quinolin-2-yl methyl ester (0.225 g, 0.5 mmole) and C-(6,7-dichloro-2,3,4,9-tetrahydro-1H-carbazol-3-yl)-methylamine (9d, 0.162 g, 0.6 mmole) were dissolved in DMF (10 ml). Potassium carbonate (0.083 g, 0.6 mmole) was added and the reaction mixture stirred at 90° C. for 24 hours after which another 50 mg (0.36 mmole) of potassium carbonate was added and stirring continued at 90° C. for another 24 hours, then cooled to ambient temperature. Ethyl acetate (20 ml) was added. The organic phase was washed with water (2×), followed by brine. The separated organic layer was dried over sodium sulfate, filtered, and the solvent removed in vacuo. The residue was flash chromatographed on silica gel. Elution with 4-8% methanol/chloroform gave the crude product which was then further purified using reverse phase HPLC (30-85% acetonitrile/water at 11.33 min). The acetonitrile was evaporated in vacuo. The residue was subjected to lyophilization to afford a yellow solid (0.063 g, 26% yield); mp. 104-105° C. MS: ES [M+H]⁺ 482.2.

Example 89

6-Fluoro-2,3,4,9-tetrahydro-1H-carbazole-3-carboxylic acid

In a 5-L cylindrical reactor, p-fluorophenylhydrazine HCl (400 g, 2.46 mol) was suspended in ethanol (2B) (1.2 kg; 1.5 L). The slurry was stirred and heated to 60-65° C. A solution of 4-cyclohexanone carboxylic acid ethyl ester (400 g, 2.35 mol) in ethanol (2B) (0.4 L) was added over 1 h. The reaction temperature may rise to reflux (78-82° C.). After addition, the suspension was stirred and heated at reflux for 1 h then cooled to 40-50° C. A 50% sodium hydroxide solution (470 g) was added over 30 min. The suspension was heated to reflux (80-82° C.). (This can cause evolution of ammonium gas during heating). After 1 h, the reaction mixture was distilled at atmospheric pressure to about 1.5 L, about half of its original volume, then cooled to 60-70° C. Water (2.5 L) was added. The mixtured was cooled to 30-40° C. before dilute HCl (0.333 L conc HCl+0.667 L water) was added over 20 min. The suspension was stirred at 20° C. for 1 h then filtered through a Buchner funnel. The solid product was washed with water (3×1 L) then dried under N₂ overnight to give 534.5 g (97.5% yield) of off-white solid.

Example 90

(3S)-6-Fluoro-2,3,4,9-tetrahydro-1H-carbazole-3-carboxylic acid

In a 5-L cylindrical reactor, 6-fluoro-2,3,4,9-tetrahydro-1H-carbazole-3-carboxylic acid (300 g, 1.29 mol), and (−) cinchonidine (437 g, 1.48 mol) in isopropanol (2.7 L) are stirred at 20-25° C. for 1-2 h. The reaction mixture was cooled to 0-5° C., stirred for 3-5 h, then filtered through a Buchner funnel lined with polypropylene cloth. The solid was washed with chilled isopropanol (1 L). The mother liquor and isopropanol washes were combined and distilled down to ~⅕ its original volume (~800 mL). While the solution was at ~80-85° C., acetonitrile (3.2 L) was added over 40-60 min. The mixture was stirred at 75-80° C. for 5-10 min then cooled to 20-25° C. over 1-2 h. The mixture was stirred for 20-24 h then cooled to 10-15° C. After 1-2 h, the mixture was filtered through a Buchner funnel lined with polypropylene cloth. The solid eutomer salt was washed with chilled acetonitrile (2×300 mL) and the solid dried under vacuum under a bed of $N_2$ for 14 h to give 365 g of the desired eutomer salt (contains 3.20% distomer by chiral HPLC).

In a 5-L cylindrical reactor, the eutomer cinchonidine salt (containing 3.20% distomer) (365 g, 0.692 mol) was suspended in isopropyl alcohol (600 mL) and acetonitrile (1.8 L) was heated to 80-90° C. After 15-30 min, all the solids dissolved. The reaction mixture was cooled to 20-25° C. over 2-3 h then further cooled to 10-15° C. After 1-2 h, the mixture was filtered through a Buchner funnel lined with polypropylene cloth. The solid eutomer salt was washed with chilled acetonitrile (2×300 mL) and dry the solid under vacuum under a bed of $N_2$ for 14 h to give 256.7 g of the desired eutomer salt (contains 1.82% distomer by chiral HPLC).

In a 5-L cylindrical reactor, 3 N HCl (750 mL) was added to the eutomer cinchonidine salt (256 g, 0.485 mol) in isopropyl acetate (1.5 L) at 20-25° C. The mixture was stirred for 10-15 min then separated into two layers. The isopropyl acetate layer was set aside. The lower aqueous layer was extracted with isopropyl acetate (250 mL). The combined isopropyl acetate layers were with $H_2O$ (750 mL). Heptane (1.75 L) was added to the isopropyl acetate layer then the isopropyl acetate and heptane solution (3.7 L) was distilled under atmospheric pressure to ~¼ its original volume, approximate 1.0 L. Heptane (1 L) was added over 15-20 min at 85-90° C. then the mixture cooled to 0-5° C. over 1-2 h. The mixture was stirred at 0-5° C. for 1-2 h then filtered through a Buchner funnel lined with polypropylene cloth. The solid was washed with heptane (2×150 mL) then the product dried under vacuum under a bed of $N_2$ for 14 h to give 89.6 g (29.9% overall yield from racemic acid) of the eutomer indole acid as an off-white solid.

Example 91

(3S)-6-Fluoro-2,3,4,9-tetrahydro-1H-carbazole-3-carboxylic acid amide

Isopropyl acetate (570 mL, 488 g) was charged to a (3-L) four-necked reactor (reactor A) equipped with mechanical stirrer, condenser with nitrogen inlet, powder addition funnel, and a thermocouple. 6-fluoro-2,3,4,9-tetrahydro-1H-carbazole-3-carboxylic acid (Example 90) was charged to the reactor with stirring. The reaction mixture was cooled to 5-10° C. with an ice-bath and DMF (13.8 g) was added. Ammonium hydroxide (28% aqueous, 607 g) and water (144 g) were added to another (5-L), 4-neck reactor (reactor B) equipped with an overhead stirrer, thermocouple, and condenser under nitrogen. The contents of reactor B were cooled 5-10° C. Reactor B was connected to a caustic scrubber. Oxalyl chloride (94.3 g, 0.74 mol) was added through an addition funnel to the stirring slurry in reactor A maintaining temperature between 5 and 15° C. The funnel was rinsed with 50 mL of isopropyl acetate and the reaction mixture was allowed to warm to 10-15° C. The reaction mixture was stirred for an additional 30 min after addition of oxalyl chloride and an aliquot (3 drops) of the reaction mixture was quenched with 0.11 mL of 28% aq. ammonium hydroxide then diluted with $CH_3CN$ to 2 mL, and monitored for disappearance of the acid by HPLC (<10-11 area % of the acid). When the reaction was complete, the contents of reactor A were cooled to 5-10° C. The acid chloride from reactor A was transferred to the cooled ammonium hydroxide solution in reactor B over 30 min to 45 min maintaining temperature between 5-15° C. followed by a 50 mL isopropyl acetate rinse. The reaction mixture was stirred at 5-10° C. for 30 min when solids separated out. Heptane (540 mL) was charged at 10-15° C. and stirring continued for 30 min. The slurry was filtered through a funnel lined with polypropylene and the collected solid washed with 800 mL of cold water followed by 800 mL of n-heptane. The solid was dried under vacuum (<20 mm Hg) at 40° C. to give 140.4 g of 6-fluoro-2,3,4,9-tetrahydro-1H-carbazole-3-carboxylic acid amide (94% yield). Chiral purity is 99.4% by HPLC and MW 232(LC/MS).

Example 92

{[(3S)-6-Fluoro-2,3,4,9-tetrahydro-1H-carbazol-3-yl]methyl}-amine

In a 5-L round-bottomed flask with lithium aluminum hydride pellets (35.5 g, 0.935 mol) in THF (800 mL), the mixture was vigorously stirred for 40 min. This was heated to 50-52° C. then a slurry of indole amide (105 g, 0.45 mol) in THF (600 mL) was added over 1.5 h. Additional LAH pellets (2.8 g, 0.074 mol) were added. The reaction mixture was heated to reflux, 65-67° C. for 1-2 h. The reaction mixture was cooled to 0-5° C. over 1 h. Water (39 mL) was added over 15-20 min then the mixture stirred for 5-10 min. 15% NaOH (39 mL) was added over 5-10 min then the mixture stirred for 5-10 min. Water (117 mL) was added over 5-10 min then the mixture warmed to 15-20° C. and stirred for 15-20 min. The slurry was filtered through a Buchner funnel lined with polypropylene cloth. The solids were washed with THF (400 mL), the THF solutions combined and distilled down to ~¼ its original volume, (300 mL). Cyclohexane (200 mL) was added at 80-85° C. over 10-15 min then the mixture distilled to 300 mL. Another portion of cyclohexane (200 mL) was added and then the mixture distilled down to 200 mL. The mixture was stirred at 20-25° C. for 3 h then the slurry filtered through a Buchner funnel lined with polypropylene cloth. The solid was washed with cyclohexane (60 mL), dried in a vacuum oven to give 80.3 g (82% yield) of indole amine as an off-white solid.

Example 93

N-{[(3S)-6-fluoro-2,3,4,9-tetrahydro-1H-carbazole-3-yl]methyl}-N-{[(2S)-8-methyl-2,3-dihydro[1,4]dioxino[2,3-f]quinolin-2-yl]methyl}amine maleic acid salt Butyronitrile (1.71 kg) was charged to a (5.0 L) cylindrical reactor equipped with an overhead stirrer, temperature controller, thermocouple, and reflux condenser (reactor A). To the reaction vessel, under nitrogen was charged sequentially, {[(3S)-6-Fluoro-2,3,4,9-tetrahydro-1H-carbazol-3-yl]methyl}-amine (180 g, 0.82 mole) (Example 92), potassium carbonate (110.5 g. 0.8 mole) and quinaldine brosylate (400.8 g, 0.9 mole) (prepared according to the procedure described in U.S. Pat. No. 6,693,197 B1). The slurry was heated with stirring under positive nitrogen pressure to 95±5° C. for 27 h. After completion of the reaction, the mixture was cooled to 22±5° C. Water (1100 mL) was charged and stirred for 10 min. The layers are separated and the aqueous layer discarded. Ammonium chloride solution was added and stirred. The layers are separated and the organic phase was washed once more with ammonium chloride solution (2% aqueous, 1100 mL). The layers were separated and the organic phase warmed to 40±5° C. in reactor A. A solution of maleic acid (119 g, 1.02 moles) in 2-propanol (0.7 L) was prepared by warming to 40±5° C. in a separate (2-L) reactor (reactor B). The warm maleic acid solution was added slowly to the butyronile solution in reactor A maintaining the temperature between 40 to 45° C. The solution was slowly cooled 20 to 25° C. and stirred for 16 h when solids separated out. The solids were filtered through a funnel lined with polypropylene and washed with 2-propanol (0.60 L). The wet solids from the funnel were transferred to ethanol (grade 2B, 2.5 L) in reactor A and warmed to 40 to 45° C. with stirring for 30 min. The slurry was cooled to 22 to 25° C. and stirred for an additional 2 h. The solids were filtered through a funnel lined with polypropylene and washed with ethanol (grade 2B, 1.7 L). The solid was dried under vacuum (<20 mm Hg) at 40° C. to give 330 g of maleic acid salt of N-{[(3S)-6-fluoro-2,3,4,9-tetrahydro-1H-carbazole-3-yl]Methyl}-N-{[(2S)-8-methyl-2,3-dihydro[1,4]Dioxino[2,3-f]Quinolin-2-yl]methyl}amine (73% yield). Purity by HPLC is 97.4% (diastereomer content 2.1%), MW 431 (LC/MS).

Example 94

N-{[(3S)-6-fluoro-2,3,4,9-tetrahydro-1H-carbazole-3-yl]methyl}-N-{[(2S)-8-methyl-2,3-dihydro[1,4]dioxino[2,3-f]quinolin-2-yl]methyl}amine Ethanol (grade 2B, 8.0 L) was charged to a charged to a (22-L) reactor equipped with an overhead stirrer, temperature controller, thermocouple, and reflux condenser. N-{[(3S)-6-fluoro-2,3,4,9-tetrahydro-1H-carbazole-3-yl]methyl}-N-{[(2S)-8-methyl-2,3-dihydro[1,4]Dioxino[2,3-f]quinolin-2-yl]methyl}amine maleic acid salt, (800 g, 1.46 mole) (Example 93), was added to the reactor followed by solid potassium carbonate (325 mesh, 222 g, 1.6 mole). The slurry was heated with stirring under nitrogen at 49 to 52° C. for 1 h. The reaction mixture was allowed to cool to 20 to 24° C., stirred for 2 h and the solids were filtered through a funnel lined with polypropylene. The filter cake was washed with ethanol (grade 2B, 8.0 L). The combined ethanol filtrate and washes were concentrated to a volume of 2.8 to 3.0 L at 40 to 45° C. and 45-60 mm Hg. The concentrate was stirred for 20 h at 20-25° C. when solids separate out. Water (1 L) was added to the slurry and stirred for another 4 h at 20-25° C. followed by stirring for an additional 3 h at 10 to 15° C. The solids are filtered and the cake washed with a mixture of ethanol (grade 2B, 0.1 L) and water (0.7 L). The solid was dried under vacuum (<20 mm Hg) at 40° C. to give 469 g of N-{[(3S)-6-fluoro-2,3,4,9-tetrahydro-1H-carbazole-3-yl]Methyl}-N-{[(2S)-8-methyl-2,3-dihydro[1,4]Dioxino[2,3-f]Quinolin-2-yl]methyl}amine (74% yield). Purity by HPLC is 98.5% (diastereomer content 1.1%), MW 431 (LC/MS).

Example 95a and 95b (7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(S)-ylmethyl)-amine (95a) and (7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(R)-ylmethyl)-amine (95b)

2,3-dihydro-7H-[1,4]dioxino[2,3-e]indol-2-ylmethyl 4-methylbenezensulfonate (0.176 g, 0.490 mmol) (synthesized according to a procedure described in U.S. Pat. App. No. 2003/0134870) was dissolved in 1.5 mL DMF. C-(6-fluoro-2,3,4,9-tetrahydro-1H-carbazol-3-yl)-methylamine (0.107 g, 0.490 mmol) (Example 16) was added, followed by sodium bicarbonate (0.052 g, 0.619 mmol). The mixture was heated to 70° C. overnight (~16 hours). The mixture was partitioned between ethyl acetate and water. The organic layer was washed with brine, dried (MgSO$_4$) and evaporated. Chromatography on silica gel using a gradient elution of 0-5% methanol in methylene chloride gave the products (0.163 g, 0.402 mmol) as a mixture of diastereomers. This mixture was separated using preparatory chiral HPLC (eluting with ethanol) to afford two products. The first product to elute (0.048 g) was dissolved in 1 mL ethanol and treated with 119 uL 1N HCl. The material was evaporated to afford a solid that appeared to contain ~20% of an impurity. The material was taken up in 1 mL ethanol and warmed slightly with a heat gun. The material did not completely dissolve, and was placed in a –20° C. freezer for three days. The solids were filtered, washed with a small amount of ether, and pumped dry to afford (7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(S)-ylmethyl)-amine (95a) as an olive solid. MS (ESI) m/e 404.2 [M–H]–.

The second product to elute from the preparatory chiral HPLC (0.043 g) was taken up in 1 mL ethanol and 106 uL of 1N HCl was added. The material was pumped dry to afford (7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(R)-ylmethyl)-amine (95b) (0.043 g) as an off-white solid. MS (ESI) m/e 406.1 [M+H]+.

Example 96a and 96b (2,3-Dihydro-1,4-dioxa-5,8-diaza-phenanthren-3-(S)-ylmethyl)-(6-fluoro-2,3,4,9-tetrahydro-1H-carbazol-3-(R)-ylmethyl)-amine (96a) and (2,3-Dihydro-1,4-dioxa-5,8-diaza-phenanthren-3-(S)-ylmethyl)-(6-fluoro-2,3,4,9-tetrahydro-1H-carbazol-3-(S)-ylmethyl)-amine (96b)

2,3-dihydro[1,4]dioxino[2,3-f]quinoxalin-2-ylmethyl 4-methylbenzenesulfonate (0.082 g, 0.220 mmol) (synthesized according to a procedure described in U.S. Pat. App. No. 2004/0077652) was dissolved in 0.8 mL DMSO. C-(6-fluoro-2,3,4,9-tetrahydro-1H-carbazol-3-yl)-methylamine (0.048 g, 0.220 mmol) (Example 16) was added, followed by sodium bicarbonate (0.019 g, 0.230 mmol). The mixture was heated to 80° C. overnight (~16 hours). The mixture was partitioned between ethyl acetate and water. The aqueous layer was extracted with ethyl acetate, and the combined organic extracts were washed with brine, dried (MgSO$_4$) and evaporated. Chromatography on silica gel using a gradient elution of 10%-15% ethyl acetate in methylene chloride, followed by 15% ethyl acetate/methylene chloride with 1% methanol, then followed by 15% ethyl acetate/methylene chloride with 2% methanol gave the products (0.054 g, 0.129 mmol) as a mixture of diastereomers. This mixture was separated using preparatory chiral HPLC (eluting with ethanol) to afford two products. The first product to elute (0.018 g) was dissolved in ~0.4 mL methanol and treated with 86 uL 1N HCl. The material was stirred for ~5 minutes and evaporated to afford 2,3-Dihydro-1,4-dioxa-5,8-diaza-phenanthren-3-(S)-ylmethyl)-(6-fluoro-2,3,4,9-tetrahydro-1H-carbazol-3-(R)-ylmethyl)-amine (96a) as a brown solid. MS (ESI) m/e 419.2 [M+H]+, 441.2 [M+Na]+.

The second product to elute (0.014 g) was dissolved in ~0.4 mL methanol and treated with 86 uL 1N HCl. The material was stirred for ~5 minutes and evaporated to afford (2,3-Dihydro-1,4-dioxa-5,8-diaza-phenanthren-3-(S)-ylmethyl)-(6-fluoro-2,3,4,9-tetrahydro-1H-carbazol-3-(S)-ylmethyl)-amine (96b) as a brown solid. MS (ESI) m/e 419.2 [M+H]+, 441.1 [M+Na]+.

Example 97a and 97b

Toluene-4-sulfonic acid 7-methyl-2,3-dihydro-1,4-dioxa-5,8-diaza-phenanthren-3-ylmethyl ester (97a) and Toluene-4-sulfonic acid 6-methyl-2,3-dihydro-1,4-dioxa-5,8-diaza-phenanthren-3-ylmethyl ester (97b)

[7,8-diamino-2,3-dihydro-1,4-benzodioxin-2-yl]methyl 4-methylbenzenesulfonate dihydrochloride (0.458 g, 1.31 mmol) (synthesized according to a procedure described in U.S. Pat. App. No. 2004/0077652) was dissolved in 10 mL ethanol and 10 mL water. Methyl glyoxal (40% by wt. in water, 202 uL, 1.31 mmol) was added, the mixture heated to 60° C. for three hours, and then allowed to stir at room temperature for 2 days. The mixture was partitioned between ethyl acetate and half-saturated brine. The aqueous layer was extracted with ethyl acetate, and the combined organic extracts were washed with brine, dried (MgSO$_4$) and evaporated. Chromatography on silica gel using a gradient elution of ethyl acetate in methylene chloride, gave the title compounds 97a and 97b (0.274 g, 0.710 mmol) as a mixture of isomers. This mixture was separated using preparatory chiral HPLC (eluting with methanol) to afford two products. The first product to elute (0.099 g) was toluene-4-sulfonic acid 7-methyl-2,3-dihydro-1,4-dioxa-5,8-diaza-phenanthren-3-ylmethyl ester (97a) based on $^1$H NMR HMBC experiments. The second product to elute (0.164 g) toluene-4-sulfonic acid 6-methyl-2,3-dihydro-1,4-dioxa-5,8-diaza-phenanthren-3-ylmethyl ester (97a).

Example 98a and 98b (6-Fluoro-2,3,4,9-tetrahydro-1H-carbazol-3-(R)-ylmethyl)-(7-methyl-2,3-dihydro-1,4-dioxa-5,8-diaza-phenanthren-3-(S)-ylmethyl)-amine (98a) and (6-Fluoro-2,3,4,9-tetrahydro-1H-carbazol-3-(S)-ylmethyl)-(7-methyl-2,3-dihydro-1,4-dioxa-5,8-diaza-phenanthren-3-(S)-ylmethyl)-amine (98b)

Toluene-4-sulfonic acid 7-methyl-2,3-dihydro-1,4-dioxa-5,8-diaza-phenanthren-3-ylmethyl ester (0.095 g, 0.246 mmol) (Example 97a) was dissolved in 0.8 mL anhydrous DMSO. C-(6-fluoro-2,3,4,9-tetrahydro-1H-carbazol-3-yl)-methylamine (0.054 g, 0.246 mmol) (Example 16) and sodium bicarbonate (0.026 g, 0.310 mmol) were added, and the mixture was heated to 80° C. for sixteen hours. The mixture was partitioned between ethyl acetate and water. The aqueous layer was extracted with ethyl acetate, and the combined organic layer was washed with brine, dried (MgSO$_4$) and evaporated. Chromatography on silica gel using a gradient elution of 0-4% methanol in methylene chloride gave the products (0.059 g, 0.137 mmol) as a mixture of diasereomers. This mixture was separated using preparatory chiral HPLC (eluting with ethanol) to afford two products. The first product to elute (0.033 g) was dissolved in 0.4 mL ethanol and treated with 76 uL 1N HCl. The material was evaporated to afford (6-Fluoro-2,3,4,9-tetrahydro-1H-carbazol-3-(R)-ylmethyl)-(7-methyl-2,3-dihydro-1,4-dioxa-5,8-diaza-phenanthren-3-(S)-ylmethyl)-amine (98a) (0.020 g, 0.043 mmol; some material lost during evaporation) as a burgundy solid. MS (ESI) m/e 433.2 [M+H]+, 455.2 [M+Na]+.

The second product to elute from the preparatory chiral HPLC (0.024 g) was taken up in 0.4 mL ethanol and 56 uL of 1N HCl was added. The material was pumped dry to afford (6-Fluoro-2,3,4,9-tetrahydro-1H-carbazol-3-(S)-ylmethyl)-(7-methyl-2,3-dihydro-1,4-dioxa-5,8-diaza-phenanthren-3-(S)-ylmethyl)-amine (98b) (0.024 g, 0.051 mmol) as a grey solid. MS (ESI) m/e 433.2 [M+H]+, 455.2 [M+Na]+.

Example 99a and 99b (6-Fluoro-2,3,4,9-tetrahydro-1H-carbazol-3-(R)-ylmethyl)-(6-methyl-2,3-dihydro-1,4-dioxa-5,8-diaza-phenanthren-3-(S)-ylmethyl)-amine (99a) and (6-Fluoro-2,3,4,9-tetrahydro-1H-carbazol-3-(S)-ylmethyl)-(6-methyl-2,3-dihydro-1,4-dioxa-5,8-diaza-phenanthren-3-(S)-ylmethyl)-amine (99b)

Toluene-4-sulfonic acid 6-methyl-2,3-dihydro-1,4-dioxa-5,8-diaza-phenanthren-3-ylmethyl ester (0.099 g, 0.256 mmol) (Example 97b) was dissolved in 0.8 mL anhydrous DMSO. C-(6-fluoro-2,3,4,9-tetrahydro-1H-carbazol-3-yl)-methylamine (0.056 g, 0.256 mmol) (Example 16) and sodium bicarbonate (0.027 g, 0.321 mmol) were added, and the mixture was heated to 80° C. for sixteen hours. The mixture was partitioned between ethyl acetate and water. The aqueous layer was extracted with ethyl acetate, and the combined organic layer was washed with brine, dried (MgSO$_4$) and evaporated. Chromatography on silica gel using a gradient elution of 5% ethyl acetate/methylene chloride with 0.5% Et$_3$N, then 15% ethyl acetate/methylene chloride with 0.5% Et$_3$N, then 15% ethyl acetate/methylene chloride with 0.5% Et$_3$N and 1% methanol, and finally 15% ethyl acetate/methylene chloride with 0.5% Et$_3$N and 2% methanol gave the products (0.030 g, 0.069 mmol) as a mixture of diastereomers. This mixture was separated using preparatory chiral HPLC (eluting with ethanol) to afford two products. The first product to elute (0.011 g) was dissolved in 0.3 mL methanol and treated with 25 uL 1N HCl. The material was evaporated to afford (6-Fluoro-2,3,4,9-tetrahydro-1H-carbazol-3-(R)-ylmethyl)-(6-methyl-2,3-dihydro-1,4-dioxa-5,8-diaza-phenanthren-3-(S)-ylmethyl)-amine (99a) (0.012 g, 0.026 mmol) as a light orange solid. MS (ESI) m/e 433.1 [M+H]+, 455.1 [M+Na]+.

The second product to elute from the preparatory chiral HPLC (0.010 g) was taken up in 0.3 mL methanol and 24 uL of 1N HCl was added. The material was pumped dry to afford (6-Fluoro-2,3,4,9-tetrahydro-1H-carbazol-3-(S)-ylmethyl)-(6-methyl-2,3-dihydro-1,4dioxa-5,8-diaza-phenanthren-3-(S)-ylmethyl)-amine (99b) (0.011 g, 0.023 mmol) as a light orange solid. MS (ESI) m/e 433.1 [M+H]+, 455.1 [M+Na]+.

Example 100a and 100b

N-{[(3S)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine (100a) and N-{[(3R)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine (100b)

2,3,4,9-tetrahydro-1H-carbazole-3-carboxylic acid ethyl ester

4-Cyclohexanonecarboxylic acid ethyl ester (25 g, 147 mmol) and phenylhydrazine hydrochloride (20 g, 139 mmol) were refluxed in 550 mL of anhydrous ethanol overnight. The reaction was cooled and concentrated in vacuo. The residue was partitioned between ethyl acetate and water, then the organic layer was dried over sodium sulfate, filtered, and concentrated in vacuo. Purification by flash chromatography on silica gel afforded 34.5 g (96%) of the title compound.

2,3,4,9-tetrahydro-1H-carbazole-3-carboxylic acid 2,3,4,9-tetrahydro-1H-carbazole-3-carboxylic acid ethyl ester (34.5 g, 142 mol) was dissolved in 375 mL of THF. Lithium hydroxide hydrate (23.8 g, 566 mmol) was added. The mixture was stirred at room temperature 48 h, at which time TLC showed complete consumption of starting ester. The mixture was acidified with 1 N HCl and was extracted with ethyl acetate. The organic layer was washed with brine, then was dried over sodium sulfate, filtered, and concentrated in vacuo to afford 30.4 g (99%) of the title compound.

2,3,4,9-tetrahydro-1H-carbazole-3-carboxamide 2,3,4,9-tetrahydro-1H-carbazole-3-carboxylic acid (30.4 g, 141 mmol), was suspended in 450 ml of methylene chloride and cooled to 0° C. Oxalyl chloride (14.8 mL, 169 mmol) was added dropwise, followed by two drops of DMF. The resulting mixture was allowed to warm to room temperature and was stirred for 24 h. After re-cooling to 0° C., 450 mL of conc. aqueous ammonium hydroxide were added dropwise. The yellow precipitate that formed was collected by vacuum filtration. After drying, the title compound weighed 17.4 g (58%).

[(2,3,4,9-tetrahydro-1H-carbazole-3-carbazol-3-yl)methyl]amine

To a solution of 2,3,4,9-tetrahydro-1H-carbazole-3-carboxamide (2.14 g, 10 mmol) in 50 mL of anhydrous THF were added 20 mL of 1 N lithium aluminum hydride in THF. The resulting mixture was refluxed for 3.5 h, then was cooled to room temperature and was treated with a saturated aqueous solution of sodium potassium tartrate. The mixture was diluted further with water and extracted with ethyl acetate. The organic layer was washed with saturated aqueous sodium bicarbonate and with brine. The organic layer was dried over sodium sulfate, filtered and concentrated in vacuo to afford 1.95 g (97%) of the title compound as a tan solid.

N-{[2,3,4,9-tetrahydro-1H-carbazol-3-yl]methyl}-N-[(2S)-8-methyl-2,3-dihydro[1,4]dioxino[2,3-f]quinolin-2-yl]methyl}amine A mixture of racemic [(2,3,4,9-tetrahydro-1H-carbazole-3-carbazol-3-yl)methyl]amine (0.5 g, 2.5 mmol), [(2R)-8-methyl-2,3-dihydro[1,4]dioxino[2,3-f]quinolin-2-yl]methyl 4-bromobenzenesulfonate (0.75 g, 1.67 mmol), and dimethylaminopyridine (0.2 g, 1.67 mmol) in 5 ml of anhydrous DMSO was heated at 90° C. for 4 h. The resulting mixture was cooled, diluted with ethyl acetate, and poured into aqueous sodium bicarbonate. The organic layer was separated and the aqueous-layer was further extracted with ethyl acetate. The combined organic layers were washed with brine and water, then were dried over sodium sulfate, filtered, and concentrated in vacuo. The resulting solid was suspended in ethyl acetate and filtered through a plug of silica gel to remove baseline impurities. Further purification by chromatography on silica gel (ethyl acetate/hexane gradient) afforded 250 mg of the title compound as a mixture of two diastereomers. The diastereomers were separated by HPLC on a Chiracel AD-H column (2×25 cm), eluting with 0.1% diethylamine in methanol.

Diastereomer 1: 50 mg of the amine was isolated and converted into its di-hydrochloride salt by treating a methanolic solution of the amine with 242 μL of 1 N HCl in ether. The yellow solid was collected by vacuum filtration, washed with ethyl acetate and hexane, and dried under vacuum to afford N-{[(3S)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine as a yellow powder; mp 202-205 (d); MS (ES) m/z=414 [M+H]+.

Diastereomer 2: 30 mg of the amine was isolated and converted into its di-hydrochloride salt by treating a methanolic solution of the amine with 145 μL of 1 N HCl in ether. The yellow solid was collected by vacuum filtration, washed with ethyl acetate and hexane, and dried under vacuum to afford N-{[(3R)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine as a yellow powder; mp 218-221 (d); MS (ES) m/z=414 [M+H]+.

Example 101

(3R)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine

Benzyl [(3R)-6-fluoro-2,3,4,9-tetrahydro-1H-carbazol-3-yl]carbamate

To a solution of (3R)-6-Fluoro-2,3,4,9-tetrahydro-1H-carbazole-3-carboxylic acid (0.60 g, 2.57 mmol) in anhydrous 1,4-dioxane (20 mL) was added diphenylphosphorylazide (0.7 mL, 3.24 mmol), triethylamine (0.39 mL, 2.83 mmol), and 4 A molecular sieves. After stirring at room temperature for 2 h, benzyl alcohol (0.8 mL, 7.71 mmol) was added and the reaction was heated at 70° C. for 2 h. After cooling, the mixture was filtered and the filtrate was concentrated in vacuo. Purification by chromatography on silica gel afforded 340 mg of the title compound as a colorless oil.

(3R)-6-fluoro-2,3,4,9-tetrahydro-1H-carbazol-3-amine

To a solution of benzyl [(3R)-6-fluoro-2,3,4,9-tetrahydro-1H-carbazol-3-yl]carbamate (240 mg, 0.71 mmol) in ethanol was added 20 mg of 10% palladium on carbon. Hydrogenation at 50 psi overnight, followed by filtration and concentration of the filtrate, afforded 160 mg of the title compound as an off-white solid.

(3R)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine Using essentially the same method as described above for Example 100, the title compound (60 mg) was prepared and isolated as its dihydrochloride salt as a yellow solid; mp 232-234° C.; MS (ES) m/z=418.2 [M+H]+; [α]$_D$=+3.80 (1% solution in DMSO).

Example 102

(3S)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine The title compound was prepared using the same sequence of reactions as described for Example 101, starting from (3S)-6-fluoro-2,3,4,9-tetrahydro-1H-carbazole-3-carboxylic acid. The title compound was isolated as its dihydrochloride salt: mp 230-235° C. (d); MS (ES) m/z=418.2 [M+H]+; [α]$_D$=−62.47° (1% solution in DMSO).

Example 103

[(2S)-2,3-dihydro[1,4]dioxino[2,3-f]quinolin-2-ylmethyl]{[(3R)-6-fluoro-2,3,4,9-tetrahydro-1H-carbazol-3-yl]methyl}amine and [(2S)-2,3-dihydro[1,4]dioxino[2,3-f]quinolin-2-ylmethyl]{[(3S)-6-fluoro-2,3,4,9-tetrahydro-1H-carbazol-3-yl]methyl}amine To a solution of C-(6-fluoro-2,3,4,9-tetrahydro-1H-carbazol-3-yl)-methylamine (0.170 g, 0.76 mmols) and [(2R)-2,3-dihydro[1,4]dioxino[2,3-f]quinolin-2-yl]methyl 4-methylbenzenesulfonate (0.120 g, 0.55 mmols) in DMSO (4 mL), triethylamine (0.128 mL, 0.92 mmols) was added and the reaction was heated at 90° C. for 5.5 h. After cooling to room temperature, the mixture was partitioned between ethyl acetate and saturated sodium bicarbonate solution. The organic phase was removed, dried with magnesium sulfate and concentrated to dryness. The residue was chromatographed on silica gel with 1-4% methanol in dichloromethane to give a mixture of diastereomers. The diastereomers were separated by HPLC, isolated as free base, and converted to the dihydrochloride salt to generate:

Diastereomer 1: MS (ES) m/z 416.2; [α]D25=−61.00° (c=1% solution, DMSO).

Diastereomer 2: MS (ES) m/z 416.2; [α]D25=−4.00 (c=1% solution, DMSO).

Example 104a and 104b

(8R)-8-[({[(2S)-8-methyl-2,3-dihydro[1,4]dioxino[2,3-f]quinolin-2-yl]methyl}amino)methyl]-6,7,8,9-tetrahydrodibenzo[b,d]thiophene-2-carbonitrile (104a) and (8S)-8-[({[(2S)-8-methyl-2,3-dihydro[1,4]dioxino[2,3-f]quinolin-2-yl]methyl}amino)methyl]-6,7,8,9-tetrahydrodibenzo[b,d]thiophene-2-carbonitrile (104b)

Step 1: Ethyl 4-[(4-bromophenyl)thio]-3-oxocyclohexanecarboxylate

To a solution of 4-bromobenzenethiol (2.92 g, 15.45 mmol) in 20 mL acetone was added K$_2$CO$_3$ (2.2 g, 15.18 mmol) and a solution of ethyl 4-bromo-3-oxocyclohexanecarboxylate (3.73 g, 15 mmol) in acetone (10 mL). The resulting suspension was stirred at room temperature for 2 hour, and then was partitioned between water and hexane. The organic layer was washed with water, then brine, then was dried over MgSO$_4$, filtered, and concentrated. Purification by chromatography on silica gel (15% EtOAc in hexane) afforded 3.4 g (61%) of the title compound as an oil: MS (ES) m/z=356 [M]+.

Step 2: Ethyl 8-bromo-1,2,3,4-tetrahydrodibenzo[b,d]thiophene-2-carboxylate Using essentially the same procedure described above for Example 23 (intermediate 6), 1.76 g of the title compound was prepared in 55% yield, as a foam: MS (ES) m/z=338 [M]+.

Step 3: Ethyl 8-cyano-1,2,3,4-tetrahydrodibenzo[b,d]thiophene-2-carboxylate To a solution of ethyl 8-bromo-1,2,3,4-tetrahydrodibenzo[b,d]thiophene-2-carboxylate (0.62 g, 1.83 mmol) in 10 mL 1-methylpyrrolidin-2-one was added CuCN (0.328 g, 3.66 mmol). The reaction was heated at 170° C. overnight, then was cooled to room temperature and was partitioned between EtOAc and water. The organic layer was washed with water, then brine, then dried over MgSO$_4$, filtered and concentrated. Purification by chromatography on silica gel (25% EtOAc in hexane) afforded 0.46 g (88%) of the title compound as a white solid: mp 121-122° C.; MS (ES) m/z=285 [M]+.

Step 4: 8-(Hydroxymethyl)-6,7,8,9-tetrahydrodibenzo[b,d]thiophene-2-carbonitrile To a room temperature solution of ethyl 8-cyano-1,2,3,4-tetrahydrodibenzo[b,d]thiophene-2-carboxylate (0.72 g, 2.53 mmol) in THF (4 mL) was added LiBH$_4$ (6.33 mL of 2 N solution in THF, 12.66 mmol). The reaction was heated at reflux for 5.5 hour, then was cooled in ice water, and quenched with 7 mL of 1 N NaOH (aq) solution. After stirring for a few minutes at room temperature, the mixture was extracted with EtOAc. The organic layer was washed with water, then brine, then was dried over MgSO$_4$, filtered, and concentrated. Purification by chromatography on silica gel (50% EtOAc in hexane) afforded 0.24 g (39%) of the title compound as a white solid: mp 165-166° C.; MS (ES) m/z=243 [M]+.

Step 5: 8-Formyl-6,7,8,9-tetrahydrodibenzo[b,d]thiophene-2-carbonitrile

To a room temperature suspension of 8-(hydroxymethyl)-6,7,8,9-tetrahydrodibenzo[b,d]thiophene-2-carbonitrile (0.24 g, 1 mmol) in 4 mL CH$_2$Cl$_2$ was added TFA (0.5 mL). To the resulting homogeneous solution was added Dess-Martin periodinane (0.243 g, 1 mmol). Precipitates were formed after reaction mixture was stirred for 10 minutes. The resulting suspension was cooled in ice water, and diluted with EtOAc (15 mL), then was treated with 10 mL of 1.25 N NaOH (aq.) solution. After stirring for a few minutes, the organic layer was collected, washed with water, then brine, then was dried over MgSO$_4$), filtered, and concentrated. Purification by chromatography on silica gel (25% EtOAc in hexane) afforded 0.14 g (58%) of the title compound as a white solid: mp 172-173° C.; MS (ES) m/z=241 [M]+.

Step 6: (8R)-8-[({[(2S)-8-methyl-2,3-dihydro[1,4]dioxino[2,3-f]quinolin-2-yl]methyl}amino)methyl]-6,7,8,9-tetrahydrodibenzo[b,d]thiophene-2-carbonitrile and (8S)-8-[({[(2S)-8-methyl-2,3-dihydro[1,4]dioxino[2,3-f]quinolin-2-yl]methyl}amino)methyl]-6,7,8,9-tetrahydrodibenzo[b,d]thiophene-2-carbonitrile To a solution of 1-[(2S)-8-methyl-2,3-dihydro[1,4]dioxino[2,3-f]quinolin-2-yl]methanamine (110 mg, 0.48 mmol) in MeOH (6 mL) was added 8-formyl-6,7,8,9-tetrahydrodibenzo[b,d]thiophene-2-carbonitrile (116 mg, 0.48 mmol), NaCNBH$_3$ (60.3 mg, 0.96 mmol) and glacial acetic acid (69 mg, 1.15 mmol). The reaction mixture was stirred at room temperature for 2 hour, then was cooled in ice bath, basified with saturated aqueous Na$_2$CO$_3$ solution, and stirred for a few minutes. Methanol was removed by vacuum. The resulting suspension was diluted with water and extracted with EtOAc. The organic layer was washed with water, then brine, then was dried over MgSO$_4$, filtered and concentrated. Purification by chromatography on silica gel (70/20/5 EtOAc/Hexane/NH$_3$ in MeOH [sat'd solution]) afforded 0.162 g (74%) of a white solid. Chiral HPLC separation afforded two diastereomers, which were convereted to their dihydrochloride salts:

Diastereomer 1: 30 mg of yellow solid: mp 225-230° C., MS (ES) m/z=456 [M+H]$^+$; [α]$_D$=−139° (1% solution in MeOH).

Diastereomer 2: 4 mg of yellow solid: mp 225-230° C., MS (ES) m/z=456 [M+H]$^+$; [α]$_D$=−14.0° (1% solution in MeOH).

Example 105a and 105b

1-[(2R)-8-fluoro-1,2,3,4-tetrahydrodibenzo[b,d]furan-2-yl]-N-([(2S)-8-methyl-2,3-dihydro[1,4]dioxino[2,3-f]quinolin-2-yl]methyl{methanamine (105a) and 1-[(2S)-8-fluoro-1,2,3,4-tetrahydrodibenzo[b,d]furan-2-yl]-N-{[(2S)-8-methyl-2,3-dihydro[1,4]dioxino[2,3-f]quinolin-2-yl]methyl}methanamine (105b)

Step 1: 6-fluoro-3-nitro-2H-chromen-2-one

5-Fluoro-2-hydroxybenzaldehyde (7.14 g, 50.96 mmol), diethyl amine hydrochloride (6.70 g, 61.15 mmol) and methyl nitroacetate (5.62 mL, 61.15 mmol) were added together in toluene (90 mL) and stirred together at reflux under a N$_2$ atmosphere. A Dean-Stark apparatus was fitted to the system to remove the H$_2$O generated by the reaction. The reaction was allowed to reflux overnight, after which the mixture was cooled and diluted with H$_2$O. The organic layer was separated, washed with brine, dried over anhydrous Na$_2$SO$_4$ and concentrated. Purification by flash chromatography on silica gel afforded the product as an orange solid (5.90 g, 55%)

Step 2: (6aR,10aS)-2-fluoro-9-methoxy-6a-nitro-6a,7,10,10a-tetrahydro-6H-benzo[c]chromen-6-one 6-fluoro-3-nitro-2H-chromen-2-one (8.50 g, 40.66 mmol) and 2,2-dimethoxy-1-butene (10.2 g, 120 mmol) were stirred together in dichloroethane (100 mL) at reflux under a N$_2$ atmosphere for 1 h. TLC (25% EtOAc in hexanes) indicated reaction was complete, so reaction mixture was cooled to room temperature, and concentrated under reduced pressure. The resulting brown solid was purified by flash chromatography on silica gel to afford the title compound as an off-white solid (7.50 g, 63%); MS (APPI) m/z=294 [M+H]+.

Step 3:
8-fluoro-3,4-dihydrodibenzo[b,d]furan-2(1H)-one

To a 250 mL flask were added CTABr (0.933 g, 2.56 mmol), NaOH (23.04 g, 576 mmol), and H$_2$O (100 mL), and the resulting solution was warmed to 50° C. (6aR,10aS)-2-fluoro-9-methoxy-6a-nitro-6a,7,10,10a-tetrahydro-6H-benzo[c]chromen-6-one (3.75 g, 12.80 mmol) was rapidly added to the alkaline solution and left under stirring for 1 h. The green solution was then cooled to 0° C., and added dropwise to a solution of H$_2$SO$_4$ (3.75 M, 100 mL) also cooled to 0° C. The mixture was left stirring at 0° C. for 5 min, and was then allowed to stir at RT for 1 h. The mixture was then saturated with brine, and extracted with EtOAc. The organic layer was then dried over anhydrous Na$_2$SO$_4$, and concentrated under reduced pressure. Purification by flash chromatography on silica gel afforded the product as a white solid (0.50 g, 19%); MS (EI) m/z=204 [M+].

Step, 4: 8-fluoro-1,2,3,4-tetrahydrodibenzo[b,d]furan-2-carbaldehyde

To a stirred solution of potassium t-butoxide (0.33 g, 2.94 mmol) in dry THF (4 mL) at RT was added methoxymethyltriphenylphosphonium chloride (1.01 g, 2.94 mmol), and the resulting red-colored solution was stirred at RT for 30 min. To the phosphorane thus formed, was added a solution of 8-fluoro-3,4-dihydrodibenzo[b,d]furan-2(1H)-one (0.15 g, 0.74 mmol) in dry THF (1 mL) and stirred at RT for 6 h. The reaction mixture was then diluted with water and extracted with ether. The organic extract was washed with brine, dried over anhydrous Na$_2$SO$_4$ and concentrated to afford compound as a E,Z-mixture of the enol ether. The resulting enol ether was dissolved in MeOH (5 mL) and treated with conc. HCl (2 mL). After stirring overnight, reaction mixture was quenched with NaHCO$_3$, and extracted with EtOAc. The organic extract was washed with brine, and dried over Na$_2$SO$_4$. Purification by flash chromatography on silica gel afforded the product as a white solid (0.05 g, 31%); MS (EI) m/z=218 [M+].

Step 5: 1-(8-fluoro-1,2,3,4-tetrahydrodibenzo[b,d]furan-2-yl)-N-{[(2S)-8-methyl-2,3-dihydro[1,4]dioxino[2,3-f]quinolin-2-yl]methyl}methanamine 8-fluoro-1,2,3,4-tetrahydrodibenzo[b,d]furan-2-carbaldehyde (0.040 g, 0.18 mmol), [(2S)-8-methyl-2,3-dihydro[1,4]dioxino[2,3-f]quinolin-2-yl]methylamine (0.042 g, 0.18 mmol), and NaBH$_3$CN (0.023 g, 0.38 mmol) were stirred together in MeOH (1.2 mL) under a N$_2$ atmosphere. To this mixture was added AcOH (0.023 mL) and reaction was allowed to stir for 3 h. The reaction mixture was concentrated and the resulting oil was purified by flash chromatography on silica gel to afford title compound as a mixture of two diastereomers (0.068 g, 88%). The diastereomers were separated by HPLC on a Chiracel AD column (2×25 cm), eluting with 100% ethanol; MS (ES) m/z=433.1 [M+H]+.

Diastereomer 1: 15.7 mg of the amine was isolated and converted into its dihydrochloride salt by treating a methanolic solution of the amine with 1 N HCL in ether. The resulting yellow solid was collected by vacuum filtration, washed with ethyl acetate and hexane, and dried under vacuum: MS (ES) m/z=433.2 [M+H]+.

Diastereomer 2: 16.6 mg of the amine was isolated and converted into its dihydrochloride salt by treating a methanolic solution of the amine with 1 N HCL in ether. The resulting yellow solid was collected by vacuum filtration, washed with ethyl acetate and hexane, and dried under vacuum: MS (ES) m/z=433.2 [M+H]+.

Example 106a and 106b

1-[(3S)-6-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (106a) and
1-[(3R)-6-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (106b)

To a solution of 6-methoxy-2,3,4,9-tetrahydro-1H-carbazole-3-carbaldehyde (670 mg, 2.9 mmol) and C-(8-methyl-2,3-dihydro-[1,4]dioxino[2,3-f]quinolin-2-yl)-methylamine (700 mg, 3.0 mmol) in 85 mL methanol were added acetic acid (0.50 mL) and sodium cyanoborohydride (500 mg, 8.0 mmol). The mixture was stirred at ambient temperature under nitrogen for four hours, after which the methanol was removed under reduced pressure and the residue partitioned between water and ethyl acetate. Product was purified by chromatography on silica gel eluting with 2% methanol in dichloromethane. The diastereomers were separated by chiral chromatography on a Chiralpak AD column eluting with methanol with diethylamine:

Diastereomer 1: 190 mg (13%) pale yellow solid: mp 67-77° C.; $[\alpha]_D$=−82.2° (methanol). Anal. Calc'd. for $C_{27}H_{29}N_3O_3.0.5\ C_3H_8O.0.5H_2O$: C, 70.93; H, 7.10; N, 8.71. Found: C, 71.13; H, 7.32; N, 8.61.

Diastereomer 2: 245 mg (18%) white solid: mp 72-83 C; $[\alpha]D$=+11.0° (methanol). Anal. Calc'd. for $C_{27}H_{29}N_3O_3.0.6H2O$: C, 71.38; H, 6.70; N, 9.25. Found: C, 71.46, H, 7.32; N, 9.21.

Example 107a and 107b

1-[(3S)-8-methoxy-2,3,4,9-tetrahydro-1H-carbazol-3-yl]N-{[(2S)-8-methyl-2,3-dihydro[1,4]dioxino[2,3-f]quinolin-2-yl]methyl}methanamine (107a) and
1-[(3R)-8-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (107b)

To a solution of 8-methoxy-2,3,4,9-tetrahydro-1H-carbazole-3-carbaldehyde (350 mg, 1.5 mmol) and C-(8-methyl-2,3-dihydro-[1,4]dioxino[2,3-f]quinolin-2-yl)-methylamine (280 mg, 1.2 mmol) in 45 mL methanol were added acetic acid (0.25 mL) and sodium cyanoborohydride (375 mg, 6.0 mmol). The mixture was stirred at ambient temperature under nitrogen for four hours, after which the methanol was removed under reduced pressure and the residue partitioned between water and ethyl acetate. Product was purified by chromatography on silica gel eluting with 2% methanol in dichloromethane. The diastereomers were separated by chiral chromatography on a Chiralpak AD column eluting with methanol with diethylamine:

Diastereomer 1: 102 mg (15%) white solid: mp 163-167° C. Anal. Calc'd. for $C_{27}H_{29}N_3O_3.0.5H_2O$: C, 71.66; H, 6.68; N, 9.29. Found: C, 71.99; H, 6.93; N, 9.16.

Diastereomer 2: 75 mg (11%) pale yellow solid: mp 81-86° C. Anal. Calc'd. for $C_{27}H_{29}N_3O_3.1.0H_2O$: C, 70.26; H, 6.77; N, 9.10. Found: C, 70.03, H, 6.84; N, 8.68.

Example 108a and 108b

1-[(3S)-7-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (108a) and
1-[(3R)-7-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (108b)

To a solution of 7-methoxy-2,3,4,9-tetrahydro-1H-carbazole-3-carbaldehyde (110 mg, 0.48 mmol) and C-(8-methyl-2,3-dihydro-[1,4]dioxino[2,3-j]quinolin-2-yl)-methylamine (88 mg, 0.38 mmol) in 14 mL methanol were added acetic acid (0.15 mL) and sodium cyanoborohydride (120 mg, 1.9 mmol). The mixture was stirred at ambient temperature under nitrogen for 16 hours, after which the methanol was removed under reduced pressure and the residue partitioned between water and ethyl acetate. Product was purified by chromatography on silica gel eluting with 2% methanol in dichloromethane. The diastereomers were separated by chiral chromatography on a Chiralpak AD column eluting with methanol with diethylamine:

Diastereomer 1: 21 mg (10%) white solid: mp 170-173° C. Anal. Calc'd. for $C_{27}H_{29}N_3O_3.0.8H_2O$: C, 70.81; H, 6.73; N, 9.18. Found: C, 70.91; H, 6.13; N, 8.82.

Diastereomer 2: 20 mg (10%) light brown solid: mp 76-87 C. Anal. Calc'd. for $C_{27}H_{29}N_3O_3.1.2H_2O$: C, 69.72; H, 6.80; N, 9.47. Found: C, 69.59, H, 6.65; N, 9.03

Example 109a and 109b

1-[(3S)-5-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (109a) and
1-[(3R)-5-methoxy-2,3,4,9-tetrahydro-1H-carbazol-3-yl]-N-{[(2S)-8-methyl-2,3-dihydro[1,4]dioxino[2,3-f]quinolin-2-yl]methyl}methanamine (109b)

To a solution of 5-methoxy-2,3,4,9-tetrahydro-1H-carbazole-3-carbaldehyde (140 mg, 0.61 mmol) and C-(8-methyl-2,3-dihydro-[1,4]dioxino[2,3-f]quinolin-2-yl)-methylamine (230 mg, 0.49 mmol) in 18 mL methanol were added acetic acid (0.20 mL) and sodium cyanoborohydride (150 mg, 2.4 mmol). The mixture was stirred at ambient temperature under nitrogen for 16 hours, after which the methanol was removed under reduced pressure and the residue partitioned between water and ethyl acetate. Product was purified by chromatography on silica gel eluting with 2% methanol in dichloromethane. The diastereomers were separated by chiral chromatography on a Chiralpak AD column eluting with methanol with diethylamine:

Diastereomer 1: 18 mg (5%) tan solid: mp 70-77° C.
Diastereomer 2: 25 mg (7%) tan solid: mp 92-100° C.

Example 110

1-[(2R,S)-8-Methyl-2,3-dihydro[1,4]dioxino[2,3-f]quinolin-2-yl]-N-{[(3R)-6-(trifluoromethoxy)-2,3,4,9-tetrahydro-1H-carbazol-3-yl]methyl}methanamine Step 1: Ethyl 6-(trifluoromethoxy)-2,3,4,9-tetrahydro-1H-carbazole-3-carboxylate A mixture of 4-oxocyclohexane carboxylic acid ethyl ester (3.75 g, 0.022 mol), 4-trifluoromethoxy phenylhydrazine hydrochloride (5 g, 0.0218 mol) and anhydrous ethanol (68 mL) was refluxed overnight under nitrogen. The solvent was evaporated and the residue partitioned between ethyl acetate and saturated aqueous sodium bicarbonate. The organic extracts were washed with 1:1 water/brine and dried over anhydrous magnesium sulfate. Removal of the solvent provided a yellow solid that was dried in vacuo (7.15 g). The material from two runs (11.64 g) was chromatographed on silica gel Merck 60 using a 5 to 15% gradient of ethyl acetate in hexane to yield the title compound as a pale tan solid (10.54 g, 92%), m.p. 131-132° C. MS [(+)ES, m/z}: 328.1 [M+H]+. MS [(-)ES, m/z]: 326.1 {M-H]-. HPLC: Chromolith Monolith column, 0.46×10 cm, gradient of acetonitrile in water (0.01% TFA), 4 mL/min, detection at 280 nm; $R_t$ 2.45 min.

Step 2: 6-(Trifluoromethoxy)-2,3,4,9-tetrahydro-1H-carbazole-3-carboxylic acid

A stirred solution of ethyl 6-(trifluoromethoxy)-2,3,4,9-tetrahydro-1H-carbazole-3-carboxylate of Step 1 (1.8 g, 5.5 mmol) in tetrahydrofuran (20 mL) and methanol (3 mL) was treated with 1N lithium hydroxide (11 mL) and heated under nitrogen in an oil bath kept at 40° C. for 2 hours. The organic solvents were evaporated, the residue was diluted with water, cooled in an ice bath and acidified with 2N hydrochloric acid (10 mL). The suspension was extracted with ethyl acetate, and the extracts were washed with brine and dried over anhydrous magnesium sulfate. Removal of the solvent provided a colorless foam that was dried in vacuo to yield the title compound (1.6 g). MS [(+)ES, m/z]: 300.1 [M+H]+. MS [(-)ES, m/z]: 298.0 [M-H]-. HPLC: Chromolith Monolith column, 0.46×10 cm, gradient of acetonitrile in water (0.01% TFA), 4 mL/min, detection at 254 nm; Rt 2.0 min.

Step 3: 6-(Trifluoromethoxy)-2,3,4,9-tetrahydro-1H-carbazole-3-carboxamide

A stirred solution of 6-(trifluoromethoxy)-2,3,4,9-tetrahydro-1H-carbazole-3-carboxylic acid of Step 2 (1.722 g, 5.75 mmol) in anhydrous tetrahydrofuran (37 mL) was treated under nitrogen with carbonyldiimidazole (1.37 g, 8.61 mmol). The yellow solution was stirred at room temperature for 5 hours and then anhydrous ammonia was bubbled through the solution for 30 minutes. The suspension was diluted with ethyl acetate and the organic phase was washed with 1:1 water/saturated aqueous sodium bicarbonate and 1:1 water/brine. The extracts were dried over anhydrous magnesium sulfate and evaporated to dryness to yield a pale yellow glass. The residue was purified by chromatography on silica gel Merck-60 using a 1% to 3% gradient of methanol in dichloromethane to provide the title compound (1.33 g, 77%) as an off white solid, m.p. 177-178° C. MS [(+)ES, m/z]: 299 [M+H]+. HRMS [(+)ESI, m/z]: 299.1004 [M+H]+. Calc'd for C14H14F3N2O2: 299.1007. HPLC: Chromolith Monolith column, 0.46×10 cm, gradient of acetonitrile in water (0.01% TFA), 4 mL/min, detection at 254 nm; Rt 1.8 min.

Step 4: 1-[6-(Trifluoromethoxy)-2,3,4,9-tetrahydro-1H-carbazol-3-yl]methanamine

To a stirred solution of 6-(trifluoromethoxy)-2,3,4,9-tetrahydro-1H-carbazole-3-carboxamide of Step 3 (1.22 g, 4.09 mmol) in anhydrous tetrahydrofuran kept under nitrogen, was added via syringe a 1M solution of lithium aluminum hydride in terahydrofuran (8.18 mmol). The pale yellow suspension was heated at 70° C. for 1 hour, allowed to cool to room temperature and then placed in an ice water bath. Under vigorous stirring the mixture was quenched with ethyl acetate, followed by a saturated aqueous solution of Rochelle salt. The slurry was extracted with ethyl acetate, the extracts were washed with brine and dried over anhydrous magnesium sulfate. Removal of the solvent provided a solid residue that was purified by chromatography over silica Merck 60 using a 2% to 10% gradient of methanolic ammonia in dichloromethane to provide the title compound as a white solid (0.946 g, 81.6%), m.p. 148-150° C. MS [(+)ES, m/z]: 285.1 [M+H]+. MS [(-)ES, m/z]: 283.1 [M-H]-. HRMS [(+)ESI, m/z]: 285.1212 [M+H]+. Calc'd for C14H16F3N2O: 285.1214. HPLC: Chromolith Monolith column, 0.46×10 cm, gradient of acetonitrile in water (0.01% TFA), 4 mL/min, detection at 280 nm; Rt 1.6 min.

Step 5. 1-[(2R,S)-8-Methyl-2,3-dihydro[1,4]dioxino[2,3-f]quinolin-2-yl]-N-{[(3S)-6-(trifluoromethoxy)-2,3,4,9-tetrahydro-1H-carbazol-3-yl]methyl}methanamine To a stirred solution of 1-[6-(trifluoromethoxy)-2,3,4,9-tetrahydro-1H-carbazol-3-yl]methanamine of Step 4 (0.841 g, 2.96 mmol) in warm acetonitrile (30 mL) kept under nitrogen was added solid potassium carbonate (0.410 g, 2.96 mmol) and [(2R)-8-methyl-2,3-dihydro[1,4]dioxino[2,3-f]quinolin-2-yl]methyl 4-bromobenzenesulfonate (1.148 g, 2.54 mmol, 1, SI7700-29-2). The mixture was heated in an oil bath kept at 80° C. for 9 hours, cooled, diluted with saturated aqueous sodium bicarbonate and water and extracted with ethyl acetate. The extracts were washed with 1:1 brine/water and dried over anhydrous magnesium sulfate. Removal of the solvent provided a foam that was purified by chromatography over silica gel Merck 60 using a gradient from 50:49:1 to 50:46:4 hexane/ethyl acetate/methanolic ammonia to yield the title compound as a mixture of diastereomers (0.614 g). MS [(+)ES, m/z]: 498.1 [M+H]+.

Example 111

1-[(2S)-8-Methyl-2,3-dihydro[1,4]dioxino[2,3-f]quinolin-2-yl]-N-{[(3S)-6-(trifluoromethoxy)-2,3,4,9-tetrahydro-1H-carbazol-3-yl]methyl}methanamine dihydrochloride The mixture of diastereomers (free base) of Example 110 was separated by chiral chromatography using a Varian Prep Chiralcel AD (2×15 cm) column; mobile phase: methanol with 0.1% diethylamine. The fractions corresponding to peak 1 were evaporated to dryness to provide the title compound as a colorless glass (free base). MS [(+)ES, m/z]: 498.1 {M+H]+. MS [(-)ES, m/z]: 496.1 {M+H]-. HRMS [(+)ESI, m/z]: 498.2010 {M+H]+. Calc'd for $C_{27}H_{27}F_3N_3O_3$: 498.2004.

The free base was dissolved in ethyl acetate and treated with 2 equivalents of 1N hydrochloride acid in diethyl ether. The yellow solid obtained upon addition of excess diethyl ether was collected, washed with diethyl ether and dried in vacuo to provide the the title compound dihydrochloride salt as a yellow solid, dec 170-172° C. HPLC: Chromolith Monolith column, 0.46×10 cm, gradient of acetonitrile in water (0.01% TFA), 4 mL/min, detection at 254 nm; $R_t$ 1.64 min.

Example 112

1-[(2S)-8-methyl-2,3-dihydro[1,4]dioxino[2,3-f]quinolin-2-yl]-N-{[(3R)-6-(trifluoromethoxy)-2,3,4,9-tetrahydro-1H-carbazol-3-yl]methyl}methanamine The other diastereoisomer (free base, colorless glass) was isolated using the method of Example 111 (corresponding to peak 2). MS [(+)ES, m/z]: 498.1 [M+H]+. MS [(−)ES, m/z]: 498.1 [M−H]−. HRMS [(+)ESI, m/z]: 498.2008 [M+H]+. Calc'd for $C_{27}H_{27}F_3N_3O_3$: 498.2004

The free base was converted to the dihydrochloride salt as described in Example 111. MS [(+)ES, m/z]: 498.1 [M+H]+. MS [(−)ES, m/z]: 498.1 [M−H]−. HPLC: Chromolith Monolith column, 0.46×10 cm, gradient of acetonitrile in water (0.01% TFA), 4 mL/min, detection at 254 nm; $R_t$ 2.79 min.

Example 113

8-OH-DPAT Binding Human 5-HT$_{1A}$ Receptor Cell Line

Stably transfected CHO cells were grown in DMEM containing 10% heat inactivated FBS and non-essential amino acids. Cells were scraped off the plate, transferred to centrifuge tubes, and washed twice by centrifugation (2000 rpm for 10 min., 4° C.) in buffer (50 mM Tris, pH 7.5). The resulting pellets were aliquoted and placed at −80° C. On day of assay, the cells were thawed on ice, and resuspended in buffer. The binding assay was performed in a 96 well microtiter plate in a total volume of 250 mL. Non-specific binding was determined in the presence of 10 mM 5HT; final ligand concentration was 1.5 nM. Following a 30 min. incubation at room temperature, the reaction was terminated by the addition of ice cold buffer and rapid filtration through a GF/B filter presoaked for 30 min. in 0.5% PEI. Compounds were initially tested in a single point assay to determine percent inhibition at 1, 0.1, and 0.01 mM. Subsequently, Ki values were determined for compounds defined to be active. Percent inhibition Ki was determined by RFComp (Lundon Software), with Serotonin 8-OH-DPAT as the reference compounds. Results are presented below in Table 1.

Example 114

$^3$H-Paroxetine Binding to Assess Affinity of Drugs for the Serotonin Transporter A protocol similar to that used by Cheetham et al. (Neuropharmacol. 32:737, 1993) was used to determine the affinity of compounds for the serotonin transporter. Briefly, frontal cortical membranes prepared from male S.D. rats were incubated with $^3$H-paroxetine (0.1 nM) for 60 min at 25° C. All tubes also contained either vehicle, test compound (one to eight concentrations), or a saturating concentration of fluoxetine (10 µM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method of Cheng and Prusoff (Biochem. Pharmacol. 22: 3099, 1973); Ki=IC$_{50}$/((Radioligand conc.)/(1+ KD)). Results are presented below in Table 1.

Example 115 cAMP RIA in Human 5-HT$_{1A}$ Receptor Cell Line

Stably transfected CHO cells were grown in DMEM containing 10% heat inactivated FBS and non-essential amino acids. The cells were plated at a density of $10^6$ cells per well in a 96 well plate and incubated for 2 days in a CO$_2$ incubator. On the second day, the media was replaced with 0.1 ml Krebs and incubated 15 minutes at 37° C. The media was then replaced with Krebs buffer containing 500 uM IBMX and incubated 5 minutes at 37° C. Wells were treated with forskolin (1 uM final conc) followed immediately by test compound (0.1 and 1 uM for initial screen) and incubated for an additional 10 min at 37° C. Reaction was terminated by removal of the media and addition of 0.5 ml ice cold assay buffer (supplied in RIA kit). Plates are stored at −20° C. prior to assessment of cAMP formation by RIA. Compounds shown to have no agonist activities were further analyzed for ability to reverse agonist activity. In separate experiments, 6 concentrations of antagonist were preincubated for 20 min prior to the addition of agonist and forskolin. Cells were harvested as described. The cAMP kit is supplied by Amersham and the RIA is performed as per kit instructions. In the initial screen, percent inhibition of forskolin stimulated cAMP was measured. In the secondary screen, IC$_{50}$ of reversal of agonist activity was measured. Calculations of IC$_{50}$ were performed by GraphPad Prism. Serotonin, BMY 7378, Buspirone, and 8-OH-DPAT were used as reference compounds. Results are presented below in Table 1.

Example 116

GTPγS Binding Assay

The $^{35}$S-GTPγS binding assay similar to that used by Lazareno and Birdsall (Br. J. Pharmacol., 1993, 109: 1120) was used to determine the test compound's ability to affect the binding of $^{35}$S-GTPγS to membranes containing cloned human 5-HT$_{1A}$ receptors. Agonists produce an increase in binding whereas antagonists produce no increase but rather reverse the effects of the standard agonist 8-OH-DPAT. The test compound's maximum stimulatory effect is represented as the $E_{max}$, while its potency is defined by the EC$_{50}$. The test compound's maximum inhibitory effect is represented as the $I_{max}$, while its potency is defined by the IC$_{50}$. [$^3$H]-8-OH-DPAT was used to determine maximum agonist or antagonist response. Results are presented below in Table 1.

TABLE 1

| Example No. | h5-HT$_{1A}$ Affinity, Ki (nM) | rb-5-HH-T, Ki (IC$_{50}$), (nM) | h-5-HT-T IC$_{50}$, (nM) | c-AMP, (EC$_{50}$)[a], (IC$_{50}$)[b], (E$_{max}$)[c], (nM) | GTPγS, (EC$_{50}$)[a], (IC$_{50}$)[b], (E$_{max}$)[c], (I$_{max}$)[d], (nM) |
|---|---|---|---|---|---|
| 1 | 2.23 | (49.4) | | | 15.25[b] |
| 2 | 1.36 | (5.26) | | | 7.2[b] |
| 3 | 1.259 | (6.61) | | | 79.05[b] |

TABLE 1-continued

| Example No. | h5-HT$_{1A}$ Affinity, Ki (nM) | rb-5-HH-T, Ki (IC$_{50}$), (nM) | h-5-HT-T IC$_{50}$, (nM) | c-AMP, (EC$_{50}$)$^a$, (IC$_{50}$)$^b$, (E$_{max}$)$^c$, (nM) | GTPγS, (EC$_{50}$)$^a$, (IC$_{50}$)$^b$, (E$_{max}$)$^c$, (I$_{max}$)$^d$, (nM) |
|---|---|---|---|---|---|
| 5 | 2.03 | (2.56) | | 144$^b$ | |
| 6 | 3.65 | (9.01) | | 532.5$^b$ | |
| 7 | 0.34 | (7.74) | | 78.45$^b$ | |
| 8 | 2.5 | (3.1) | | 39.4$^b$ | |
| 9 | 3.7 | (57.6) | | 105$^b$ | |
| 10 | 4.95 | (11.3) | | 248.5$^b$ | |
| 11 | 16.67 | (124) | | 49.2$^b$ | |
| 12 | 0.54 | (180) | | 26.65$^b$ | |
| 13 | 1.8 | (120) | | 22.15$^b$ | |
| 14 | 13.65 | (3.61) | | 79.5$^b$ | |
| 15 | 15 | (2.25) | | 888$^b$ | |
| 31 diastereomer 1 | 1.14 | 9.90 | 337 | 62%$^c$ | 155$^b$ 95%$^d$ |
| 31 diastereomer 2 | 3.67 | 51.5 | 547 | 62%$^c$ | 290$^b$ 65%$^d$ |
| 32 diastereomers 1 | 8.07 | >1000 | Not tested | 67.6$^b$ | 494$^b$ 100%$^d$ |
| 32 diastereomer 2 | 6.49 | 47.6 | 885 | 17.7$^b$ | Not tested |
| 39 diastereomer 1 | 7.09 | 210 | 2056 | 62%$^c$ | 645$^b$ 100%$^d$ |
| 39 diastereomer 2 | 2.16 | 184 | 1437 | 75%$^c$ | 117$^b$ 80%$^d$ |
| 40 | 680.00 | 48.40 | 1.24 ± 0.16 | 4.06$^a$ 100.00$^c$ | 7.10$^a$ 75.00$^b$ 46.00$^c$ 34.00$^d$ |
| 41 | 242.00 | 9.45 | 0.58 ± 0.14 | 4.13$^a$ 94.00$^c$ | 24.80$^a$ 94.00$^c$ |
| 42 | 751.00 | 58.00 | 2.80 ± 0.12 | 36.40$^a$ 87.00$^c$ | 63.00$^a$ 351.00$^b$ 39.00$^c$ 71.00$^d$ |
| 43 | 432.00 | 45.10 | 19.25 ± 2.51 | 233.00$^a$ 61.00$^c$ | 197.00$^b$ 98.50$^d$ |
| 44 | 620.00 | | 22.05 ± 2.51 | 225.00$^a$ 74.0$^c$ | |
| 45 | 365.00 | 34.30 | 38.95 ± 0.18 | 157.00$^a$ 59.00$^c$ | 461.00$^b$ |
| 46 | 231.00 | 8.55 | 52.45 ± 1.73 | 155.0$^a$ 70.00$^c$ | |
| 47 | 186.00 | 12.80 | 102.00 ± 7.07 | 300.00$^a$ 59.00$^c$ | |
| 48 | 7.40 | 46.68 ± 2.07 | 31.85 ± 5.34 | 167.60$^b$ | |
| 50 | 226.00 | 26.95 | 5.73 ± 0.33 | 137.00$^b$ | 179.00$^b$ 100.00$^d$ |
| 51 | 1288.00 | 88.00 | 22.30 ± 3.32 | 171.00$^a$ 59.00$^c$ | |
| 52 | 936.00 | 670.00 | 19.50 ± 0.28 | 312.00$^a$ 70.00$^c$ | 1584.00$^b$ 100.00$^d$ |
| 53 | 5739.00 | 498.00 | 39.15 ± 3.85 | 126.00$^a$ 68.00$^c$ | |
| 54 | 617.00 | 96.50 | 16.60 ± 0.85 | 177.00$^a$ 48.00$^c$ | 581.00$^b$ 63.00$^d$ |
| 55 | 850.00 | 110.00 | 8.50 ± 0.18 | 211.00$^a$ 67.00$^c$ | 1131.00$^b$ 74.00$^d$ |
| 56 | 1728.00 | 127.00 | 18.15 ± 0.39 | 154.00$^a$ 69.00$^c$ | 3104.00$^b$ |
| 57 | 6141.00 | 1574.50 | 1126.00 ± 108.89 | | |
| 58 | 1185.00 | 358.50 | 113.2 ± 22.49 | 22.00$^c$ | |
| 59 | 3116.00 | 361.50 | 114.75 ± 16.44 | 431.00$^a$ 81.00$^c$ | |
| 60 | | 393.50 | 995.50 ± 24.40 | | |
| 61 | | | 1705.00 ± 45.96 | | |
| 62 | 1965.00 | | 730.00 ± 9.19 | | |
| 63 | | 113.00 | 389.00 ± 38.18 | 1350.00$^a$ 73.00$^c$ | |
| 64 | | 455.00 | 2490.00 ± 268.70 | | |
| 65 | | | 403.00 ± 28.99 | | |
| 66 | | | 62.30 ± 9.19 | 163.00$^a$ 67.50$^c$ | |
| 67 | | | 504.50 ± 9.55 | | |

TABLE 1-continued

| Example No. | h5-HT$_{1A}$ Affinity, Ki (nM) | rb-5-HH-T, Ki (IC$_{50}$), (nM) | h-5-HT-T IC$_{50}$, (nM) | c-AMP, (EC$_{50}$)$^a$, (IC$_{50}$)$^b$, (E$_{max}$)$^c$, (nM) | GTPγS, (EC$_{50}$)$^a$, (IC$_{50}$)$^b$, (E$_{max}$)$^c$, (I$_{max}$)$^d$, (nM) |
|---|---|---|---|---|---|
| 68 | 3715.00 | 293.50 | 15.25 ± 0.74 | 34.75$^c$ | |
| 69 | 1588.00 | 220.50 | 35.80 ± 0.71 | 548.00$^a$ 63.00$^c$ | |

When ranges are used herein for physical properties, such as molecular weight, or chemical properties, such as chemical formulae, all combinations and subcombinations of ranges of specific embodiments therein are intended to be included.

The disclosure of each patent, patent application, and publication cited or described in this document is hereby incorporated by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound which is:

N-[(6-fluoro-2,3,4,9-tetrahydro-1H-carbazol-2-yl)methyl]-N-{[(2S)-8-methyl-2,3-dihydro[1,4]dioxino[2,3-f]quinolin-2-yl]methyl}amine;

N-[(6-fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

N-{[(3S)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-[(6-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

N-{[(3S)-6-fluoro-9-methyl-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-6-fluoro-9-methyl-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-6,8-difluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3S)-6,8-difluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

[(5-fluoro-2,3,4,9-tetrahydro-1H-carbazol-3-yl)methyl]{[(2S)-8-methyl-2,3-dihydro[1,4]dioxino[2,3-f]quinolin-2-yl]methyl}amine;

N-[(5-fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

N-[(7-fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}amine;

(3S)-3-[({[(2S)-8-methyl-2,3-dihydro[1,4]dioxino[2,3-f]quinolin-2-yl]methyl}amino)methyl]-2,3,4,9-tetrahydro-1H-carbazole-6-carbonitrile;

(3R)-3-[({[(2S)-8-methyl-2,3-dihydro[1,4]dioxino[2,3-f]quinolin-2-yl]methyl}amino)methyl]-2,3,4,9-tetrahydro-1H-carbazole-6-carbonitrile;

2-(6-Fluoro-2,3,4,9-tetrahydro-1H-carbazol-3-yl)ethyl]{[(2S)-8-methyl-2,3-dihydro[1,4]dioxino[2,3-f]quinolin-2-yl]methyl}amine;

{2-[(3R)-6-Fluoro-2,3,4,9-tetrahydro-1H-carbazol-3-yl]ethyl}{[(2S)-8-methyl-2,3-dihydro[1,4]dioxino[2,3-f]quinolin-2-yl]methyl}amine;

{2-[(3S)-6-Fluoro-2,3,4,9-tetrahydro-1H-carbazol-3-yl]ethyl}{[(2S)-8-methyl-2,3-dihydro[1,4]dioxino[2,3-f]quinolin-2-yl]methyl}amine;

N-{[(2S)-8-methyl-2,3-dihydro[1,4]dioxino[2,3-f]quinolin-2-yl]methyl}-2,3,4,9-tetrahydro-1H-carbazol-2-amine;

(2R)-N-{[(2S)-8-methyl-2,3-dihydro[1,4]dioxino[2,3-f]quinolin-2-yl]methyl}-2,3,4,9-tetrahydro-1H-carbazol-2-amine;

(2S)-N-{[(2S)-8-methyl-2,3-dihydro[1,4]dioxino[2,3-f]quinolin-2-yl]methyl}-2,3,4,9-tetrahydro-1H-carbazol-2-amine;

6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

(2R)-6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

(2S)-6-Fluoro-N-{[(2S)-8-methyl-2,3-dihydro[1,4]dioxino[2,3-f]quinolin-2-yl]methyl}-2,3,4,9-tetrahydro-1H-carbazol-2-amine;

[(8-Fluoro-1,2,3,4-tetrahydrodibenzo[b,d]thien-2-yl)methyl]{[(2S)-8-methyl-2,3-dihydro[1,4]dioxino[2,3-f]quinolin-2-yl]methyl}amine;

{[(2S)-8-methyl-2,3-dihydro[1,4]dioxino[2,3-f]quinolin-2-yl]methyl}(1,2,3,4-tetrahydrodibenzo[b,d]thien-2-ylmethyl)amine;

{[(2S)-8-methyl-2,3-dihydro[1,4]dioxino[2,3-f]quinolin-2-yl]methyl}(1,2,3,4-tetrahydrodibenzo[b,d]thien-2-ylmethyl)amine;

N-{[(3S)-6-trifluoromethoxy-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}ethanamine;

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}propan-1-amine;

(Cyclopropylmethyl)[(6-fluoro-2,3,4,9-tetrahydro-1H-carbazol-3-yl)methyl]({[(2S)-8-methyl-2,3-dihydro[1,4]dioxino[2,3-f]quinolin-2-yl]methyl}amine;

N-[(6-Fluoro-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclobutanamine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}propan-1-amine;

(Cyclopropylmethyl){[(3R)-6-fluoro-2,3,4,9-tetrahydro-1H-carbazol-3-yl]methyl}{[(2S)-8-methyl-2,3-dihydro[1,4]dioxino[2,3-f]quinolin-2-yl]methyl}amine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclobutanamine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}propan-2-amine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}butan-2-amine;

N-{[(3R)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclopentanamine;

N-{[(3R)-6-fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclohexanamine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}propan-2-amine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}butan-2-amine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclopentanamine;

N-{[(3S)-6-Fluoro-2,3,4,9-tetrahydro-1H-carbazol-3-yl]methyl}-N-{[(2S)-8-methyl-2,3-dihydro[1,4]dioxino[2,3-f]quinolin-2-yl]methyl}cyclohexanamine;

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}propan-2-amine;

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclopentanamine;

N-[(6-Fluoro-9-methyl-2,3,4,9-tetrahydro-1H-carbazol-3-yl)methyl]-N-{[(2S)-8-methyl-2,3-dihydro[1,4]dioxino[2,3-f]quinolin-2-yl]methyl}cyclohexanamine;

{[(3S)-6-Fluoro-9-methyl-2,3,4,9-tetrahydro-1H-carbazol-3-yl]methyl{[(2S)-8-methyl-2,3-dihydro[1,4]dioxino[2,3-f]quinolin-2-yl]methyl}amine;

{[(3R)-6-Fluoro-9-methyl-2,3,4,9-tetrahydro-1H-carbazol-3-yl]methyl{[(2S)-8-methyl-2,3-dihydro[1,4]dioxino[2,3-f]quinolin-2-yl]methyl}amine 5,6-Dichloro-2,3,4,9-tetrahydro-1H-carbazol-3-ylmethyl)-(8-methyl-2,3-dihydro-[1,4]dioxino[2,3-f]quinolin-2-ylmethyl)-amine;

(6-Chloro-2,3,4,9-tetrahydro-1H-carbazol-3-ylmethyl)-(8-methyl-2,3-dihydro-[1,4]dioxino[2,3-f]quinolin-2-ylmethyl)-amine;

(5-Chloro-6-fluoro-2,3,4,9-tetrahydro-1H-carbazol-3-ylmethyl)-(8-methyl-2,3-dihydro-[1,4]dioxino[2,3-f]quinolin-2-ylmethyl)-amine;

(7-Chloro-6-fluoro-2,3,4,9-tetrahydro-1H-carbazol-3-ylmethyl)-(8-methyl-2,3-dihydro-[1,4]dioxino[2,3-f]quinolin-2-ylmethyl)-amine;

(6-Chloro-2,3,4,9-tetrahydro-1H-carbazol-3-ylmethyl)-(8-methyl-2,3-dihydro-[1,4]dioxino[2,3-f]quinolin-2-ylmethyl)-amine;

(7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(S)-ylmethyl)-amine;

(7,8-Dihydro-3H-6,9-dioxa-3-aza-cyclopenta[a]naphthalen-8-(S)-ylmethyl)-(6-fluoro-2,3,4,9-tetrahydro-1H-carbazol-3-(R)-ylmethyl)-amine;

(2,3-Dihydro-1,4-dioxa-5,8-diaza-phenanthren-3-(S)-ylmethyl)-(6-fluoro-2,3,4,9-tetrahydro-1H-carbazol-3-(R)-ylmethyl)-amine;

(2,3-Dihydro-1,4-dioxa-5,8-diaza-phenanthren-3-(S)-ylmethyl)-(6-fluoro-2,3,4,9-tetrahydro-1H-carbazol-3-(S)-ylmethyl)-amine;

(6-Fluoro-2,3,4,9-tetrahydro-1H-carbazol-3-(R)-ylmethyl)-(7-methyl-2,3-dihydro-1,4-dioxa-5,8-diaza-phenanthren-3-(S)-ylmethyl)-amine;

(6-Fluoro-2,3,4,9-tetrahydro-1H-carbazol-3-(S)-ylmethyl)-(7-methyl-2,3-dihydro-1,4-dioxa-5,8-diaza-phenanthren-3-(S)-ylmethyl)-amine;

(6-Fluoro-2,3,4,9-tetrahydro-1H-carbazol-3-(R)-ylmethyl)-(6-methyl-2,3-dihydro-1,4-dioxa-5,8-diaza-phenanthren-3-(S)-ylmethyl)-amine;

(6-Fluoro-2,3,4,9-tetrahydro-1H-carbazol-3-(S)-ylmethyl)-(6-methyl-2,3-dihydro-1,4-dioxa-5,8-diaza-phenanthren-3-(S)-ylmethyl)-amine;

{[(2R)-8-Fluoro-1,2,3,4-tetrahydrodibenzo[b,d]thien-2-yl]methyl}{[(2S)-8-methyl-2,3-dihydro[1,4]dioxino[2,3-f]quinolin-2-yl]methyl}amine;

{[(2S)-8-Fluoro-1,2,3,4-tetrahydrodibenzo[b,d]thien-2-yl]methyl}{[(2S)-8-methyl-2,3-dihydro[1,4]dioxino[2,3-f]quinolin-2-yl]methyl}amine;

{[(2S)-8-methyl-2,3-dihydro[1,4]dioxino[2,3-f]quinolin-2-yl]methyl}[(2S)-1,2,3,4-tetrahydrodibenzo[b,d]thien-2-ylmethyl]amine;

{[(2S)-8-methyl-2,3-dihydro[1,4]dioxino[2,3-f]quinolin-2-yl]methyl}[(2R)-1,2,3,4-tetrahydrodibenzo[b,d]thien-2-ylmethyl]amine;

{[(3R)-7-fluoro-1,2,3,4-tetrahydrodibenzo[b,d]thien-3-yl]methyl}{[(2S)-8-methyl-2,3-dihydro[1,4]dioxino[2,3-f]quinolin-2-yl]methyl}amine;

{[(3S)-7-fluoro-1,2,3,4-tetrahydrodibenzo[b,d]thien-3-yl]methyl}{[(2S)-8-methyl-2,3-dihydro[1,4]dioxino[2,3-f]quinolin-2-yl]methyl}amine;

N-{[(3S)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

N-{[(3R)-2,3,4,9-tetrahydro-1H-carbazol-3-yl]methyl}-N-{[(2S)-8-methyl-2,3-dihydro[1,4]dioxino[2,3-f]quinolin-2-yl]methyl}amine;

(3R)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine;

(3S)-6-fluoro-N-{(2S)-8-methyl-2,3-dihydro-[1,4]dioxino[2,3-f]quinolin-2-yl]methyl}-2,3,4,9-tetrahydro-1H-carbazol-3-amine;

[(2S)-2,3-dihydro[1,4]dioxino[2,3-f]quinolin-2-ylmethyl]{[(3S)-6-fluoro-2,3,4,9-tetrahydro-1H-carbazol-3-yl]methyl}amine;

[(2S)-2,3-dihydro[1,4]dioxino[2,3-f]quinolin-2-ylmethyl]{[(3R)-6-fluoro-2,3,4,9-tetrahydro-1H-carbazol-3-yl]methyl}amine; or a pharmaceutically acceptable salt thereof.

* * * * *